United States Patent
Ohtaki et al.

(10) Patent No.: US 7,374,910 B2
(45) Date of Patent: May 20, 2008

(54) DNA ENCODING GALANIN RECEPTOR ACTIVATING PEPTIDE

(75) Inventors: Tetsuya Ohtaki, Tsukuba (JP); Hideki Matsui, Tsukuba (JP); Yoshihiro Ishibashi, Tsukuba (JP); Kazuhiro Ogi, Tsukuba (JP); Chieko Kitada, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 154 days.

(21) Appl. No.: 11/376,694

(22) Filed: Mar. 15, 2006

(65) Prior Publication Data

US 2006/0155109 A1    Jul. 13, 2006

Related U.S. Application Data

(62) Division of application No. 09/646,078, filed as application No. PCT/JP99/01482 on Mar. 24, 1999, now Pat. No. 7,064,181.

(30) Foreign Application Priority Data

Mar. 25, 1998  (JP) .................................. 10-078139
Sep. 21, 1998  (JP) .................................. 10-266972

(51) Int. Cl.
   *C01N 15/11*   (2006.01)
   *C01N 15/63*   (2006.01)
   *C01N 5/10*    (2006.01)

(52) U.S. Cl. .................. 435/69.1; 435/320.1; 435/325; 536/23.5

(58) Field of Classification Search ...................... None
See application file for complete search history.

(56) References Cited

U.S. PATENT DOCUMENTS 5,576,296 A    11/1996  Bartfai et al.

FOREIGN PATENT DOCUMENTS

WO    WO 92/12997    8/1992
WO    WO 92/20709    11/1992

OTHER PUBLICATIONS

N. Chartel, et al., "Frog Vasoactive Intestinal Polypeptide and Galanin: Primary Structures and Effects on Pituitary Adenylate Cyclase", Endocrinology, 136(7): 3079-3086(1995).

A. Norberg, et al., Chemical Detection of Natural Peptides by Specific Structures, Federation of European Biochemical Societies, 288(1,2): 151-153(1991).

K. Tatemoto, et al., "Galanin—A Novel Biologically Active Peptide from Porcine Intestine", Federal of European Biochemical Societies, 164(1): 124-128(1983).

A. Rokaeus, et al., "Construction of a Porcine Adrenal Medullary cDNA Library and Nucleotide Sequence Analysis of Two Clones Encoding a Galanin Precursor", Proc. Natl. Acad. Sci. USA, 83: 6287-6291(1986).

R. Sillard, et al., "Variant Forms of Galanin Isolated From Porcine Brain", Peptides, 13: 1055-1060(1992).

K. Smith, et al., "Expression Cloning of a Rat Hypothalamic Galanin Receptor Coupled to Phosphoinositide Turnover", The Journal of Biological Chemistry, 272(39): 24612-24616(1997).

S. Wang, et al., "Cloning and Expressional Characterization of a Novel Galanin Receptor", The Journal of Biological Chemistry, 272(51): 31949-31952(1997).

K. Smith, et al., "Cloned Human and Rat Galanin GALR3 Receptors", The Journal of Biological Chemistry, 273(36): 23321-23326(1998).

Pooga, et al., "Novel Galanin Receptor Ligands", Journal of Peptide Research 51(1): 65-74(1998).

*Primary Examiner*—Michael Pak
(74) *Attorney, Agent, or Firm*—David G. Conlin; Kathryn A. Piffat; Edwards Angell Palmer & Dodge LLP

(57) ABSTRACT

The present invention relates to a peptide comprising an amino acid sequence identical to or substantially identical to an amino acid sequence represented by SEQ ID NO: 35 and having an ability of binding to a receptor protein comprising an amino acid sequence identical to or substantially identical to an amino acid sequence represented by SEQ ID NO: 1, SEQ ID NO: 2 or SEQ ID NO: 3, or a precursor thereof, its amide or ester, or a salt thereof.

An inventive peptide-encoding DNA or equivalent can be employed in (1) a development of a receptor binding assay system using an expression system of a recombinant receptor protein and a screening for a pharmaceutical candidate compound, and (2) a development of a pharmaceutical having a reduced side effect such as a memory function improving agent, an appetite improving agent, an uterine, renal, prostatic, testicular or skeletal muscle function regulating agent.

8 Claims, 13 Drawing Sheets

| G2000SWXL Calibration | | | |
|---|---|---|---|
| Peptides | MW | logMW | RT(min) |
| BSA | 66,000 | 4.82 | 12.6 |
| Trypsin inhibitor, soybean | 20,100 | 4.303 | 14.982 |
| Lysozyme, egg white | 14,300 | 4.155 | 16.392 |
| Adrenomedulin | 6028.8 | 3.78 | 16.662 |
| Gastric inhibitory peptide | 4983.6 | 3.698 | 17.547 |
| PACAP38 | 4534.3 | 3.657 | 16.6 |
| Neuropeptide Y | 4271.7 | 3.631 | 17.813 |
| β-Endorphin | 3465 | 3.54 | 18.02 |
| Galanin | 3157.4 | 3.499 | 18.858 |
| SRIF28 | 3146.5 | 3.498 | 19.003 |

Fig. 6

```
                                                                    1
MPRGCALLLASLLLASALSATLGLGSPVKEKRGW
                                APVHRGRGW
                                1    5      10

5         10        15       20       25      29
TLNSAGYLLGPHAIDNHRSFHDKYGLAGKRELEP
TLNSAGYLLGPVLHPPSXAEGGGKGKTALGILDL
         15        20       25       30      35       40    44

EDEARPGGFDRLQSEDKAIRTIMEFLAFLHLKEA
--XAIDGLPYPQSTX

GALGRLPGLPSAASSEDAGQS
```

Comparison of amino acid sequences
The amino acid sequence of porcine galanin precursor
is shown on upper line, and the amino acid sequence of the
peptide of the present invention is shown on lower line.

Fig. 8
a
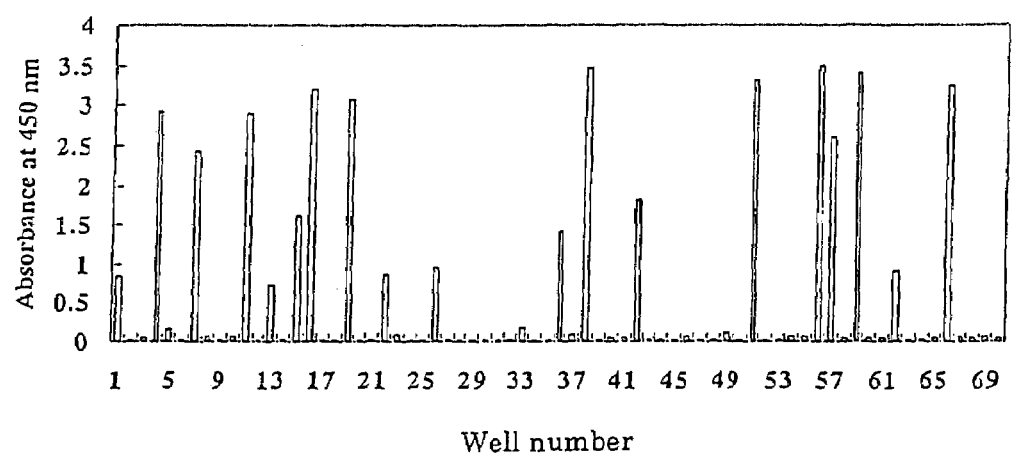
b
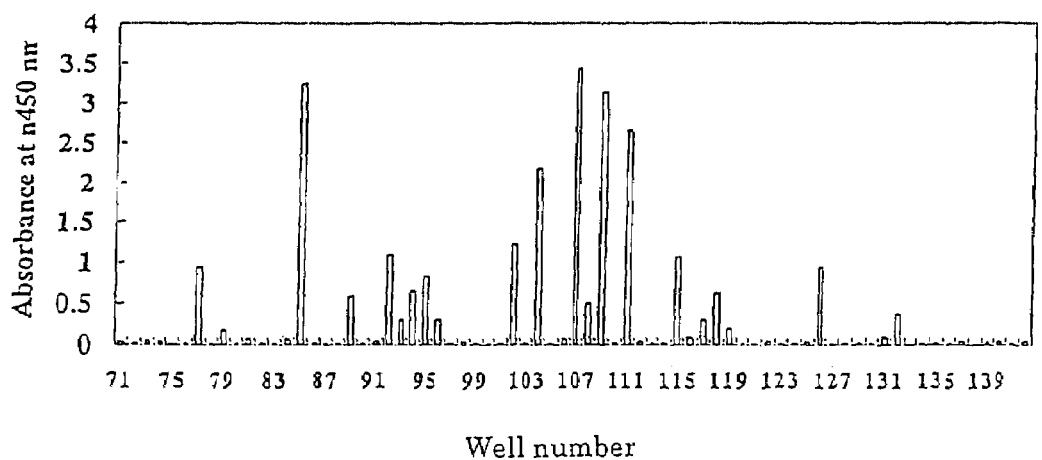

1: marker
2: non-reduction condition 2ug/lane
3: reduction condition 2ug/lane

SEQUENCE LISTING

<160> NUMBER OF SEQ ID NOS: 61

<210> SEQ ID NO 1
<211> LENGTH: 346
<212> TYPE: PRT
<213> ORGANISM: Rat

<400> SEQUENCE: 1

Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220

Leu His Lys Lys Leu Lys Asn Met Ser Lys Lys Ser Glu Ala Ser Lys
225                 230                 235                 240

Lys Lys Thr Ala Gln Thr Val Leu Val Val Val Val Phe Gly Ile
                245                 250                 255

Ser Trp Leu Pro His His Val Ile His Leu Trp Ala Glu Phe Gly Ala
            260                 265                 270

Phe Pro Leu Thr Pro Ala Ser Phe Phe Arg Ile Thr Ala His Cys
        275                 280                 285

Leu Ala Tyr Ser Asn Ser Ser Val Asn Pro Ile Ile Tyr Ala Phe Leu
    290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp

```
                    325                 330                 335
Thr Pro Pro Ser Thr Asn Cys Thr His Val
            340                 345

<210> SEQ ID NO 2
<211> LENGTH: 372
<212> TYPE: PRT
<213> ORGANISM: Rat

<400> SEQUENCE: 2

Met Asn Gly Ser Gly Ser Gln Gly Ala Glu Asn Thr Ser Gln Glu Gly
1               5                   10                  15

Gly Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
            180                 185                 190

Val Phe Ser Tyr Leu Leu Pro Val Leu Val Leu Ser Leu Thr Tyr Ala
        195                 200                 205

Arg Thr Leu Arg Tyr Leu Trp Arg Thr Val Asp Pro Val Thr Ala Gly
    210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350
```

-continued

Val Pro Pro Pro Ala Leu Pro Asn Cys Thr Ala Ser Ser Arg Thr Leu
            355                 360                 365

Asp Pro Ala Cys
        370

<210> SEQ ID NO 3
<211> LENGTH: 370
<212> TYPE: PRT
<213> ORGANISM: Rat

<400> SEQUENCE: 3

Met Ala Asp Ile Gln Asn Ile Ser Leu Asp Ser Pro Gly Ser Val Gly
1               5                   10                  15

Ala Val Ala Val Pro Val Ile Phe Ala Leu Ile Phe Leu Leu Gly Met
            20                  25                  30

Val Gly Asn Gly Leu Val Leu Ala Val Leu Leu Gln Pro Gly Pro Ser
        35                  40                  45

Ala Trp Gln Glu Pro Ser Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Ala Ile Tyr Thr Leu Asp Ala Trp Leu Phe Gly Ala Phe Val Cys Lys
                85                  90                  95

Thr Val His Leu Leu Ile Tyr Leu Thr Met Tyr Ala Ser Ser Phe Thr
            100                 105                 110

Leu Ala Ala Val Ser Leu Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190

Tyr Leu Leu Pro Val Ala Val Ser Leu Ala Tyr Gly Arg Thr Leu
        195                 200                 205

Cys Phe Leu Trp Ala Ala Val Gly Pro Ala Gly Ala Ala Ala Ala Glu
210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ser Leu Ala Ser Arg His Phe Arg Ala Arg Phe Arg Arg
    290                 295                 300

Leu Trp Pro Cys Gly Arg Arg Arg His Arg His His Arg Ala His
305                 310                 315                 320

Arg Ala Leu Arg Arg Val Gln Pro Ala Ser Ser Gly Pro Ala Gly Tyr
                325                 330                 335

Pro Gly Asp Ala Arg Pro Arg Gly Trp Ser Met Glu Pro Arg Gly Asp
            340                 345                 350

```
        Ala Leu Arg Gly Gly Gly Glu Thr Arg Leu Thr Leu Ser Pro Arg Gly
            355                 360                 365

Pro Gln
    370

<210> SEQ ID NO 4
<211> LENGTH: 1041
<212> TYPE: DNA
<213> ORGANISM: Rat

<400> SEQUENCE: 4
atggaactgg ctccggtgaa cctcagtgaa gggaatggga gcgaccctga acctccagcg      60
gaacccaggc cgctcttcgg catcggcgtg gagaacttca tcacgctggt ggtgtttggc     120
cttattttcg cgatgggcgt gctgggcaac agcctggtga tcaccgtgct ggcgcgcagc     180
aaaccgggca agccgcgcag caccaccaac ctgttcatcc tcaacctgag catcgcagac     240
ctggcctacc tgctcttctg catccctttc caggccaccg tgtacgcact gcccacctgg     300
gtgctgggcg ccttcatctg caagtttata cactacttct tcaccgtgtc catgctcgtg     360
agcatcttca ccctggccgc gatgtctgtg atcgctatg tggccattgt gcattcacgg      420
cgctcctcct ccctcagggt gtcccgcaac gcgctgctgg gcgtgggctt catctgggcg     480
ctgtccatcg ctatggcctc gccggtggcc tactaccagc gccttttca tcgggacagc      540 aaccaaacct tctgctggga gcactggccc aaccaactcc acaagaaggc ttacgtggtg     600
tgcactttcg tctttggtta ccttctgccc ttactgctca tctgcttttg ctatgccaag     660
gttctcaatc atctgcataa aaagttgaag aacatgtcaa aaagtcaga ggcatccaag      720 aaaaagactg cacagactgt cctggtggtc gttgtggtat tggcatatc atggctgccc      780 catcatgtca tccacctctg gctgagttc ggagcattcc cgctgacccc agcttccttc      840
ttcttcagaa tcactgccca ctgcctggca tacagcaact cctcggtgaa ccccatcatc     900
tacgcctttc tctcagaaaa cttccggaag gcgtacaagc aagtgttcaa gtgccgtgtt     960
tgcaatgagt cgccgcacgg cgatgctaaa gaaaagaacc gaatagatac cccgccctcc    1020
accaactgca cccacgtgtg a                                              1041

<210> SEQ ID NO 5
<211> LENGTH: 1119
<212> TYPE: DNA
<213> ORGANISM: Rat

<400> SEQUENCE: 5
atgaatggct ccggcagcca gggcgcggag aacacgagcc aggaaggcgg tagcggcggc      60
tggcagcctg aggcggtcct tgtacccta tttttcgcgc tcatcttcct cgtgggcacc     120
gtgggcaacg cgctggtgct ggcggtgctg ctgcgcggcg ccaggcggt cagcaccacc     180 aacctgttca tcctcaacct gggcgtggcc gacctgtgtt tcatcctgtg ctgcgtgcct     240
ttccaggcca ccatctacac cctggacgac tgggtgttcg gctcgctgct ctgcaaggct     300
gttcatttcc tcatctttct cactatgcac gccagcagct tcacgctggc cgccgtctcc     360
ctggacaggt atctggccat ccgctacccg ctgcactccc gagagttgcg cacacctcga     420
aacgcgctgg ccgccatcgg gctcatctgg gggctagcac tgctcttctc cgggccctac     480
ctgagctact accgtcagtc gcagctggcc aacctgacag tatgccaccc agcatgggag     540
gcacctcgac gtcgagccat ggacctctgc accttcgtct ttagctacct gctgccagtg     600
```

```
ctagtcctca gtctgaccta tgcgcgtacc ctgcgctacc tctggcgcac agtcgacccg      660
gtgactgcag gctcaggttc ccagcgcgcc aaacgcaagg tgacacggat gatcatcatc      720
gtggcggtgc tttctgcct ctgttggatg ccccaccacg cgcttatcct ctgcgtgtgg       780
tttggtcgct tcccgctcac gcgtgccact acgcgttgc gcatcctttc acacctagtt      840
tcctatgcca actcctgtgt caacccatc gtttacgctc tggtctccaa gcatttccgt      900 aaaggttttcc gcaaaatctg cgcgggcctg ctgcgccctg cccgaggcg agcttcgggc     960 cgagtgagca tcctggcgcc tgggaaccat agtggcagca tgctggaaca ggaatccaca    1020
gacctgacac aggtgagcga ggcagccggg ccccttgtcc caccacccgc acttcccaac    1080
tgcacagcct cgagtagaac cctggatccg gcttgttaa                            1119

<210> SEQ ID NO 6
<211> LENGTH: 1113
<212> TYPE: DNA
<213> ORGANISM: Rat

<400> SEQUENCE: 6
atggctgaca tccagaacat ttcgctggac agcccaggga gcgtaggggc tgtggcagtg       60
cctgtgatct ttgccctcat cttcctgttg gcatggtgg gcaatgggct ggtgttggct      120
gtgctactgc agcctggccc aagtgcctgg caggagccaa gcagtaccac agatctcttc     180
atcctcaact tggccgtggc cgacctttgc ttcatcctgt gctgcgtgcc cttccaggca     240
gccatctaca cactggatgc ctggctcttt ggggctttcg tgtgcaagac ggtacatctg     300
ctcatctacc tcaccatgta tgccagcagc ttcacctgg cggccgtctc cctggacagg     360
tacctggctg tgcggcaccc actgcgctcc agagccctgc gcaccccgcg caacgcgcgc     420
gccgccgtgg ggctcgtgtg gctgctggcg gctctctttt ccgcgcccta cctaagctat     480
tacggcacgg tgcgctacgg cgcgctcgag ctctgcgtgc ccgcttggga ggacgcgcgg     540
cggcgcgcgc tggacgtggc caccttcgcc gcgggctacc tgctgccggt ggccgtggtg     600
agcctggcct acggacgcac gctatgtttc ctatgggccg ccgtgggtcc cgcgggcgcg     660
gcggcagcag aggcgcgcag acgggcgacc ggccgggcgg gacgcgccat gctggcagtg     720
gccgcgctct acgcgctttg ctggggcccg caccacgcgc tcatcctctg cttctggtac     780
ggccgcttcg ccttcagccc ggccacctac gcctgtcgcc tggcctcgca ctgcctcgcc     840
tacgccaact cctgccttaa cccgctcgtc tactcgctcg cctcgcgcca cttccgcgcg     900
cgcttccgcc gcctgtggcc ctgcgccgt cgccgccacc gccaccacca ccgcgctcat     960
cgagccctcc gtcgtgtcca gccggcgtct tcgggcccg ccggttatcc cggcgacgcc    1020
aggcctcgtg gttggagtat ggagcccaga ggggatgctc tgcgtggtgg tggagagact    1080
agactaaccc tgtcccccag gggacctcaa taa                                  1113

<210> SEQ ID NO 7
<211> LENGTH: 29
<212> TYPE: PRT
<213> ORGANISM: Porcine

<400> SEQUENCE: 7

Gly Trp Thr Leu Asn Ser Ala Gly Tyr Leu Leu Gly Pro His Ala Ile
1               5                   10                  15

Asp Asn His Arg Ser Phe His Asp Lys Tyr Gly Leu Ala
            20                  25
```

```
<210> SEQ ID NO 8
<211> LENGTH: 123
<212> TYPE: PRT
<213> ORGANISM: Porcine

<400> SEQUENCE: 8

Met Pro Arg Gly Cys Ala Leu Leu Leu Ala Ser Leu Leu Leu Ala Ser
1               5                   10                  15

Ala Leu Ser Ala Thr Leu Gly Leu Gly Ser Pro Val Lys Glu Lys Arg
            20                  25                  30

Gly Trp Thr Leu Asn Ser Ala Gly Tyr Leu Leu Gly Pro His Ala Ile
        35                  40                  45

Asp Asn His Arg Ser Phe His Asp Lys Tyr Gly Leu Ala Gly Lys Arg
    50                  55                  60

Glu Leu Glu Pro Glu Asp Glu Ala Arg Pro Gly Phe Asp Arg Leu
65                  70                  75                  80

Gln Ser Glu Asp Lys Ala Ile Arg Thr Ile Met Glu Phe Leu Ala Phe
                85                  90                  95

Leu His Leu Lys Glu Ala Gly Ala Leu Gly Arg Leu Pro Gly Leu Pro
            100                 105                 110

Ser Ala Ala Ser Ser Glu Asp Ala Gly Gln Ser
        115                 120

<210> SEQ ID NO 9
<211> LENGTH: 38
<212> TYPE: PRT
<213> ORGANISM: Porcine

<400> SEQUENCE: 9

Leu Gly Ser Pro Val Lys Glu Lys Arg Gly Trp Thr Leu Asn Ser Ala
1               5                   10                  15

Gly Tyr Leu Leu Gly Pro His Ala Ile Asp Asn His Arg Ser Phe His
            20                  25                  30

Asp Lys Tyr Gly Leu Ala
        35

<210> SEQ ID NO 10
<211> LENGTH: 25
<212> TYPE: PRT
<213> ORGANISM: Porcine

<400> SEQUENCE: 10

Asn Ser Ala Gly Tyr Leu Leu Gly Pro His Ala Ile Asp Asn His Arg
1               5                   10                  15

Ser Phe His Asp Lys Tyr Gly Leu Ala
            20                  25

<210> SEQ ID NO 11
<211> LENGTH: 34
<212> TYPE: PRT
<213> ORGANISM: Porcine
<220> FEATURE:
<221> NAME/KEY: PEPTIDE
<222> LOCATION: (28)..(28)
<223> OTHER INFORMATION: Corresponds to ARG(50) of SEQ ID NO.: 29 and
      30.

<400> SEQUENCE: 11

Ala Pro Val His Arg Gly Arg Gly Gly Trp Thr Leu Asn Ser Ala Gly
1               5                   10                  15

Tyr Leu Leu Gly Pro Val Leu His Pro Pro Ser Xaa Ala Glu Gly Gly
```

```
            20                  25                  30

Gly Lys

<210> SEQ ID NO 12
<211> LENGTH: 32
<212> TYPE: PRT
<213> ORGANISM: Porcine
<220> FEATURE:
<221> NAME/KEY: Peptide
<222> LOCATION: (28)..(28)
<223> OTHER INFORMATION: Corresponds to ARG(50) of SEQ ID NO:29 and 30

<400> SEQUENCE: 12

Ala Pro Val His Arg Gly Arg Gly Gly Trp Thr Leu Asn Ser Ala Gly
1               5                   10                  15

Tyr Leu Leu Gly Pro Val Leu His Pro Pro Ser Xaa Ala Glu Gly Gly
            20                  25                  30

<210> SEQ ID NO 13
<211> LENGTH: 9
<212> TYPE: PRT
<213> ORGANISM: Porcine

<400> SEQUENCE: 13

Ala Pro Val His Arg Gly Arg Gly Gly
1               5

<210> SEQ ID NO 14
<211> LENGTH: 6
<212> TYPE: PRT
<213> ORGANISM: Porcine

<400> SEQUENCE: 14

Thr Leu Asn Ser Ala Gly
1               5

<210> SEQ ID NO 15
<211> LENGTH: 27
<212> TYPE: PRT
<213> ORGANISM: Porcine
<220> FEATURE:
<221> NAME/KEY: Peptide
<222> LOCATION: (11)..(11)
<223> OTHER INFORMATION: Corresponds to ARG(50) of SEQ ID NO:29 and 30.

<400> SEQUENCE: 15

Leu Leu Gly Pro Val Leu His Pro Pro Ser Xaa Ala Glu Gly Gly Gly
1               5                   10                  15

Lys Gly Lys Thr Ala Leu Gly Ile Leu Asp Leu
            20                  25

<210> SEQ ID NO 16
<211> LENGTH: 11
<212> TYPE: PRT
<213> ORGANISM: Porcine
<220> FEATURE:
<221> NAME/KEY: Peptide
<222> LOCATION: (1)..(1)
<223> OTHER INFORMATION: Corresponds to ARG(50) of SEQ ID NO:29 and 30.

<400> SEQUENCE: 16

Xaa Ala Ile Asp Gly Leu Pro Tyr Pro Gln Ser
1               5                   10

<210> SEQ ID NO 17
```

```
<211> LENGTH: 44
<212> TYPE: PRT
<213> ORGANISM: Porcine
<220> FEATURE:
<221> NAME/KEY: Peptide
<222> LOCATION: (28)..(28)
<223> OTHER INFORMATION: Corresponds to ARG(50) of SEQ ID NO:29 and 30.

<400> SEQUENCE: 17

Ala Pro Val His Arg Gly Arg Gly Gly Trp Thr Leu Asn Ser Ala Gly
1               5                   10                  15

Tyr Leu Leu Gly Pro Val Leu His Pro Pro Ser Xaa Ala Glu Gly Gly
            20                  25                  30

Gly Lys Gly Lys Thr Ala Leu Gly Ile Leu Asp Leu
        35                  40

<210> SEQ ID NO 18
<211> LENGTH: 27
<212> TYPE: DNA
<213> ORGANISM: Artificial Sequence
<220> FEATURE:
<223> OTHER INFORMATION: Artificial Sequence

<400> SEQUENCE: 18
gtcgacatga atggctccgg cagccag                                        27

<210> SEQ ID NO 19
<211> LENGTH: 32
<212> TYPE: DNA
<213> ORGANISM: Artificial Sequence
<220> FEATURE:
<223> OTHER INFORMATION: Artificial Sequence

<400> SEQUENCE: 19
actagtttaa caagccggat ccagggttct ac                                  32

<210> SEQ ID NO 20
<211> LENGTH: 23
<212> TYPE: DNA
<213> ORGANISM: Artificial Sequence
<220> FEATURE:
<223> OTHER INFORMATION: Artificial Sequence
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (15)..(15)
<223> OTHER INFORMATION: i
<220> FEATURE:
<221> NAME/KEY: variation
<222> LOCATION: (12)..(12)
<223> OTHER INFORMATION: Any base

<400> SEQUENCE: 20
caymgnggnm gnggnggstg gac                                            23

<210> SEQ ID NO 21
<211> LENGTH: 20
<212> TYPE: DNA
<213> ORGANISM: Artificial Sequence
<220> FEATURE:
<223> OTHER INFORMATION: Artificial Sequence
<220> FEATURE:
<221> NAME/KEY: variation
<222> LOCATION: (9)..(9)
<223> OTHER INFORMATION: any base
<220> FEATURE:
```

```
<221> NAME/KEY: variation
<222> LOCATION: (12)..(12)
<223> OTHER INFORMATION: any base

<400> SEQUENCE: 21
gghtggacnc tnaayagygc                                                    20

<210> SEQ ID NO 22
<211> LENGTH: 23
<212> TYPE: DNA
<213> ORGANISM: Artificial Sequence
<220> FEATURE:
<223> OTHER INFORMATION: Artificial Sequence
<220> FEATURE:
<221> NAME/KEY: variation
<222> LOCATION: (6)..(6)
<223> OTHER INFORMATION: any base
<220> FEATURE:
<221> NAME/KEY: variation
<222> LOCATION: (12)..(12)
<223> OTHER INFORMATION: any base
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (18)..(18)
<223> OTHER INFORMATION: i

<400> SEQUENCE: 22
atnccnagng cngtyttncc ytt                                                23

<210> SEQ ID NO 23
<211> LENGTH: 98
<212> TYPE: DNA
<213> ORGANISM: Porcine

<400> SEQUENCE: 23
ggctggactt taaatagtgc tggttacctc ctgggtcccg tactccatcc gccctccagg         60
gctgaaggag gcgggaaggg caaaacagcc ctgggcat                                98

<210> SEQ ID NO 24
<211> LENGTH: 98
<212> TYPE: DNA
<213> ORGANISM: Porcine

<400> SEQUENCE: 24
ggttggactt tgaacagtgc tggttacctc ctgggtcccg tactccatcc gccctccagg         60
gctgaaggag gcgggaaggg caaaaccgcc ctaggcat                                98

<210> SEQ ID NO 25
<211> LENGTH: 20
<212> TYPE: DNA
<213> ORGANISM: Artificial Sequence
<220> FEATURE:
<223> OTHER INFORMATION: Artificial Sequence
<220> FEATURE:
<221> NAME/KEY: variation
<222> LOCATION: (9)..(9)
<223> OTHER INFORMATION: any base
<220> FEATURE:
<221> NAME/KEY: variation
<222> LOCATION: (12)..(12)
<223> OTHER INFORMATION: any base
```

<400> SEQUENCE: 25 gght ggacnc tnaayagygc                                        20

<210> SEQ ID NO 26
<211> LENGTH: 23
<212> TYPE: DNA
<213> ORGANISM: Artificial Sequence
<220> FEATURE:
<223> OTHER INFORMATION: Artificial Sequence

<400> SEQUENCE: 26
atdccbaggg cdgttttgcc ctt                                     23

<210> SEQ ID NO 27
<211> LENGTH: 974
<212> TYPE: DNA
<213> ORGANISM: Porcine

<400> SEQUENCE: 27

```
ttcagcctca agcacccatc cctccagccc tcagatggct ctgactgtcc ctctgatcgt    60
tcttgcagtc ctgctcagcc tgatggagtc tccagcctct gctccggtcc acaggggggcg  120
aggaggctgg accctcaaca gtgctggtta cctcctgggt cccgtactcc atccgccctc   180
cagggctgaa ggaggcggga aggggaagac agccctcggg atcctggacc tgtggaaggc   240
cattgatggg ctcccctatc cccagtctca gttggcctcc aagaggagtc tgggggagac   300
tttcgccaaa ccagactctg gagtaacatt tgttggagtt cctgacgtgg tgccgtggaa   360
acgaatccga ccaggaacta cgaggtttca gatctaggca agctctgcaa gaacgttcca   420
aaggagaaag atgccttgcc gtcatatatg cctccaaact tccgctccaa acttcccccc   480
cgtctccaga tcctcctgaa accctaggta gacaccctct actgagactg ggagcctgaa   540
agtaaatccc caaatcccag gtagaaaatg gggagcattt gaagaattat tctcaaaagt   600
ccccggactg tgccaggttt cactgatccc ccctcccccc ttggactaag tgtaaagcga   660
tgtaaaccaa ctcaagaata attctgaaac cattcaggag atccggagag gaatcgggaa   720
atactcctgc agtgcattta aagtaactgg gtcctatgca acatgagcca ttggatcata   780
caatattgat atcccttcta acacggaggt tctagggtgt ctcagctgga aaagattctt   840
cagagtagca tgcttgcctt accccatcct tctcacccca cccgagcct cctccagcag    900
aaaggacgag aggccatctg gagcagagca gagagaataa atattcccctt tcaaagaaaa  960
aaaaaaaaaa aaaa                                                     974
```

<210> SEQ ID NO 28
<211> LENGTH: 1007
<212> TYPE: DNA
<213> ORGANISM: Porcine

<400> SEQUENCE: 28

```
ggaacgagct ggggagagct gccgactgca ggcagccttc ttcagcctca agcacccatc    60
cctccagccc tcagatggct ctgactgtcc ctctgatcgt tcttgcagtc ctgctcagcc   120
tgatggagtc tccagcctct gctccggtcc acaggggggcg aggaggctgg accctcaaca  180
gtgctggtta cctcctgggt cccgtactcc atccgccctc cagggctgaa ggaggcggga   240
aggggaagac agccctcggg atcctggacc tgtggaaggc cattgatggg ctcccctatc   300
cccagtctca gttggcctcc aagaggagtc tgggggagact ttcgccaaac cagactctgg  360
```

```
agtaacattt gttggagttc ctgacgtggt gccgtggaaa cgaatccgac caggaactac      420
gaggtttcag atctaggcaa gctctgcaag aacgttccaa aggagaaaga tgccttgtcg      480
tcatatatgc ctccaaactt ccgctccaaa cttcccccccc gtccccagat cctcctgaaa     540
ccctaggtag acaccctcta ctgagactgg gagcctgaaa gtaaatcccc aaatcccagg      600
tagaaaatgg ggagcatttg aagaattatt ctcaaaagtc cccggactgt gccaggtttc      660
actgatcccc cccccccccc tccttggact aagtgtaaag cgatgtaaac caactcaaga      720
ataattctga aaccattcag gagatccgga gaggaatcgg gaaatactcc tgcagtgcat      780
ttaaagtaac tgggtcctat gcaacatgag ccattggatc atacaatatt gatatccctt      840
ctaacacgga ggttctaggg tgtctcagct ggaaaagatt cttcagagta gcatgcttgc      900
cttaccccat ccttctcacc ccaccccgag cctcctccag cagaaaggac gagaggccat      960
ctggagcaga gcagagagaa taaatattcc ctttcaaaga aaaaaaa                    1007
```

<210> SEQ ID NO 29
<211> LENGTH: 120
<212> TYPE: PRT
<213> ORGANISM: Porcine

<400> SEQUENCE: 29

```
Met Ala Leu Thr Val Pro Leu Ile Val Leu Ala Val Leu Leu Ser Leu
1               5                   10                  15

Met Glu Ser Pro Ala Ser Ala Pro Val His Arg Gly Arg Gly Gly Trp
                20                  25                  30

Thr Leu Asn Ser Ala Gly Tyr Leu Leu Gly Pro Val Leu His Pro Pro
            35                  40                  45

Ser Arg Ala Glu Gly Gly Gly Lys Gly Lys Thr Ala Leu Gly Ile Leu
        50                  55                  60

Asp Leu Trp Lys Ala Ile Asp Gly Leu Pro Tyr Pro Gln Ser Gln Leu
65                  70                  75                  80

Ala Ser Lys Arg Ser Leu Gly Glu Thr Phe Ala Lys Pro Asp Ser Gly
                85                  90                  95

Val Thr Phe Val Gly Val Pro Asp Val Val Pro Trp Lys Arg Ile Arg
            100                 105                 110

Pro Gly Thr Thr Arg Phe Gln Ile
        115                 120
```

<210> SEQ ID NO 30
<211> LENGTH: 96
<212> TYPE: PRT
<213> ORGANISM: Porcine

<400> SEQUENCE: 30

```
Met Ala Leu Thr Val Pro Leu Ile Val Leu Ala Val Leu Leu Ser Leu
1               5                   10                  15

Met Glu Ser Pro Ala Ser Ala Pro Val His Arg Gly Arg Gly Gly Trp
                20                  25                  30

Thr Leu Asn Ser Ala Gly Tyr Leu Leu Gly Pro Val Leu His Pro Pro
            35                  40                  45

Ser Arg Ala Glu Gly Gly Gly Lys Gly Lys Thr Ala Leu Gly Ile Leu
        50                  55                  60

Asp Leu Trp Lys Ala Ile Asp Gly Leu Pro Tyr Pro Gln Ser Gln Leu
65                  70                  75                  80

Ala Ser Lys Arg Ser Leu Gly Arg Leu Ser Pro Asn Gln Thr Leu Glu
                85                  90                  95
```

<210> SEQ ID NO 31
<211> LENGTH: 60
<212> TYPE: PRT
<213> ORGANISM: Porcine

<400> SEQUENCE: 31

```
Ala Pro Val His Arg Gly Arg Gly Gly Trp Thr Leu Asn Ser Ala Gly
1               5                   10                  15

Tyr Leu Leu Gly Pro Val Leu His Pro Pro Ser Arg Ala Glu Gly Gly
                20                  25                  30

Gly Lys Gly Lys Thr Ala Leu Gly Ile Leu Asp Leu Trp Lys Ala Ile
            35                  40                  45

Asp Gly Leu Pro Tyr Pro Gln Ser Gln Leu Ala Ser
        50                  55                  60
```

<210> SEQ ID NO 32
<211> LENGTH: 180
<212> TYPE: DNA
<213> ORGANISM: Porcine

<400> SEQUENCE: 32

```
gctccggtcc acaggggcg aggaggctgg accctcaaca gtgctggtta cctcctgggt     60
cccgtactcc atccgccctc cagggctgaa ggaggcggga aggggaagac agccctcggg    120
atcctggacc tgtggaaggc cattgatggg ctcccctatc cccagtctca gttggcctcc    180
```

<210> SEQ ID NO 33
<211> LENGTH: 60
<212> TYPE: PRT
<213> ORGANISM: Rat

<400> SEQUENCE: 33

```
Ala Pro Ala His Arg Gly Arg Gly Gly Trp Thr Leu Asn Ser Ala Gly
1               5                   10                  15

Tyr Leu Leu Gly Pro Val Leu His Leu Ser Ser Lys Ala Asn Gln Gly
                20                  25                  30

Arg Lys Thr Asp Ser Ala Leu Glu Ile Leu Asp Leu Trp Lys Ala Ile
            35                  40                  45

Asp Gly Leu Pro Tyr Ser Arg Ser Pro Arg Met Thr
        50                  55                  60
```

<210> SEQ ID NO 34
<211> LENGTH: 60
<212> TYPE: PRT
<213> ORGANISM: Human

<400> SEQUENCE: 34

```
Ala Pro Ala His Arg Gly Arg Gly Gly Trp Thr Leu Asn Ser Ala Gly
1               5                   10                  15

Tyr Leu Leu Gly Pro Val Leu His Leu Pro Gln Met Gly Asp Gln Asp
                20                  25                  30

Gly Lys Arg Glu Thr Ala Leu Glu Ile Leu Asp Leu Trp Lys Ala Ile
            35                  40                  45

Asp Gly Leu Pro Tyr Ser His Pro Pro Gln Pro Ser
        50                  55                  60
```

<210> SEQ ID NO 35
<211> LENGTH: 9
<212> TYPE: PRT

```
<213> ORGANISM: Human, Rat

<400> SEQUENCE: 35

Ala Pro Ala His Arg Gly Arg Gly Gly
1               5

<210> SEQ ID NO 36
<211> LENGTH: 21
<212> TYPE: PRT
<213> ORGANISM: Human, Rat

<400> SEQUENCE: 36

Ala Pro Ala His Arg Gly Arg Gly Gly Trp Thr Leu Asn Ser Ala Gly
1               5                   10                  15

Tyr Leu Leu Gly Pro
            20

<210> SEQ ID NO 37
<211> LENGTH: 123
<212> TYPE: PRT
<213> ORGANISM: Rat

<400> SEQUENCE: 37

Met Pro Cys Phe Ser Ser Arg Met Ala Cys Ser Lys His Leu Val
1               5                   10                  15

Leu Phe Leu Thr Ile Leu Leu Ser Leu Ala Glu Thr Pro Asp Ser Ala
                20                  25                  30

Pro Ala His Arg Gly Arg Gly Gly Trp Thr Leu Asn Ser Ala Gly Tyr
            35                  40                  45

Leu Leu Gly Pro Val Leu His Leu Ser Ser Lys Ala Asn Gln Gly Arg
        50                  55                  60

Lys Thr Asp Ser Ala Leu Glu Ile Leu Asp Leu Trp Lys Ala Ile Asp
65                  70                  75                  80

Gly Leu Pro Tyr Ser Arg Ser Pro Arg Met Thr Lys Arg Ser Met Gly
                85                  90                  95

Glu Thr Phe Val Lys Pro Arg Thr Gly Asp Leu Arg Ile Val Asp Lys
            100                 105                 110

Asn Val Pro Asp Glu Glu Ala Thr Leu Asn Leu
        115                 120

<210> SEQ ID NO 38
<211> LENGTH: 116
<212> TYPE: PRT
<213> ORGANISM: Human

<400> SEQUENCE: 38

Met Ala Pro Pro Ser Val Pro Leu Val Leu Leu Val Leu Leu Leu
1               5                   10                  15

Ser Leu Ala Glu Thr Pro Ala Ser Ala Pro Ala His Arg Gly Arg Gly
                20                  25                  30

Gly Trp Thr Leu Asn Ser Ala Gly Tyr Leu Leu Gly Pro Val Leu His
            35                  40                  45

Leu Pro Gln Met Gly Asp Gln Asp Gly Lys Arg Glu Thr Ala Leu Glu
        50                  55                  60

Ile Leu Asp Leu Trp Lys Ala Ile Asp Gly Leu Pro Tyr Ser His Pro
65                  70                  75                  80

Pro Gln Pro Ser Lys Arg Asn Val Met Glu Thr Phe Ala Lys Pro Glu
                85                  90                  95
```

```
Ile Gly Asp Leu Gly Met Leu Ser Met Lys Ile Pro Lys Glu Glu Asp
            100                 105                 110
Val Leu Lys Ser
        115

<210> SEQ ID NO 39
<211> LENGTH: 180
<212> TYPE: DNA
<213> ORGANISM: Rat

<400> SEQUENCE: 39
gcacctgctc acagggacg aggaggctgg accctcaata gtgctggtta cctcctgggt      60
cctgtcctcc acctttcctc aaaggccaac cagggcagga agacagactc agctcttgag    120
atcctagacc tgtggaaggc catagatggg ctcccttatt cccgctctcc aaggatgacc    180

<210> SEQ ID NO 40
<211> LENGTH: 180
<212> TYPE: DNA
<213> ORGANISM: Human

<400> SEQUENCE: 40
gcacctgccc accggggacg aggaggctgg accctcaata gtgctggcta ccttctgggt    60
cccgtcctcc accttccca atgggtgac caagacggaa agaggagac agcccttgag      120 atcctagacc tgtggaaggc catcgatggg ctcccctact cccaccctcc acagccctcc   180

<210> SEQ ID NO 41
<211> LENGTH: 695
<212> TYPE: DNA
<213> ORGANISM: Rat

<400> SEQUENCE: 41
aggacaactg ggattacaga tgtgcatccc tgcaaccggc tgccacacaa gttctgggat    60
ctgaactcct ggcctcaaac ttgccagcat tccttagctg tatgccgtgc ttttccagtt   120
ccaggatggc ctgctccaag catctggtcc tcttcctcac catcttgcta agcctcgcag    180
aaacaccaga ctctgcacct gctcacaggg gacgaggagg ctggaccctc aatagtgctg    240
gttacctcct gggtcctgtc ctccaccttt cctcaaaggc caaccagggc aggaagacag    300
actcagctct tgagatccta gacctgtgga aggccataga tgggctccct tattcccgct    360
ctccaaggat gaccaaaagg tcaatgggag aaacgtttgt caagccgagg actggagatc    420
tgcgcatagt ggacaagaat gttccggatg aagaagccac cctgaactta tagagagtta    480
gccctagctc actcctacgt ttccagctca ccgcctctcc ccccaccccc gcccccagaa    540
gcgctctgaa caccctttct aagtctaaga ccttacaact atattcccta atctcactaa    600
gacatgttgt gatatttaaa gagttattct gcccagctcc gaaaaaaaaa aaaaaaaaa    660 aagagttatt ctgacgtaaa aaaaaaaaaa aaaaa                               695

<210> SEQ ID NO 42
<211> LENGTH: 473
<212> TYPE: DNA
<213> ORGANISM: Human

<400> SEQUENCE: 42
gaggagccag agagagctgc ggagagctgc cagctgcacc gggcgtgttc cgcagctgta    60
ggcacctgtc gtcctgcctt cgatggctcc tccctccgtc ccctggtcc tcctcctcgt    120 cctcttgctg agcctggcag agactccagc atccgcacct gcccaccggg gacgaggagg   180
```

```
ctggaccctc aatagtgctg gctaccttct gggtcccgtc ctccaccttc cccaaatggg      240
tgaccaagac ggaaagaggg agacagccct tgagatccta gacctgtgga aggccatcga      300
tgggctcccc tactcccacc ctccacagcc ctccaagagg aatgtgatgg agacgtttgc      360
caaaccagag attggagatc tgggcatgct cagcatgaaa attcccaagg aggaagatgt      420
cctgaagtca tagatgtctt caaatccctg ttcctatcct tcttctccag ctc             473
```

<210> SEQ ID NO 43
<211> LENGTH: 30
<212> TYPE: PRT
<213> ORGANISM: Porcine

<400> SEQUENCE: 43

Ala Pro Val His Arg Gly Arg Gly Gly Trp Thr Leu Asn Ser Ala Gly
1               5                   10                  15

Tyr Leu Leu Gly Pro Val Leu His Pro Pro Ser Arg Ala Glu
            20                  25                  30

<210> SEQ ID NO 44
<211> LENGTH: 10
<212> TYPE: PRT
<213> ORGANISM: Porcine

<400> SEQUENCE: 44

Cys Ala Pro Ala His Arg Gly Arg Gly Gly
1               5                   10

<210> SEQ ID NO 45
<211> LENGTH: 356
<212> TYPE: DNA
<213> ORGANISM: Rat

<400> SEQUENCE: 45

```
atggctctga ctgtccctct gatcgttctt gcagtcctgc tcagcctgat ggagtctcca      60
gcctctgctc cggtccacag ggggcgagga ggctggaccc tcaacagtgc tggttacctc     120
ctgggtcccg tactccatcc gccctccagg gctgaaggag gcgggaaggg gaagacagcc     180
ctcgggatcc tggacctgtg gaaggccatt gatgggctcc cctatcccca gtctcagttg     240
gcctccaaga ggagtctggg ggagactttc gccaaaccag actctggagt aacatttgtt     300
ggagttcctg acgtggtgcc gtggaaacga atccgaccag gaactacgag gtttca         356
```

<210> SEQ ID NO 46
<211> LENGTH: 29
<212> TYPE: DNA
<213> ORGANISM: Artificial Sequence
<220> FEATURE:
<223> OTHER INFORMATION: Artificial Sequence

<400> SEQUENCE: 46

```
atggctctga ctgtccctct gatcgttct                                         29
```

<210> SEQ ID NO 47
<211> LENGTH: 29
<212> TYPE: DNA
<213> ORGANISM: Artificial Sequence
<220> FEATURE:
<223> OTHER INFORMATION: Artificial Sequence

<400> SEQUENCE: 47

```
tgaaacctcg tagttcctgg tcggattcg                                         29
```

<210> SEQ ID NO 48
<211> LENGTH: 28
<212> TYPE: DNA
<213> ORGANISM: Artificial Sequence
<220> FEATURE:
<223> OTHER INFORMATION: Artificial Sequence

<400> SEQUENCE: 48
aggctggacc ctcaatagtg ctggttac                                    28

<210> SEQ ID NO 49
<211> LENGTH: 28
<212> TYPE: DNA
<213> ORGANISM: Artificial Sequence
<220> FEATURE:
<223> OTHER INFORMATION: Artificial Sequence

<400> SEQUENCE: 49
ccatctatgg ccttccacag gtctagga                                    28

<210> SEQ ID NO 50
<211> LENGTH: 126
<212> TYPE: DNA
<213> ORGANISM: Human

<400> SEQUENCE: 50
aggctggacc ctcaatagtg ctggttacct tctgggtccc gtcctccacc ttccccaaat    60
gggtgaccaa gacggaaaga gggagacagc ccttgagatc ctagacctgt ggaaggccat   120
agatgg                                                             126

<210> SEQ ID NO 51
<211> LENGTH: 28
<212> TYPE: DNA
<213> ORGANISM: Artificial Sequence
<220> FEATURE:
<223> OTHER INFORMATION: Artificial Sequence

<400> SEQUENCE: 51
caaatgggtg accaagacgg aaagaggg                                    28

<210> SEQ ID NO 52
<211> LENGTH: 28
<212> TYPE: DNA
<213> ORGANISM: Artificial Sequence
<220> FEATURE:
<223> OTHER INFORMATION: Artificial Sequence

<400> SEQUENCE: 52
ggtctaggat ctcaagggct gtctccct                                    28

<210> SEQ ID NO 53
<211> LENGTH: 26
<212> TYPE: DNA
<213> ORGANISM: Artificial Sequence
<220> FEATURE:
<223> OTHER INFORMATION: Artificial Sequence

<400> SEQUENCE: 53
gaggagccag agagagctgc ggagag                                      26

<210> SEQ ID NO 54
<211> LENGTH: 28
<212> TYPE: DNA

```
<213> ORGANISM: Artificial Sequence
<220> FEATURE:
<223> OTHER INFORMATION: Artificial Sequence

<400> SEQUENCE: 54
gagctggaga agaaggatag gaacaggg                                        28

<210> SEQ ID NO 55
<211> LENGTH: 23
<212> TYPE: DNA
<213> ORGANISM: Artificial Sequence
<220> FEATURE:
<223> OTHER INFORMATION: Artificial Sequence

<400> SEQUENCE: 55
agcatatggc tccggtccac agg                                             23

<210> SEQ ID NO 56
<211> LENGTH: 27
<212> TYPE: DNA
<213> ORGANISM: Artificial Sequence
<220> FEATURE:
<223> OTHER INFORMATION: Artificial Sequence

<400> SEQUENCE: 56
ctggatcctc aggaggccaa ctgagac                                         27

<210> SEQ ID NO 57
<211> LENGTH: 21
<212> TYPE: DNA
<213> ORGANISM: Artificial Sequence
<220> FEATURE:
<223> OTHER INFORMATION: Artificial Sequence

<400> SEQUENCE: 57
cagccctcgg catcctggac c                                               21

<210> SEQ ID NO 58
<211> LENGTH: 21
<212> TYPE: DNA
<213> ORGANISM: Artificial Sequence
<220> FEATURE:
<223> OTHER INFORMATION: Artificial Sequence

<400> SEQUENCE: 58
ggtccaggat gccgagggct g                                               21

<210> SEQ ID NO 59
<211> LENGTH: 21
<212> TYPE: DNA
<213> ORGANISM: Artificial Sequence
<220> FEATURE:
<223> OTHER INFORMATION: Artificial Sequence

<400> SEQUENCE: 59
ctagacatat gccagcattg c                                               21

<210> SEQ ID NO 60
<211> LENGTH: 21
<212> TYPE: DNA
<213> ORGANISM: Artificial Sequence
<220> FEATURE:
<223> OTHER INFORMATION: Artificial Sequence

<400> SEQUENCE: 60
tcgggcaatg ctggcatatg t                                               21
```

```
<210> SEQ ID NO 61
<211> LENGTH: 29
<212> TYPE: PRT
<213> ORGANISM: Rat

<400> SEQUENCE: 61

Gly Trp Thr Leu Asn Ser Ala Gly Tyr Leu Leu Gly Pro His Ala Ile
1               5                   10                  15

Asp Asn His Arg Ser Phe Ser Asp Lys His Gly Leu Thr
            20                  25
```

DNA ENCODING GALANIN RECEPTOR ACTIVATING PEPTIDE

RELATED APPLICATIONS

This application is a divisional of U.S. patent application Ser. No. 09/646,078, filed Nov. 10, 2001, now U.S. Pat. No. 7,064,181, which was the National stage of International Application No. PCT/JP99/01482, filed on Mar. 24, 1999.

TECHNICAL FIELD

The present invention relates to a galanin receptor activating factor (ligand peptide and the like).

BACKGROUND ART

A galanin is a physiologically active peptide consisting of 29 amino acid residues found for the first time in a porcine small intestine extract [FEBS Lett., 164, pp 124-128 (1983)], and has been identified in various species other than porcine animals, such as mammalian, avian, reptilian and piscine animals. Those reported for their amino acid sequences are a human galanin (FEBS Lett., 283, pp 189-194 (1991)), a bovine galanin (FEBS Lett., 234, pp 400-406 (1988)), a rat galanin (J. Biol. Chem., 262, pp 16755-16758 (1987)), an ovine galanin (Peptides, 12, pp 855-859 (1991)) and the like, and the 15 amino acid residues from the N terminal are preserved among the species.

Known porcine galanins are a precursor protein consisting of 123 amino acid residues (preprogalanin (1-123); Proc. Natl. Acad. Sci. USA, 83, pp 6287-6291 (1986)), a precursor which is longer than a galanin by 9 residues at the N terminal, namely, preprogalanin (24-61) amide, and a preprogalanin (37-61) amide in which 4 residues at the N terminal of a galanin are deleted (Peptides, 13, pp 1055-1060 (1992)).

Known physiological activities of the galanins are an acetylcholin release inhibiting effect in a hippocampus (Brain Research, 709, pp 81-87 (1996)), a feeding center stimulating effect in a hypothalamus (Obesity Research, 3, pp 5735-5895 (1995)), a pituitary hormone release stimulating effect in a pituitary gland (Neuroscience Letter, 75, pp 49-54 (1987); Endocrinology, 134, pp 529-536 (1994); Peptides, 7, pp 51-53, (1986)), an insulin secretion inhibiting effect in a pancreas (Acta Physiol. Scand., 139, pp 591-596 (1990)) and the like, each of which is believed to be exerted via a galanin receptor.

The galanin receptors are classified into three subtypes (GALR1, GALR2, GALR3), and the genes have been cloned for GALR1 in humans, rats and mice (Proc. Natl. Acad. Sci. USA, 90, pp 3845-3849 (1993); J. Mol. Neurosci., 6. pp 33-41 (1995); FEBS Lett., 411, pp 225-230 (1997)), for GALR2 in rats (FEBS Lett., 405, pp 285-290 (1997); Mol. Pharmacol., 52, pp 337-343 (1997); J. Biol. Chem., 272, pp 24612-24616 (1997) and for GALR3 in rats (J. Biol. Chem., 272, pp 31949-31952 (1997). Each of these three galanin receptors has 7 hydrophobic regions (transmembrane domains) characteristic to a G protein-coupled receptor, and is considered to stimulate an intracellular transmission system via an activation of a G protein.

A galanin was proven to bind a galanin receptor of any of these three subtypes. The binding affinity of a galanin is the highest to GALR1, and then next highest to GALR2 and then GALR3, and the affinity to GALR3 is lower by about 10 times than to GALR1 (J. Biol. Chem., 272, 31949-31952, 1997). A galanin was reported also to induce a cAMP production inhibition in a GALR1-expressing cell (Proc. Natl. Acad. Sci., USA 90, 3845-3849, 1993), to induce a cAMP production inhibition in a GALR2-expressing cell (Mol. Pharmacol., 52, pp 337-343 (1997)), and to induce an enhanced inositol-phosphate metabolism and an increased intracellular calcium ion level (J. Biol. Chem., 272, 24612-24616, 1997).

The only intrinsic agonist to a galanin receptor identified so far is a galanin. There is no report of a utilization of an activating reaction of an agonist-dependent G protein (G protein-coupled receptor protein) in a galanin receptor, for example, $^{35}$S-labeled guanosine-5'-O-3-thiotriphosphate ([$^{35}$S]GTPgS) binding increasing reaction (Methods in Enzymology, 237, pp 3-13 (1994)) or a GTP hydrolozation-promoting reaction (Methods in Enzymology, 237, 13-26, 1994) for the purpose of searching for a ligand of a galanin receptor.

It is desired to discover a novel intrinsic agonist which is different from a galanin in the selectivity for (specificity to) a subtype of the galanin receptors.

DISCLOSURE OF INVENTION

We constructed a galanin receptor GALR2-expressing cell and a galanin receptor GALR1-expressing cell, which were used to establish a convenient assay for determining the agonistic activity to each subtype of the galanin receptors, i.e., a [$^{35}$S]GTPγS binding test. When this assay was used to screen for a GALR2 agonist, it was successful to obtain a novel activation factor whose activation effect on each subtype of the galanin receptors was different from that of a galanin. Furthermore, we also discovered that it is possible, based on the findings described above, to screen for a compound changing binding activity between this novel activation factor and a galanin receptor.

Thus, the present invention relates to:

(1) A peptide comprising an amino acid sequence identical to or substantially identical to an amino acid sequence represented by SEQ ID NO: 35 and having an ability of binding to a receptor protein comprising an amino acid sequence identical to or substantially identical to an amino acid sequence represented by SEQ ID NO: 1, SEQ ID NO: 2 or SEQ ID NO: 3, or a precursor thereof, its amide or ester, or a salt thereof;

(2) A peptide described in Section (1) comprising an amino acid sequence identical to or substantially identical to an amino acid sequence represented by SEQ ID NO: 35 and having an ability of activating a receptor protein comprising an amino acid sequence identical to or substantially identical to an amino acid sequence represented by SEQ ID NO: 1, SEQ ID NO: 2 or SEQ ID NO: 3, or a precursor thereof, its amide or ester, or a salt thereof;

(3) A peptide comprising an amino acid sequence identical to or substantially identical to an amino acid sequence represented by SEQ ID NO: 36, or a precursor thereof, its amide or ester, or a salt thereof;

(4) A peptide described in Section (1) or Section (3) wherein said peptide is a peptide comprising an amino acid sequence identical to or substantially identical to an amino acid sequence represented by SEQ ID NO: 11, 12, 15, 16 or 43, or a precursor thereof, its amide or ester, or a salt thereof;

(5) A peptide described in Section (1) or Section (3) wherein said peptide is a peptide comprising an amino acid sequence identical to or substantially identical to an amino acid sequence represented by SEQ ID NO: 11, 12, 15, 16 or 43 and having a molecular weight of 5000 to 10000, or a precursor thereof, its amide or ester, or a salt thereof;

(6) A peptide described in Section (1) or Section (3) wherein said peptide is a peptide comprising an amino acid sequence identical to or substantially identical to an amino acid sequence represented by SEQ ID NO: 31, 33 or 34, or a precursor thereof, its amide or ester, or a salt thereof;

(7) A precursor of a peptide described in Section (1) or Section (3) wherein said precursor is a peptide comprising an amino acid sequence identical to or substantially identical to an amino acid sequence represented by SEQ ID NO: 29, or its amide or ester, or a salt thereof;

(8) A precursor of a peptide described in Section (6) wherein said substantially identical amino acid sequence is an amino acid sequence represented by SEQ ID NO: 30, 37 or 38, or its amide or ester, or a salt thereof;

(9) A DNA comprising a DNA comprising a base sequence encoding a peptide described in Section (1) or Section (3);

(10) A DNA described in Section (9) encoding a peptide having an amino acid sequence identical to or substantially identical to an amino acid sequence represented by SEQ ID NO: 31, 33 or 34;

(11) A DNA described in Section (10) having a base sequence represented by SEQ ID NO: 32, 39 or 40;

(12) A DNA comprising a DNA comprising a base sequence encoding a precursor of a peptide described in Section (1) or Section (3) having an amino acid sequence identical to or substantially identical to an amino acid sequence represented by SEQ ID NO: 29, 30, 37 or 38;

(13) A DNA described in Section (12) comprising a DNA comprising a base sequence represented by SEQ ID NO: 27, 28, 41 or 42;

(14) A recombinant vector comprising a DNA described in Section (9);

(15) A transformant transformed with a recombinant vector described in Section (14);

(16) A method for producing a peptide described in Section (1) or Section (3) or a precursor thereof, its amide or ester, or a salt thereof, which comprises cultivating the transformant described in Section (15) and producing a peptide described in Section (1) or Section (3);

(17) An antibody to a peptide described in Section (1) or Section (3) or a precursor thereof;

(18) A diagnostic agent comprising an antibody described in Section (17);

(19) A pharmaceutical comprising a peptide described in Section (1) or Section (3) or a precursor thereof, its amide or ester, or a salt thereof;

(20) A pharmaceutical described in Section (19) which is a memory function improving agent, an appetite regulating agent, an uterine function regulating agent, a renal function regulating agent, a prostatic function regulating agent, a testicular function regulating agent or a skeletal muscle function regulating agent;

(21) A method for screening for an agonist or an antagonist to a receptor protein comprising an amino acid sequence identical to or substantially identical to an amino acid sequence represented by SEQ ID NO: 1, 2 or 3, which comprises using a peptide described in Section (1) or Section (3) or a precursor thereof, its amide or ester, or a salt thereof; and,

(22) A compound obtained by a method for screening described in Section (21) or a salt thereof.

BRIEF DESCRIPTION OF DRAWINGS

FIG. 6 shows the comparison of the amino acid sequences between an inventive peptide and a galanin precursor.

FIG. 8 shows a representative screening for a hybridoma after a cell fusion when using a mouse immunized with an Ala-Pro-Ala-His-Arg-Gly-Arg-Gly-Gly-Cys(-NH$_2$)—KLH complex.

BEST MODE FOR CARRYING OUT THE INVENTION

Figure 1:
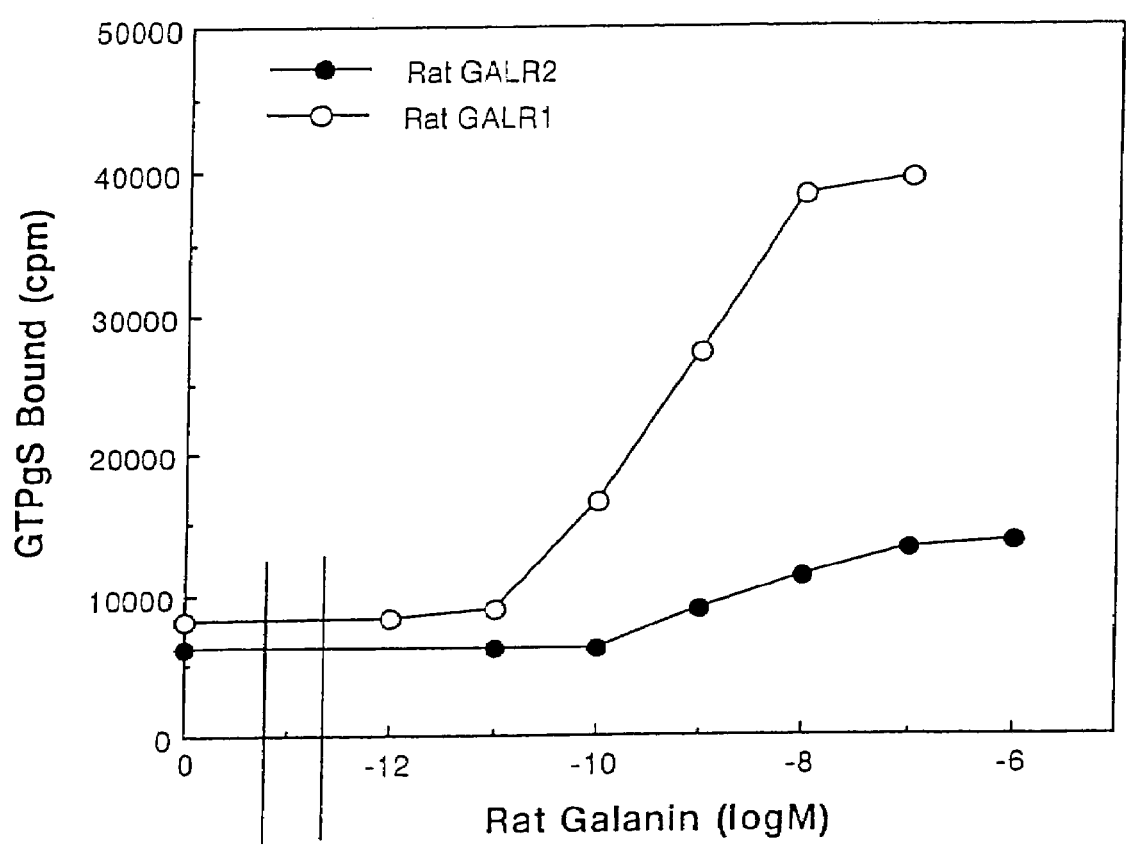
FIG. 1 shows the detected results of the galanin receptor activating effect in a [$^{35}$S]GTPγS binding test.

An expression "substantially identical" referred here means that the activity of a protein, such as a receptor agonist activity, i.e., an ability of activating a receptor possessed by a ligand, a ligand receptor binding activity, is substantially the same. A substitution, deletion, addition or insertion of an amino acid may sometimes cause no substantial change in the physiological and chemical characteristics of a peptide, and, in such case, a protein undergoing such substitution, deletion, addition or insertion can be considered to be substantially identical to a protein undergoing no such substitution, deletion, addition or insertion. A substantially identical substituent for an amino acid in a amino acid sequence may for example be selected from other amino acids in the class to which said amino acid belongs. A non-polar (hydrophobic) amino acid may for example be alanine, leucine, isoleucine, valine, proline, phenylalanine, tryptophan and methionine. A polar (neutral) amino acid may for example be glycine, serine, threonine, cysteine, tyrosine, asparagine and glutamine. A positively-charged (basic) amino acid may for example be arginine, lysine and histidine. A negatively-charged (acidic) amino acid may for example be aspartic acid and glutamic acid.

A peptide according to the invention is a peptide having an ability of binding to a galanin receptor. Preferably, it has a galanin receptor activating effect, and is a ligand peptide other than known galanins. A galanin receptor is defined below.

A peptide according to the invention may for example be a peptide comprising an amino acid sequence identical to or substantially identical to an amino acid sequence represented by SEQ ID NO: 35 (e.g., SEQ ID NO: 13) and having an ability of binding to a receptor protein comprising an amino acid sequence identical to or substantially identical to an amino acid sequence represented by SEQ ID NO: 1, SEQ ID NO: 2 or SEQ ID NO: 3 (preferably an ability of activating a receptor protein), typically including:

(I) A peptide comprising an amino acid sequence identical to or substantially identical to an amino acid sequence represented by SEQ ID NO: 35 (e.g., SEQ ID NO: 13), and also comprising an amino acid sequence identical to or substantially identical to an amino acid sequence represented by SEQ ID NO: 11, 12, 15, 16 or 43, and having an ability of binding to a receptor protein comprising an amino acid sequence identical to or substantially identical to an amino acid sequence represented by SEQ ID NO: 1, SEQ ID NO: 2 or SEQ ID NO: 3 (preferably an ability of activating a receptor protein);

(II) A peptide described in Section (I) having a molecular weight of 5000 to 10000;

(III) A peptide described in Section (I) having a molecular weight of 5000 to 8000;

(IV) A peptide comprising an amino acid sequence identical to or substantially identical to an amino acid sequence represented by SEQ ID NO: 17, and having an ability of binding to a receptor protein comprising an amino acid sequence identical to or substantially identical to an amino acid sequence represented by SEQ ID NO: 1, SEQ ID NO: 2 or SEQ ID NO: 3 (preferably an ability of activating a receptor protein), and also having a molecular weight of 5000 to 10000; and, (V) A peptide comprising an amino acid sequence identical to or substantially identical to an amino acid sequence represented by SEQ ID NO: 31, SEQ ID NO: 33 or SEQ ID NO: 34, and having an ability of binding to a receptor protein comprising an amino acid sequence identical to or substantially identical to an amino acid sequence represented by SEQ ID NO: 1, SEQ ID NO: 2 or SEQ ID NO: 3 (preferably an ability of activating a receptor protein).

Furthermore, a peptide according to the invention includes:

(VI) A peptide comprising an amino acid sequence identical to or substantially identical to an amino acid sequence represented by SEQ ID NO: 36;

(VII) A peptide described in Section (VI) comprising an amino acid sequence identical to or substantially identical to an amino acid sequence represented by SEQ ID NO: 11, SEQ ID NO: 12, SEQ ID NO: 15, SEQ ID NO: 16 or SEQ ID NO: 43;

(VIII) A peptide described in Section (VII) having a molecular weight of 5000 to 10000;

(IX) A peptide described in Section (VII) having a molecular weight of 5000 to 8000;

(X) A peptide comprising an amino acid sequence identical to or substantially identical to an amino acid sequence represented by SEQ ID NO: 31, SEQ ID NO: 33 or SEQ ID NO: 34;

(XI) A peptide comprising an amino acid sequence identical to or substantially identical to an amino acid sequence represented by SEQ ID NO: 17;

(XII) A peptide comprising an amino acid sequence identical to or substantially identical to an amino acid sequence represented by SEQ ID NO: 35 (e.g., SEQ ID NO: 13), and also comprising an amino acid sequence identical to or substantially identical to an amino acid sequence represented by SEQ ID NO: 11, SEQ ID NO: 12, SEQ ID NO: 15, SEQ ID NO: 16 or SEQ ID NO: 43;

(XIII) A peptide described in Sections (X) to (XII) having a molecular weight of 5000 to 10000.

A peptide of the invention, a method for producing the same and a use thereof are detailed below.

While a peptide of the invention may be derived from an origin which is not particularly limited, it may be derived from a tissue (for example pituitary gland, pancreas, brain, kidneys, liver, reproductive glands, thyroidal gland, gall bladder, bone marrow, adrenal gland, skin, muscle, lungs, digestive tracts, blood vessels, heart, testes and the like) or a cell of a human or a warm-blooded animal (for example guinea pig, rat, mouse as well as porcine, ovine, bovine and simian animals) or a cell (preferably those derived from mouse brain, rat brain, porcine brain, bovine brain, porcine hypothalamus, bovine hypothalamus, porcine lung, bovine lung, bovine stomach, human hypothalamus, porcine testis, bovine testis, rat testis, human testis or human lung) or may be a synthetic peptide.

For example, a peptide of the invention may be:

[1] in addition to a peptide comprising an amino acid sequence identical to or substantially identical to an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34), a peptide having an activity whose quality is substantially analogous to a peptide comprising an amino acid sequence having a homology of about 50 to 99.9% (preferably 70 to 99.9%, more preferably 80 to 99.9%, further preferably 90 to 99.9%, most preferably 95 to 99.9%) with an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) (except for the sequence of a galanin represented by SEQ ID NO: 7, 8, 9 or 10 or a precursor thereof).

As "an activity whose quality is substantially analogous" is meant an analogous quality in terms of a galanin receptors GALR1, GALR2 or GALR3-binding activity, galanin receptors GALR1, GALR2 or GALR3-activating activity, and an ability of activating an accompanying signal transmission cascade, such as arachidonic acid release, intracellular $Ca^{2+}$ release, intracellular cAMP production inhibition, inositol phosphoric acid production (inhibition), cell membrane potential variation, intracellular protein phosphorylation, intracellular pH variation and the like. Accordingly, the quantitative factors of this activity, such as the potency or the molecular weight, may be different.

Typical examples of a peptide of the invention are listed below (except for a galanin having an amino acid sequence represented by SEQ ID NO: 7, 8, 9 or 10 or a precursor thereof).

(I) A peptide derived from mouse brain, rat brain, porcine brain, bovine brain, porcine hypothalamus, bovine hypothalamus, porcine lung, bovine lung, bovine stomach, human hypothalamus, porcine testis, bovine testis, rat testis, human testis or human lung comprising an amino acid sequence represented by an amino acid sequence identical to or substantially identical to an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof.

(II) A peptide comprising an amino acid sequence formed as a result of the substitution, deletion, addition or insertion of one or more amino acids in a peptide comprising an amino acid sequence identical to or substantially identical to an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof can be exemplified as a peptide comprising a substantially identical amino acid sequence. For example, a peptide comprising (1) an amino acid sequence formed as a result of the deletion of 1 to 7, preferably 1 to 5, more preferably 1 to 3 amino acids in an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof, (2) an amino acid sequence formed as a result of the addition (or insertion) of 1 to 20, preferably 1 to 15, more preferably 1 to 10 amino acids to an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof, (3) an amino acid sequence formed as a result of the substitution of 1 to 7, preferably 1 to 5, more preferably 1 to 3 amino acids in an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof with other amino acids.

"An amino acid whose quality is substantially analogous" means an amino acid having a homology therewith ranging from 70 to 99.9%, preferably 80 to 99.9%, more preferably 90 to 99.9%, most preferably 95 to 99.9%.

The molecular weight of a peptide of the invention, when determined by a gel filtration chromatography or an equivalent method, ranges from about 5000 to about 10000 Dalton, preferably about 5000 to about 8000 Dalton, more preferably about 5500 to about 8000 Dalton, most preferably about 6000 to about 7000 Dalton.

A peptide referred to herein has an N terminal (amino terminal) on its left end and a C terminal (carboxyl terminal) on its right end in accordance with customary peptide designations.

While a peptide of the invention has a C terminal which is usually a carboxyl group (—COOH) or a carboxylate (—COO⁻), it may also have as a C terminal which is an amide (—CONH$_2$) or an ester (—COOR). R in an ester may for example be a $C_{1-6}$ alkyl group such as methyl, ethyl, n-propyl, isopropyl and n-butyl, a $C_{3-8}$ cycloalkyl group such as cyclopentyl and cyclohexyl, a $C_{6-12}$ aryl group such as phenyl and a-naphthyl, a phenyl-$C_{1-2}$ alkyl such as benzyl, phenethyl and benzhydryl, or a $C_{7-14}$ aralkyl group such as an α-naphthyl-$C_{1-2}$-alkyl such as α-naphthylmethyl, as well as a pivaloyloxymethyl group employed frequently for the ester forms for an oral administration.

When a peptide of the invention has a carboxyl group or a carboxylate anywhere other than its C terminal, it is also regarded as a peptide of the invention if such group is derivatized to an amido or an ester. In such case, the ester may be an ester similar to that exemplified above as an ester at the C terminal.

While a salt of a peptide of the invention may be a salt with a physiologically acceptable base (e.g., an alkaline metal) or acid (organic or inorganic acid), a physiologically acceptable acid addition salt is particularly preferred. Such salt may for example be a salt with an inorganic acid (e.g., hydrochloric acid, phosphoric acid, hydrobromic acid, sulfuric acid) or a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

A peptide of the invention may be produced by a method for isolating a peptide as purified from a tissue or a cell of a human or a warm-blooded animal, or may be produced in accordance with a peptide synthesis described below.

A peptide of the invention may be produced also by incubating a transformant comprising a DNA encoding this peptide. Such DNA encoding this peptide can be prepared in accordance with a known cloning method (for example, a method described in Molecular Cloning, 2nd ed., J. Sambrook et al., Cold Spring Harbor Lab. Press, 1989).

Such cloning method may for example be (1) a method in which a transformant comprising a DNA encoding an intended peptide is obtained from a cDNA library by a hybridization using a DNA probe or a DNA primer designed based on the amino acid sequence of this peptide, or (2) a method in which a transformant comprising a DNA encoding an intended peptide is obtained by a PCR using a DNA primer designed based on the amino acid sequence of this peptide.

For producing a peptide of the invention from a tissue or a cell of a human or a warm-blooded animal, such tissue or cell of a human or a warm-blooded animal is homogenized and extracted with an acid or an alcohol, and the extract obtained is purified by a combination of salting out, dialysis, gel filtration and chromatographic methods such as reverse phase, ion exchange and affinity chromatographies.

As described above, a peptide of the invention can be produced (1) in accordance with a peptide synthesis method known per se, or (2) by cleaving a peptide comprising the peptide of the invention with a suitable peptidase.

A peptide synthesis method may for example be a solid phase synthesis or a liquid phase synthesis. Thus, a partial peptide or an amino acid capable of constituting a peptide of the invention and the remainder region are condensed and a protective group, if any, is then removed, whereby yielding an intended peptide. Known condensation and deprotection methods are those described in [1] and [2] shown below.

[1] M. Bodanszky and M. A. Ondetti, Peptide Synthesis, Interscience Publishers, New York (1966)

[2] Schroeder and Luebke, The Peptide, Academic Press, New York (1965)

After a reaction, ordinary purification methods such as extraction with a solvent, distillation, column chromatography, liquid chromatography and recrystallization may be employed in combination to isolate a pure peptide of the invention. A peptide obtained by the method described above as a free form can be converted into a suitable salt by a known method, and the peptide obtained as a salt can be converted into a free form by a known method.

For an amide form of a peptide of the invention, a commercially available resin for a peptide synthesis which is suitable for an amide formation can be employed. Such resin may for example be a chloromethyl resin, a hydroxymethyl resin, a benzhydrylamine resin, an aminomethyl resin, a 4-benzyloxybenzylalcohol resin, a 4-methylbenzhydrylamine resin, a PAM resin, a 4-hydroxymethylmethylphenylacetoamidemethyl resin, a polyacrylamide resin, a 4-(2', 4'-dimethoxyphenyl-hydroxymethyl)phenoxy resin, a 4-(2', 4'-dimethoxyphenyl-Fmoc aminoethyl)phenoxy resin and the like. Using any of these resins, an amino acid whose α-amino group and side chain functionality are protected appropriately is condensed in the order giving the sequence of an intended peptide on the resin in accordance with a condensation method known per se. At the end of the reaction, a peptide is cut out from the resin at the same time with the deprotection, and then an intramolecular disulfide bond is formed if necessary, whereby yielding the intended peptide.

While the condensation of a protected amino acid described above may be performed using various activating agents employed in a peptide synthesis, a carbodiimide is preferred. A carbodiimide may for example be DCC, N,N'-diisopropylcarbodiimide, N-ethyl-N'-(3-dimethylaminopropyl)carbodiimide and the like. For the activation with any of these compounds, a protected amino acid may be added together with a racemization inhibitor (e.g., HOBt, HOOBt, etc) directly to a resin, or an amino acid which has previously been protected in the form of a symmetric anhydride, HOBt ester or HOOBt ester is first activated and then added to a resin. A solvent used for the activation of a protected amino acid or for the condensation with a resin may be selected appropriately from the solvents which are known to be applicable to a peptide condensation reaction. For example, an acid amide such as N,N-dimethylformamide, N,N-dimethylacetoamide and N-methylpyrrolidone, a halogenated hydrocarbon such as methylene chloride and chloroform, an alcohol such as trifluoroethanol, a sulfoxide such as dimethylsulfoxide, a tertiary amine such as pyridine, an ether such as dioxane and tetrahydrofuran, a nitrile such as acetonitrile and propionitrile, an ester such as methyl acetate and ethyl acetate and a mixture thereof can be employed. The reaction temperature is within the range known to be applicable to a peptide bond formation, and usually about −20° C. to about 50° C. An activated amino acid derivative is used usually in an amount of about 1.5 to about 4-fold excess. When a ninhydrin test indicated an insufficient condensation, the condensation may be repeated without any deprotection to ensure a complete condensation. When no complete condensation is achieved even after repetitive condensation steps, acetic anhydride or acetylimidazol is used to acetylate an unreacted amino acid to avoid any interference with the subsequent reactions.

A protective group for an amino group in a starting amino acid may for example be Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc and the like. A protective group for a carboxyl group may for example be any of those exemplified above as R, such as a $C_{1-6}$ alkyl group, a $C_{3-8}$ cycloalkyl group and a $C_{7-14}$ aralkyl group, as well as 2-adamantyl, 4-nitrobenzyl, 4-mehtoxybenzyl, 4-chlorobenzyl, phenacyl group and benzyloxycarbonyl hydrazide, t-butoxycarbonyl hydrazide, trityl hydrazide and the like.

The hydroxyl group of serine and threonine can be protected by an esterification or an etherification. A group suitable for such esterification may for example be a lower $(C_{1-6})$alkanoyl group such as an acetyl group, an aroyl group such as a benzoyl group, and a group derived from a carbonate such as a benzyloxycarbonyl group and an ethoxycarbonyl group. A group suitable for the etherification may for example be a benzyl group, a tetrahydropyranyl group and a t-butyl group.

A protective group for a phenolic hydroxyl group of tyrosine may for example be Bzl, $Cl_2$-Bzl, 2-nitrobenzyl, Br-Z, t-butyl and the like.

A protective group for imidazole of histidine may for example be Tos, 4-mehtoxy-2,3,6-trimethylbenzenesulfonyl, DNP, benzyloxymethyl, Bum, Boc, Trt, Fmoc and the like.

A starting material whose carboxyl group is activated may for example be a corresponding acid anhydride, an azide, an activated ester [an ester with an alcohol (e.g., pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt)] and the like. A starting material whose amino group is activated may for example be a corresponding phosphoryl amide.

A method for removing (cleaving) a protective group may for example be a catalytic hydrogenation under a hydrogen flow in the presence of a catalyst such as a Pd black or a Pd/C, an acid treatment with anhydrous hydrogen fluoride, methanesulfonic acid, trifluoromethanesulfonic acid, trifluoroacetic acid or a mixture thereof, a base treatment with diisopropylethylamine, triethylamine, piperidine, piperazine and the like, as well as a reduction with sodium in an aqueous ammonia. The cleavage by an acid treatment described above is performed usually at a temperature of −20° C. to 40° C., effectively with an addition of a cation scavenger such as anisol, phenol, thioanisol, m-cresol, p-cresol, dimethyl sulfide, 1,4-butanedithiol, 1,2-ethanedithiol and the like. A 2,4-dinitrophenyl group used as a protective group for imidazole of histidine can be cleaved by a treatment with thiophenol, and a formyl group used as a protective group for indol of tryptophan can be cleaved by a treatment with an alkali such as a dilute sodium hydroxide and a dilute ammonia, in addition to a deprotection method by an acid treatment in the presence of 1,2-ethanedithiol and 1,4-butandithiol as described above.

The method and the group for protecting a functional group which should not be involved in the reaction of a starting material, the deprotection and the activation of a group to be involved in the reaction may be selected appropriately from known groups and known means.

Another method for obtaining an amide form of a peptide of the invention involves amidating an α-carboxyl group of the amino acid at the carboxyl terminal, extending the peptide chain in the direction of the amino group until a desired length is obtained, forming a peptide having no protective group of the α-amino group at the N-terminal of the peptide chain and a peptide (amino acid) having no protective group of the carboxyl group at the C-terminal, and then condensing these two peptides in a solvent mixture described above. The conditions of the condensation are as described above. After purifying the protected peptide obtained by the condensation, all protective groups are cleaved by the methods described above to obtain an intended crude peptide. This crude peptide is subjected to various purification means and a desired fraction is lyophilized to obtain an amide form of the intended peptide.

For an ester form of a peptide of the invention, an α-carboxyl group of the amino acid at the carboxyl terminal is condensed with an appropriate alcohol to form an amino acid ester, and then subjected to a procedure for an amide form of the peptide to obtain an ester form of the intended peptide.

A peptide of the invention may be any one provided that it has an activity similar to that of a peptide comprising an amino acid sequence identical to or substantially identical to an amino acid sequence (for example, GALR1 agonist activity, GALR2 agonist activity or GALR3 agonist activity, etc.) represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof. Such peptide may for example be a peptide having an amino acid sequence formed as a result of the deletion, addition (insertion) or substitution of 1 to 5 amino acids in an amino acid sequence represented by SEQ ID NO: 17, SEQ ID NO: 31, SEQ ID NO: 33 or SEQ ID NO: 34 (preferably SEQ ID NO: 31, SEQ ID NO: 33 or SEQ ID NO: 34) or a partial sequence thereof.

A precursor of a peptide of the invention may be any peptide which encodes as its partial sequence a ligand peptide of the invention (except for a galanin having an amino acid sequence represented by SEQ ID NO: 7, 8, 9 or 10 or a precursor thereof).

Typically, a precursor of a peptide of the invention may for example be a peptide (or polypeptide) having an amino acid sequence identical to or substantially identical to an amino acid represented by SEQ ID NO: 29.

In this context, "a substantially identical amino acid sequence" may for example be an amino acid sequence having a homology of 70 to 99.9%, more preferably 80 to 99.9%, further preferably 90 to 99.9%, most preferably 95 to 99.9% with an amino acid sequence represented by SEQ ID NO: 29.

Furthermore, "a substantially identical amino acid sequence" may for example be (i) an amino acid sequence formed as a result of the substitution of 1 to 7, preferably 1 to 5, more preferably 1 to 3 amino acids in an amino acid sequence represented by SEQ ID NO: 29 with other amino acids, (ii) an amino acid sequence formed as a result of the deletion of 1 to 7, preferably 1 to 5, more preferably 1 to 3 amino acids in an amino acid sequence represented by SEQ ID NO: 29, (iii) an amino acid sequence formed as a result of the addition (or insertion) of 1 to 7, preferably 1 to 5, more preferably 1 to 3 amino acids to an amino acid sequence represented by SEQ ID NO: 29. The position of the "substitution, deletion, addition (or insertion)" is not particularly limited as long as it is outside of the region which encodes as its partial sequence a ligand peptide of the invention.

Typically, a peptide (or polypeptide) comprising an amino acid sequence identical to or substantially identical to an amino acid represented by SEQ ID NO: 29 may for example be:

(1) a peptide (or polypeptide) comprising an amino acid sequence identical to or substantially identical to an amino acid represented by SEQ ID NO: 30;
(2) a peptide (or polypeptide) comprising an amino acid sequence identical to or substantially identical to an amino acid represented by SEQ ID NO: 37; or,
(3) a peptide (or polypeptide) comprising an amino acid sequence identical to or substantially identical to an amino acid represented by SEQ ID NO: 38.

A peptide of the invention can be used as an antigen for preparing an anti-ligand peptide antibody. A peptide as such antigen may be a peptide of the invention described above, as well as a partial peptide of a peptide of the invention described above, such as an N-terminal peptide, a C-terminal peptide and a middle-positioned peptide.

A partial peptide may be a peptide containing a single domain of an inventive peptide or a peptide containing two or more domain at the same time.

Since a partial peptide described above may be acceptable when it can be used as an antigen for preparing an anti-ligand peptide antibody, it may also be (i) a partial peptide formed as a result of the addition (or insertion) of 1 to several (preferably 1 to 3, more preferably 1 or 2) other amino acid residues to a partial peptide such as an N-terminal peptide, a C-terminal peptide and a middle-positioned peptide of a peptide of the invention described above, (ii) a partial peptide formed as a result of the deletion of 1 to several (preferably 1 to 3, more preferably 1 or 2) amino acid residues from a partial peptide such as an N-terminal peptide, a C-terminal peptide and a middle-positioned peptide of a peptide of the invention described above, (iii) a partial peptide formed as a result of the substitution of 1 to several (preferably 1 to 3, more preferably 1 or 2) constituent amino acid residues in a partial peptide such as an N-terminal peptide, a C-terminal peptide and a middle-positioned peptide of a peptide of the invention described above with other amino acid residues.

Such partial peptide is typically a peptide consisting of an amino acid sequence represented by [1] Ala Pro Ala His Arg Gly Arg Gly Gly Cys-NH$_2$ (amide form of SEQ ID NO: 44) employed in Example 9 described below, as well as:

[2] a peptide consisting of an amino acid sequence represented by SEQ ID NO: 11;
[3] a peptide consisting of an amino acid sequence represented by SEQ ID NO: 12;
[4] a peptide consisting of an amino acid sequence represented by SEQ ID NO: 13;
[5] a peptide consisting of an amino acid sequence represented by SEQ ID NO: 15;
[6] a peptide consisting of an amino acid sequence represented by SEQ ID NO: 16;
[7] a peptide consisting of an amino acid sequence represented by SEQ ID NO: 17;
[8] a peptide consisting of an amino acid sequence represented by SEQ ID NO: 35;
[9] a peptide consisting of an amino acid sequence represented by SEQ ID NO: 36; and,
[10] a peptide consisting of an amino acid sequence represented by SEQ ID NO: 43.

A partial peptide referred herein may also have an amide (—CONH$_2$) or an ester (—COOR) at its C-terminal. An ester group employed here may for example be one exemplified in conjunction with a peptide described above. When such partial peptide has a carboxyl group or a carboxylate anywhere other than its C terminal, it is also regarded as a partial peptide of the invention if such group is derivatized to an amido or an ester. In such case, the ester may be an ester similar to that exemplified above as an ester at the C terminal.

A partial peptide of an inventive peptide itself may have an activity which is possessed by the inventive peptide (for example, a galanin receptor activating effect).

A partial peptide of an inventive peptide itself may also be a fusion peptide with a protein whose function or characteristics are well known.

Such fusion protein may typically be a fusion peptide between a peptide consisting of an amino acid sequence represented by Ala Pro Ala His Arg Gly Arg Gly Gly Cys-NH$_2$ (amide form of SEQ ID NO: 44) employed in Example 11 described below and a Keyhole Limpet Hemocyanin (KLH).

A salt of a partial protein of a peptide of the invention may be similar to a salt of a peptide described above.

An amide, ester or salt of a partial peptide of a peptide of the invention may be produced in accordance with a synthesis of described above, or by cleaving a peptide of the invention with a suitable peptidase.

A DNA encoding a peptide of the invention may be any DNA comprising a DNA comprising a base sequence encoding (I) a peptide comprising an amino acid sequence identical to or substantially identical to an amino acid sequence represented by SEQ ID NO: 35 (e.g., SEQ ID NO: 13) and having an ability of binding to a receptor protein comprising an amino acid sequence identical to or substantially identical to an amino acid sequence represented by SEQ ID NO: 1, SEQ ID NO: 2 or SEQ ID NO: 3 (preferably an ability of activating a receptor protein), or (II) a peptide comprising an amino acid sequence identical to or substantially identical to an amino acid sequence represented by SEQ ID NO: 36.

A DNA comprising a DNA comprising a base sequence encoding a peptide of the invention specified above may also be employed.

Furthermore, a genome DNA, a genome DNA library, a cDNA derived from a tissue or cell described above, a cDNA library derived from a tissue or cell described above and a synthetic DNA may also be employed. A vector used in a library may be a bacteriophage, a plasmid, a cosmid or a phagemid and the like. A direct amplification from an RNA fraction prepared from a tissue or cell described above may also be performed by a reverse transcriptase polymerase chain reaction (hereinafter referred to as RT-PCR).

More typically, those which can be employed are: (1) a DNA comprising a DNA comprising a base sequence encoding a peptide comprising an amino acid sequence identical to or substantially identical to an amino acid sequence represented by SEQ ID NO: 31, SEQ ID NO: 33 or SEQ ID NO: 34, (2) a DNA derived from a mammal capable of being hybridized with a sequence specified in (1) under a stringent condition, and (3) a DNA which is not capable of being hybridized with a sequence specified in (1) or (2) due to a degeneracy of a gene code but encodes a polypeptide having an identical amino acid sequence. A hybridization can be performed by a method known per se or an analogous method. A stringent condition described above may be established for example at 42° C. with 50% formamide, 4×SSPE (1×SSPE=150 mM NaCl, 10 mM NaH$_2$PO$_4$·H$_2$O, 1 mM EDTA, pH 7.4), 5× Denhart solution and 0.1% SDS.

A DNA comprising a DNA comprising a base sequence encoding a peptide comprising an amino acid sequence identical to or substantially identical to an amino acid sequence represented by SEQ ID NO: 31 may typically be a DNA comprising a DNA comprising a base sequence represented by SEQ ID NO: 32, a DNA comprising a DNA comprising a base sequence encoding a peptide comprising an amino acid sequence identical to or substantially identical to an amino acid sequence represented by SEQ ID NO: 33 may typically be a DNA comprising a DNA comprising a base sequence represented by SEQ ID NO: 39, and a DNA comprising a DNA comprising a base sequence encoding a peptide comprising an amino acid sequence identical to or substantially identical to an amino acid sequence represented by SEQ ID NO: 34 may typically be a DNA comprising a DNA comprising a base sequence represented by SEQ ID NO: 40. Among DNAs encoding inventive peptides or the partial peptides thereof, a DNA fragment comprising 6 to 51 (preferably 9 to 30, more preferably 12 to 30) of partial base sequences is employed preferably also as a probe for a DNA detection.

A DNA encoding a precursor of a peptide of the invention may for example be a DNA comprising a DNA comprising a base sequence encoding a peptide (polypeptide) comprising an amino acid sequence identical to or substantially identical to an amino acid sequence represented by SEQ ID NO: 29 (for example, an amino acid sequence represented by SEQ ID NO: 30, SEQ ID NO: 37 or SEQ ID NO: 38).

A DNA comprising a DNA comprising a base sequence encoding a peptide (polypeptide) comprising an amino acid sequence identical to or substantially identical to an amino acid sequence represented by SEQ ID NO: 29 may typically be a DNA comprising a. DNA comprising a base sequence represented by SEQ ID NO: 27, a DNA comprising a DNA comprising a base sequence encoding a peptide comprising an amino acid sequence identical to or substantially identical to an amino acid sequence represented by SEQ ID NO: 30 may typically be a DNA comprising a DNA comprising a base sequence represented by SEQ ID NO: 28, a DNA comprising a DNA comprising a base sequence encoding a peptide comprising an amino acid sequence identical to or substantially identical to an amino acid sequence represented by SEQ ID NO: 37 may typically be a DNA comprising a DNA comprising a base sequence represented by SEQ ID NO: 41, and a DNA comprising a DNA comprising a base sequence encoding a peptide comprising an amino acid sequence identical to or substantially identical to an amino acid sequence represented by SEQ ID NO: 38 may typically be a DNA comprising a DNA comprising a base sequence represented by SEQ ID NO: 42.

A DNA encoding a peptide of the invention or equivalent can be produced also by the following gene engineering technology. Such gene engineering technology may for example be a method described in Molecular Cloning (2nd ed., J. Sambrook et al., Cold Spring Harbor Lab. Press, 1989). When a commercially available library or kit is employed, an attached instruction may be followed.

A DNA encoding a peptide of the invention or equivalent can be screened by a hybridization of a labeled probe obtained by synthesizing a DNA fragment based on the amino acid sequence of the peptide or a part thereof with a genome DNA or a cDNA library.

In a procedure for cloning a DNA encoding entirely a peptide of the invention or equivalent, a synthetic DNA primer having a partial base sequence of a peptide of the invention is used to perform a PCR known per se to amplify an intended DNA from a genome DNA or a cDNA library, or a hybridization with a DNA integrated into a suitable vector which is labeled with a DNA fragment or a synthetic DNA having a part or all of a peptide of the invention is performed, whereby achieving a screening.

A DNA encoding a cloned peptide of the invention may be used as it is, or after being digested with a restriction enzyme if necessary or after being bound to a linker. Such DNA has an ATG as a translation initiation codon on the side of the 5' terminal and may have a TAA, TGA or TAG as a translation termination codon on the side of the 3' terminal. Such translation initiation and termination codons may be added using a suitable synthetic DNA adapter.

An expression vector for a peptide of the invention may be produced, for example, by (a) cutting an intended DNA fragment out of a DNA encoding the peptide of the invention, followed by (b) ligating the DNA fragment thus obtained to the downstream of the promoter in a suitable expression vector.

A vector may be a *E. coli*-derived plasmid (e.g., pBR322, pBR325, pUC12, pUC13), a *Bacillus subtilis*-derived plasmid (e.g., pUB110, pTP5, pC194), a yeast-derived plasmid (e.g., pSH19, pSH15), a bacteriophage such as λ phage, as well as an animal virus such as retrovirus, vaccinia virus, vaculovirus and the like.

A promoter employed in this invention may be any promoter which corresponds to and is suitable for a host employed for expressing a gene.

When the host cell to be transformed is an animal cell, a promoter which can be employed is an SV 40-derived promoter, a retrovirus promoter, a metallothioneine promoter, a heat shock promoter, a cytomegalovirus promoter, an SRα promoter and the like. Those preferred are a trp promoter, a T7 promoter, a lac promoter, a recA promoter, a λPL promoter, an l pp promoter and the like when the host cell is an *Escherichia* microorganism, an SPO1 promoter, an SPO2 promoter, a penP promoter and the like when the host cell is a *Bacillus* microorganism, and a PHO5 promoter, a PGK promoter, a GAP promoter, an ADH1 promoter, a GAL promoter and the like when the host cell is an yeast. When the host cell is an insect cell, those employed preferably are a polyhedrin promoter, a p10 promoter and the like.

In addition to those described above, an expression vector may also be one optionally containing an enhancer, a splicing signal, a poly-A addition signal, a selection marker, an SV40 replication origin (hereinafter referred to as SV40ori) and the like. A selection marker may for example be a dihydrofolate reductase (hereinafter referred to as dhfr) gene [methotrexate (MTX) resistant], an ampicillin resistant gene (hereinafter referred to as Amp$^r$), a neomycin resistant gene (hereinafter referred to as Neo, G418 resistant) and the like. A-selection is possible also in a thymidine-free medium especially when a DHFR gene is used as a selection marker in CHO (dhfr$^-$) cells.

If necessary, a signal sequence suitable to a host is added to the side of the N terminal of a peptide or a part thereof. Those which can be utilized are a phoA• signal sequence, an O mpA• signal sequence and the like when a host cell is an *Escherichia* microorganism, an invertase•signal sequence and the like when a host cell is a yeast, an insulin-signal sequence, an α-amylase• signal sequence, a subtilicin• signal sequence and the like when a host cell is a *Bacillus* microorganism, a mating factor α (MFα)• signal sequence, an α-interferon• signal sequence, an antibody molecule• signal sequence and the like when a host cell is an animal cell.

Using a vector containing a DNA encoding a peptide thus constructed, a transformant can be produced.

A host cell may for example be *Escherichia* and *Bacillus* microorganisms, a yeast, an insect or an insect cell, an animal cell and the like.

An *Escherichia* microorganism may for example be *Escherichia coli* K12• DH1 (Proc. Natl. Acad. Sci., USA, Vol. 60, 160 (1968)), JM103 (Nucleic Acids Research, Vol. 9, 309 (1981)), JA221 (Journal of Molecular Biology, Vol. 120, 517 (1978)), HB101 (Journal of Molecular Biology, Vol. 41, 459 (1969)), C600 (Genetics, Vol. 39, 440 (1954)) and the like.

A *Bacillus* microorganism may for example be *Bacillus subtilis* MI114 (Gene, Vol. 24, 255 (1983)), 207-21 (Journal of Biochemistry, Vol. 95, 87 (1984)) and the like.

An yeast may for example be *Saccharomyces cerevisiae* AH22, AH22R$^-$, NA87-11A, DKD-5D, 20B-12 and the like.

An insect may for example be a larva of a silkworm (Maeda et al., Nature, Vol. 315, 592 (1985)).

An insect cell, when a virus is AcNPV, may for example be an armyworm-derived cell line, i.e., a *Spodoptera frugiperda* cell (Sf cell), a *Trichoplusia ni* medium intestine-derived MG1 cell, a *Trichoplusia ni* egg-derived High Five™ cell, a *Mamestra brassicae*-derived cell or an *Estigmena acrea*-derived cell. When a virus is BmNPV, a silkworm-derived cell line *Bombyx mori* N (BmN cell) may be employed. Such Sf cell may for example be an Sf9 cell (ATCC CRL1711), an Sf21 cell (all in Vaughn, J. L. et al., in Vitro, Vol. 13, 213-217, (1977)).

An animal cell may for example be a simian COS-7 cell, a Vero cell, a Chinese hamster cell CHO, a DHFR gene-defeciency chinese hamster cell CHO (CHO/dhfr$^-$ cell), a mouse L cell, a mouse 3T3 cell, a mouse myeloma cell, a human HEK 293 cell, a human FL cell, a 293 cell, a C127 cell, a BALB3T3 cell, an Sp-2/O cell and the like.

In order to transform an *Escherichia* microorganism, a method described in Proc. Natl. Acad. Sci. USA, Vol. 69, 2110 (1972) or in Gene, Vol. 17, 107 (1982) may for example be employed.

In order to transform a *Bacillus* microorganism, a method described in Molecular & General Genetics, Vol. 168, 111 (1979) may for example be employed.

In order to transform an yeast, a method described in Proc. Natl. Acad. Sci. USA, Vol. 75, 1929 (1978) may for example be employed.

In order to transform an insect or an insect cell, a method described in Bio/Technology, Vol. 6, p 47-55 (1988) may for example be employed.

In order to transform an animal cell, a method described in Virology, Vol. 52, p 456 (1973) may for example be employed.

A method for transducing an expression vector into a cell may for example be a lipofection method (Felgner, P. L. et al., Proceedings of the National Academy of Sciences of the United states of America, Vol. 84, p 7413 (1987)), a calcium phosphate method (Graham, F. L. and van der Eb, A. J. Virology, Vol. 52, p 456-467 (1973)), an electroporation method (Nuemann, E. et al., EMBO J., Vol. 1, p 841-845 (1982)) and the like.

As described above, a transformant which has been transformed with an expression vector comprising a DNA encoding a peptide of the invention can be obtained.

In one method for expressing a peptide of the invention stably using an animal cell, a cell in which an expression vector transduced into an animal cell described above is integrated into its chromosome is selected by means of a clone selection. Typically, a transformant is selected using a selection marker described above as an index. Then by repeating the clone selection in the animal cell obtained using such selection marker a reliable animal cell capable of expressing a peptide of the invention at a high level can be obtained. When a dhfr gene is used as a selection marker, the MTX level is raised gradually over the period of incubation to select a resistant strain, in which a DNA encoding an inventive peptide is amplified together with a dhfr gene, whereby obtaining an animal cell line enabling a further higher expression.

A transformant described above is incubated under a condition allowing a DNA encoding a peptide of the invention to be expressed and then the inventive peptide is produced and accumulated, whereby producing the inventive peptide.

For the incubation of transformant when the host cell is an *Escherichia* or *Bacillus* microorganism, a suitable culture medium is a liquid medium, which may contain the components required for the growth of the transformant such as a carbon source, a nitrogen source, an inorganic substance and the like. A carbon source may for example be glucose, dextrin, a soluble starch, sucrose and the like and a nitrogen source may for example be an inorganic or organic material such as an ammonium salt, a nitrate, corn steep liquor, peptone, casein, a meat extract, a soybean flake, a potato extract and the like, and a mineral may for example be calcium chloride, sodium dihydrogen phosphate, magnesium chloride and the like. Those which may also be added are an yeast, vitamins, a growth promoting factor and the like. The pH of a medium is preferably about 5 to 8.

As a culture medium for incubating an *Escherichia* microorganism, an M9 medium containing glucose and a casamino acid [Miller, Journal of Experiments in Molecular Genetics, 431-433, Cold Spring Harbor Laboratory, New York 1972) is preferred. The medium may contain an agent for increasing the promoter efficiency such as 3β-indolylacrylic acid.

When the host cell is an *Escherichia* microorganism, the incubation is performed usually for about 3 to 24 hours at about 15 to 43° C., optionally with aerating and stirring.

When the host cell is a *Bacillus* microorganism, the incubation is performed usually for about 6 to 24 hours at about 30 to 40° C., optionally with aerating and stirring.

For the incubation of transformant when the host cell is a yeast, a suitable culture medium may for example be a Burkholder minimum medium (Bostian, K. L., et al., Proc. Natl. Acad. Sci. USA, Vol. 77, 4505 (1980)) or a 0.5% casamino acid-supplemented SD medium (Bitter, G. A. et al., Proc. Natl. Acad. Sci. USA, Vol. 81, 5330 (1984)) and the like. The pH of a medium is adjusted preferably at about 5 to 8. The incubation is performed usually for about 24 to 72 hours at about 20 to 35° C., optionally with aerating and stirring.

For the incubation of transformant when the host cell is an insect cell, a suitable culture medium may for example be a Grace's Insect Medium (Grace, T. C. C., Nature, 195, 788 (1962)) supplemented appropriately, for example, with an inactivated 10% bovine serum. The pH. of a medium is adjusted preferably at about 6.2 to 6.4. The incubation is performed usually for about 3 to 5 days at about 27° C., optionally with aerating and stirring.

For the incubation of transformant when the host cell is an animal cell, a suitable culture medium may for example be an about 5 to 20% fetal calf serum-supplemented MEM medium (Science, Vol. 122, 501 (1952)), a DMEM medium (Virology, Vol. 8, 396 (1959)), an RPMI 1640 medium (The Journal of the American Medical Association, Vol. 199, 519 (1967)), a 199 medium (Proceeding of the Society for the Biological Medicine, Vol. 73, 1 (1950)) and the like. The pH is preferably about 6 to 8. The incubation is performed usually for about 15 to 60 hours at about 30° C. to 40° C., optionally with aerating and stirring.

Especially when a CHO (dhfr$^-$) cell and a dhfr gene are employed as selection markers, a dialyzed fetal carf serum-supplemented DMEM medium containing almost no thymidine is preferred.

In order to isolate a purified peptide of the invention from a culture described above, the following procedure may for example be employed.

For extracting a peptide of the invention from a cultured bacterial cell or a cell, a cell is collected by a known method after incubation and suspended in a suitable buffer solution, and then destroyed with a lysozyme and/or a freezing-melting cycle, and then subjected to a centrifugation or a filtration, whereby yielding a crude extract of the peptide. The buffer solution may contain a protein modifier such as urea and guanidine hydrochloride or a surfactant such as Triton X-100 (trade mark, hereinafter referred to as ™).

When a peptide is secreted into a culture medium, a supernatant after incubation is separated from a cell by a method known per se and the supernatant is collected.

An incubation supernatant thus obtained or a peptide contained in an extract may be purified by an appropriate combination of separation and isolation methods known per se. Such known separation and isolation methods include a method utilizing the solubility such as a salting out or a solvent sedimentation, a method utilizing the difference in the molecular weight such as a dialysis, an ultrafiltration, a gel filtration and an SDS-polyacrylamide gel electrophoresis, a method for utilizing the difference in the electric charge such as an ion exchange chromatography, a method utilizing the specific affinity such as an affinity chromatography, a method utilizing the difference in the hydrophobicity such as a reverse phase high performance liquid chromatography, a method utilizing the difference in the isoelectric point such as an isoelectric focusing and a chromatofocusing and the like.

When a peptide of the invention thus obtained is in a free form it can be converted into a salt by a method known per se or equivalent, and when it is obtained as a salt it can be converted into a free form or another salt by a method known per se or equivalent.

By bringing an inventive peptide produced by a transformant into contact with a suitable protein-modifying enzyme before or after purification, an optional modification can be carried out or a peptide can partially be removed. Such protein-modifying enzyme may for example be trypsin, chymotryipsin, arginylendopeptidase, proteinkinase, glycosidase and the like.

A peptide of the invention thus obtained can be identified by an enzyme immunoassay using a specific antibody.

A DNA encoding a peptide of the invention or a peptide of the invention can be employed in (1) a synthesis of a part of or an entire length of a ligand of a galanin receptor protein, (2) a characterization of a physiological activity possessed by a peptide of the invention, (3) a production of a synthetic oligonucleotide probe or a PCR primer, (4) an acquisition of a DNA encoding a ligand or a precursor of a G protein-conjugate receptor protein, (5) a development of a receptor binding assay system using an expression system of a recombinant receptor protein and a screening for a pharmaceutical candidate compound, (6) an acquisition of an antibody and an antiserum, (7) a development of a diagnostic agent using a DNA, RNA, antibody or antiserum, (8) a development of pharmaceutical such as a memory function improving agent (intelligence-tropic agent), an appetite regulating agent, a diabetes treating agent, a pituitary gland function improving agent, an uterine function regulating agent, a renal function regulating agent, a prostatic function regulating agent, a testicular function regulating agent or a skeletal muscle function regulating agent (preferably, a memory function improving agent (intelligence-tropic agent), an appetite regulating agent, an uterine function regulating agent, a renal function regulating agent, a prostatic function regulating agent, a testicular function regulating agent or a skeletal muscle function regulating agent), (9) a gene therapy and the like.

Particularly by using a receptor binding assay system using an expression system of a recombinant G protein-conjugate receptor protein described above, a G protein-conjugate receptor agonist or antagonist specific to a warm-blooded animal such as a human can be screened and such agonist or antagonist can be utilized as a prophylactic or therapeutic agent against various diseases.

Furthermore in conjunction with (8) described above, since the peptide or a DNA encoding it of the invention can be recognized as a ligand by a galanin receptor (GALR) protein expressed in hippocampus, hypothalamus, uterus, kidney, prostate, skeletal muscle, pancreas, testis, spleen, heart and pituitary gland, it is useful as a safe and less toxic pharmaceutical, which can be employed for example as a memory function improving agent (intelligence-tropic agent), an appetite regulating agent, a diabetes treating agent, a pituitary gland function improving agent, an uterine function regulating agent, a renal function regulating agent, a prostatic function regulating agent or a skeletal muscle function regulating agent (preferably, a memory function improving agent (intelligence-tropic agent), an appetite regulating agent, an uterine function regulating agent, a renal function regulating agent, a prostatic function regulating agent or a skeletal muscle function regulating agent) and the like.

When a peptide of the invention or a DNA encoding it is employed as pharmaceutical described above, an ordinary customary procedure is followed. For example, a tablet, capsule, elixir or microcapsule optionally coated with a sugar coating or an enteric coating is provided for an oral administration, or an aseptic solution or suspension in water or other pharmaceutically acceptable liquids for injection is provided for a parenteral administration. For example, a compound or its salt is mixed with physiologically acceptable carrier, flavor, excipient, vehicle, preservative, stabilizer, binders and the like and formulated into a pharmaceutically acceptable unit dosage form. The amount of an active ingredient in such formulation should be adjusted so that a dose within an indicated range can be obtained.

When a DNA of the invention is employed, such DNA is employed customarily as it is or after being inserted in a suitable vector such as a retrovirus vector, an adenovirus vector, an adenovirus-associated virus vector and the like.

An additive to be added to a tablet or a capsule may for example be a binder such as gelatin, corn starch, gum tragacanth, gum arabic and the like, an excipient such as crystalline cellulose, an extender such as corn starch, gelatin, alginic acid and the like, a lubricant such as magnesium stearate, a sweetener such as sucrose, lactose or saccharin, a flavor such as peppermint, ACAMONO oil or cherry flavor. When a unit dosage form is a capsule, a liquid carrier such as an oil may also be contained in addition to the materials listed above. An aseptic composition for injection may be formulated customarily by dissolving or suspending an active ingredient and a naturally-occurring vegetable oil such as sesame oil or palm oil in a vehicle such as water for injection.

A water-based vehicle for injection may for example be physiological saline, an isotonic solution containing glucose or other agents (e.g., D-sorbitol, D-mannitol, sodium chloride and the like), optionally containing a suitable solubilizing agent such as an alcohol (e.g., ethanol), a polyalcohol (e.g., propylene glycol, polyethylene glycol), a non-ionic surfactant (e.g., polysorbate 80™, HCO-50). An oil-based vehicle may for example be sesame oil or soybean oil, optionally containing a solubilizing agent such as benzyl benzoate, benzyl alcohol and the like.

A buffer (e.g., phosphate buffer, sodium acetate buffer), an analgesic agent (e.g., benzalkonium chloride, procaine hydrochloride and the like), a stabilizer (e.g., human serum albumin, polyethylene glycol and the like), a preservative (e.g., benzyl alcohol, phenol and the like), an antioxidant may also be incorporated. A formulation for injection thus prepared is filled usually in an appropriate ampoule.

Since a formulation thus obtained is safe and less toxic, it can be administered to a human or a mammal (e.g., mouse, rat, guinea-pig, rabbit as well as ovine, porcine, bovine, feline, canine, simian animals and the like).

A peptide of the invention or a DNA encoding it may generally be administered to an adult (weighing 60 kg) orally as such peptide at a dose ranging from about 0.1 to 100 mg, preferably about 1.0 to 50 mg, more preferably about 1.0 to 20 mg, although the dose may vary depending on the conditions. When such peptide is given parenterally (for example via an intravenous injection), the single daily dose as a solution for injection in an adult (weighing 60 kg) is about 0.01 to 30 mg, preferably about 0.1 to 20 mg, more preferably about 0.1 to 10 mg, although the dose may vary depending on the subject to be administered, the organ to be treated, the condition and the administration mode.

Also in other species, a corresponding dose can be obtained by converting the dose per 60 kg body weight described above to a dose per the body weight of the respective animal.

In the invention, a galanin receptor is a G protein-coupled receptor protein derived from various tissues (e.g., pituitary gland, pancreas, brain, kidney, liver, gonad, thyroid gland, gallbladder, bone marrow, adrenal gland, skin, muscle, lung, digestive tract, blood vessel, heart and the like) and cells of a human or a warm-blooded animal (e.g., mammalian warm-blooded animal (e.g., rabbit, ovine and caprine animals, rat, mouse, guinea-pig as well as bovine, equine and porcine animals), avian animals (e.g., chicken, pigeon, duck, goose, quail) and the like), and each of GALR1, 2 and 3 may be any protein as long as it comprises an amino acid sequence identical to or substantially identical to the amino acid sequence represented by each of SEQ ID NOs: 1, 2 and 3, respectively. Thus, such receptor protein may be a protein comprising an amino acid sequence represented by SEQ ID NO: 1, 2 or 3, as well as a protein having a homology of about 90 to 99.9% with an amino acid sequence represented by SEQ ID NO: 1, 2 or 3 and having an activity whose quality is substantially analogous to a protein comprising an amino acid sequence represented by SEQ ID NO: 1, 2 or 3.

The activity exerted by such protein may for example be a ligand binding activity, a signal transmission activity and the like. The quality which is substantially analogous means that the activity is qualitatively analogous. Accordingly, the quantitative factors of this activity, such as the potency of a ligand binding activity and a signal transmission activity or the molecular weight of a receptor protein may be different.

Furthermore, such receptor protein includes one whose Met at the N-terminal is protected (for example with a $C_{1-6}$ alkanoyl group such as formyl and acetyl groups), one whose glutamine residue at the N-terminal is derivatized to a pyroglutamic acid, one whose side chain of an amino acid in molecule is protected (for example with a $C_{1-6}$ alkanoyl group such as formyl and acetyl groups) or a complex protein such as a glycoprotein having a saccharide chain bound thereto.

A salt of such receptor protein may be one exemplified as a salt of a peptide described above.

Such receptor protein, its salt or its partial peptide may be produced by a protein purification method known per se from a tissue or a cell of a human or a warm-blooded animal, or may be produced by a method similar to that for incubating a transformant comprising a DNA encoding a peptide described above. A peptide synthesis described above may also be employed.

A partial peptide of such receptor protein may for example be a G protein-coupled receptor protein molecule which is protruded out of the cell membrane. Thus, this is a peptide containing a moiety which is judged to be an extracellular region (hydrophilic moiety) in a hydrophobicity plot analysis of a G protein-coupled receptor protein. A peptide partially containing a hydrophobic moiety may similarly be employed. While a peptide containing a single domain may be employed, another peptide containing two or more domains at the same time may also be employed.

A salt of a partial peptide of such receptor protein may be one exemplified as a salt of a peptide described above.

A DNA encoding such galanin receptor protein may be any protein comprising a base sequence encoding a galanin receptor protein comprising an amino acid sequence identical to or substantially identical to an amino acid sequence of SEQ ID NO: 1, 2 or 3. Furthermore, a genome DNA, a genome DNA library, a cDNA derived from a tissue or cell, a cDNA library derived from a tissue or cell and a synthetic DNA may also be employed. A vector used in a library may be a bacteriophage, a plasmid, a cosmid or a phagemid and the like. A direct amplification from an RNA fraction prepared from a tissue or cell may also be performed by an RT-PCR method known per se.

A DNA encoding a galanin receptor comprising an amino acid sequence of SEQ ID NOs: 1, 2 and 3 may typically be a DNA having a base sequence represented by SEQ ID NOs: 4, 5 and 6, respectively.

GALR2 (galanin receptor type 2) is present in a large amount in hippocampus, hypothalamus, uterus, kidney, prostate and skeletal muscle, and thus a peptide of the invention which is an agonist having a GALR2 activating ability (or an antagonist against GALR2 or a neutralization antibody against a peptide of the invention) may be employed as a memory function improving agent, an appetite improving agent, an uterine, renal, prostatic or skeletal muscle function improving agent.

GALR1 (galanin receptor type 1) is present in a large amount in hypothalamus, hippocampus and pancreas, and thus a peptide of the invention which is an agonist having a GALR1 activating ability (or an antagonist against GALR1 or a neutralization antibody against a peptide of the invention) may be employed as an anti-obesity agent, a intelligence-tropic agent and an insulin-secreting agent.

GALR3 (galanin receptor type 3) is present in a large amount in testis, spleen, heart, hypothalamus and pituitary gland, and thus a peptide of the invention which is an agonist having a GALR3 activating ability (or an antagonist against GALR3 or a neutralization antibody against a peptide of the invention) may be employed as an agent for improving the function of testis, spleen or heart.

The present invention provides (1) a method for screening for a galanin receptor-activating substance (agonist) or its salt comprising determining and comparing the amount of the binding, for example, of $^{35}$S-labeled guanosin-5'-O-3-thiotriphosphate to a cell membrane fraction when a test substance is (1) in contact with and (2) not in contact with such cell membrane fraction expressing a galanin receptor obtained by incubating a transformant (cell) comprising a DNA encoding such galanin receptor, and (2) a method for screening for a galanin receptor activation-inhibiting substance (antagonist) or its salt comprising determining and comparing the amount of the binding, for example, of $^{35}$S-labeled guanosin-5'-O-3-thiotriphosphate to a cell membrane fraction when a galanin or an inventive peptide is in contact with such cell membrane fraction expressing a galanin receptor obtained by incubating a transformant (cell) comprising a DNA encoding such galanin receptor (1) in the absence and (2) in the the presence of a test substance.

A method for screening according to the invention is detailed below.

While a galanin receptor protein described above may be any protein which comprises a galanin receptor protein of either GALR1, GALR2 or GALR3 or a part thereof and which has such receptor function, it is preferably a cell membrane fraction prepared (by a method described below) from a cell culture in which such galanin receptor is expressed in a large amount using a transformant (cell).

A cell comprising such galanin receptor protein means a host cell which expresses the galanin receptor protein, and such host cell may for example be a yeast, an insect cell or an animal cell described above, with an animal cell being preferred.

Such membrane fraction means a fraction containing a large amount of a cell membrane obtained by a method known per se after destroying the cell. A method for destroying the cell may be a method in which a cell is pressed using a Potter-Elvehjem type homogenizer, a method in which a cell is pelletized using a whirling blender or a Polytron (Kinematica), an ultrasonic pelletization, or a pelletization by spraying it via a fine nozzle with pressurizing by a French Press. The fractionation of a cell membrane is performed by a centrifugal fractionation such as a fractional centrifugation or a gradient centrifugation. For example, a cell pellet is centrifuged at a low speed (500 rpm to 3000 rpm) for a short period (usually about 1 minute to 10 minutes) and the supernatant is centrifuged at a higher speed (1500 rpm to 30000 rpm) usually for 30 minutes to 2 hours, to obtain a precipitation as a membrane fraction. This membrane fraction consists mainly of a membranous protein and a cell membrane constituent phospholipid, and contains an expressed galanin receptor together with a G protein which is expressed naturally by the cell.

The amount of a galanin receptor in the cell comprising such galanin receptor or in a membrane fraction is preferably 1 to 100 pmol, more preferably 5 to 20 pmol, per 1 mg of the membrane fraction protein. A higher expression of such galanin receptor results in a higher receptor activating activity per membrane fraction (ligand binding activity, specific activity), whereby allowing a highly sensitive screening system to be constructed and enabling an assay of a large amount of a sample using only one identical lot.

In a method for screening for a compound which activates a galanin receptor (agonist), a membrane fraction of a cell comprising a galanin receptor is first suspended in a buffer solution suitable for a screening, whereby preparing a receptor reference standard. Such buffer solution may for example be a phosphate buffer or a tris-HCl buffer containing about 1 to 5 mM magnesium ion at a pH of about 4 to about 10 (preferably about 6 to about 8), optionally supplemented with guanosine diphosphate at about 0.1 nM to 100 µM, preferably, about 0.1 to 1 µM. For the purpose of suppressing the degradation of a receptor or a test substance by a protease, a protease inhibitor such as PMSF, leupeptine, E-64 (PEPTIDE KENKYUSHO) and pepstatin may be added. To about 0.01 to 10 ml of a receptor solution, a certain amount (5000 cpm to 50000 cpm) of $^{35}$S-labeled guanosine-5'-O-3-thiotriphosphate and a test substance are added. A test substance-free reaction system (control) containing only $^{35}$S-labeled guanosine-5'-O-3-thiotriphosphate is also provided. The reaction is performed at about 0 to 50° C., preferably about 4° C. to 37° C., for about 20 minutes to 24 hours, preferably about 30 minutes to 3 hours. After the reaction, the mixture is filtered through a glass fiber filter or equivalent, which was washed with a suitable volume of the same buffer solution, and then the radioactivity of the $^{35}$S-labeled guanosine-5'-O-3-thiotriphosphate remaining on the glass fiber filter is counted by a liquid scintillation counter. A compound giving a substantial increase from the radioactivity in the absence of a test substance to the radioactivity in the presence of the test substance can be selected as a candidate of a compound capable of activating a galanin receptor.

To screen for a compound which inhibits the activation of a galanin receptor (antagonist), a cell membrane fraction is provided similarly to the screening for an agonist described above, and then combined with a certain amount (5000 cpm to 50000 cpm) of $^{35}$S-labeled guanosine-5'-O-3-thiotriphosphate, a galanin or an inventive peptide at $10^{-4}$ to $10^{-6}$M and a test substance. A test substance-free reaction system (control) containing only $^{35}$S-labeled guanosine-5'-O-3-thiotriphosphate and the galanin or the inventive peptide is also provided. The reaction is performed as described above, and a compound giving a substantial decrease from the radioactivity in the absence of a test substance to the radioactivity in the presence of the test substance can be selected as a candidate of a compound capable of inhibiting the activation of a galanin receptor.

Such test substance may for example be a peptide, a protein, a non-peptide compound, a synthetic compound, a fermentation product, a cell extract, a vegetable extract or an animal tissue extract and the like, which may be a novel substance or a substance known per se.

Since a galanin receptor agonist has an activity similar to the physiological activity possessed by an inventive peptide toward the galanin receptor, it is useful as a safe and less toxic pharmaceutical agent similarly of the inventive peptide.

On the contrary, since a galanin receptor antagonist can inhibit the physiological activity possessed by an inventive peptide toward the galanin receptor protein, it is useful as a safe and less toxic pharmaceutical which suppresses such receptor activity.

A salt of a substance obtained by a screening method described above may for example be a pharmaceutically acceptable salt. For example, a salt with an inorganic base, a salt with an organic base, a salt with an inorganic acid, a salt with an organic acid, and a salt with a basic or acidic amino acid may be contemplated.

Preferred examples of a salt with an inorganic base are an alkaline metal salt such as a sodium salt and a potassium salt, an alkaline earth metal salt such as a calcium salt and a magnesium salt, as well as an aluminum salt and an ammonium salt.

Preferred examples of a salt with an organic base are salts with trimethylamine, triethylamine, pyridine, picolin, 2,6-lutidine, ethanolamine, diethanolamine, triethanolamine, cyclohexylamine, dicyclohexylamine, N,N'-dibenzylethylene diamine, and the like.

Preferred examples of a salt with an inorganic acid are salts with hydrochloric acid, hydrobromic acid, sulfuric acid, phosphoric acid and the like.

Preferred examples of a salt with an organic acid are salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid and the like.

Preferred examples of a salt with a basic amino acid are salts with arginine, lysine, ornithine, and the like, and those of an acidic amino acid are salts with aspartic acid, glutamic acid and the like.

When a substance obtained by a screening method of the invention or a salt thereof is used as a pharmaceutical agent, it can be used in a manner similar to the manner for using an inventive peptide described above as a pharmaceutical agent.

An antibody or an antiserum to a peptide of the invention (for example, polyclonal antibody, monoclonal antibody) can be produced using the peptide of the invention as an antigen in accordance with an antibody or antiserum production method known per se.

For example, a polyclonal antibody can be produced in accordance with a method described below.

[Production of Polyclonal Antibody]

A polyclonal antibody to a peptide of the invention can be produced in a method known per se or an equivalent method. For example, a complex of an immune antigen (antigen such as peptide) with a carrier protein is formed and used to immunize a warm-blooded animal (e.g., mammalian warm-blooded animal (e.g., rabbit, ovine and caprine animals, rat, mouse, guinea-pig as well as bovine, equine and porcine animals), avian animals (e.g., chicken, pigeon, duck, goose, quail) and the like) in a manner similar to that for producing a monoclonal antibody described below, and a substance containing an antibody to an inventive peptide is isolated from an immunized animal and then isolated as being purified, whereby obtaining the antibody.

With regard to a complex of an immune antigen and a carrier protein used for immunizing a mammalian animal, the type of the carrier protein and the mixing ratio of the carrier and a hapten (an inventive peptide or its partial peptide) may not particularly be limited and any substances may be crosslinked at any ratio as long as the antibody can be produced efficiently on the basis of the hapten immunized by crosslinking with the carrier, but in a usual case a carrier protein such as bovine serum albumin, bovine seroglobulin, keyhole limpet hemocyanin and the like is coupled in an amount of about 0.1 to 20, preferably about 1 to 5 per 1 part by weight of the hapten.

While various condensing agents are employed in the coupling of a hapten with a carrier, those employed usually are glutaraldehyde, carbodiimide, maleimide activated ester, an activated ester reagent containing a thiol group or a dithiopyridyl group.

A condensation product is administered to a warm-blooded animal described above as it is or with a diluent or a carrier to a site capable of producing an antibody. In order to enhance the antibody producing ability, a complete Freund's adjuvant or an incomplete Freund's adjuvant may also be administered. The administration is performed usually once per about 2 to 6 weeks, and about 3 to 10 times in total.

A polyclonal antibody can be isolated from blood or ascites, preferably blood, of a mammalian animal immunized as described above.

The antibody titre to a peptide of the invention in an antiserum can be measured in a manner similar to that for measuring an antibody titre of a hybridoma culture supernatant described below. An antibody can be isolated as purified in accordance with a method for isolating and purifying an immunoglobulin similarly to a method for isolating and purifying a monoclonal antibody described below.

A monoclonal antibody can be produced by a method described below.

[Production of Monoclonal Antibody]

(a) Production of Monoclonal Antibody-Producing Cell

A peptide of the invention is given to a warm-blooded animal (e.g., mammalian warm-blooded animal (e.g., rabbit, ovine and caprine animals, rat, mouse, guinea-pig as well as bovine, equine and porcine animals), avian animals (e.g., chicken, pigeon, duck, goose, quail) and the like) as it is or with a diluent or a carrier to site capable of producing an antibody after administration. In order to enhance the antibody producing ability, a complete Freund's adjuvant or an incomplete Freund's adjuvant may also be administered. The administration is performed usually once per about 2 to 6 weeks, and about 2 to 10 times in total.

In producing a monoclonal antibody-producing cell, a warm-blooded animal, for example a mouse, immunized with an antigen is screened for an individual showing an antibody titre, which is sacrificed 2 to 5 days after the final immunization to obtain a spleen or a lymph node, an antibody-producing cell contained in which is fused with a myeloma cell, whereby obtaining a monoclonal antibody-producing hybridoma. The antibody titre of an antiserum can be determined for example by reacting a peptide or a part thereof labeled as described below with an antiserum, followed by measuring the activity of the label bound to the antibody. The fusion can be accomplished by a known method such as a method by KELLER and MILLSTEIN (Nature, 256, 495 (1975)). A fusion promoter may for example be a polyethylene glycol (PEG) or a Sendai virus, with a PEG being preferred.

A myeloma cell may for example be NS-1, P3U1, SP2/0, AP-1 and the like, with P3U1 being employed preferably. The preferred ratio of the cell counts of an antibody-producing cell (spleen cell) and a myeloma cell employed may be 1:1 to 20:1, and a PEG (preferably PEG1000 to PEG6000) is added at a concentration of about 10 to 80%, and an incubation is performed at 20 to 40° C., preferably 30 to 37° C., for 1 to 10 minutes, whereby effecting an efficient cell fusion.

While various methods can be employed for screening for a hybridoma which produces an antibody to a peptide of the invention, the methods which can be exemplified are a method in which a hybridoma culture supernatant is added to a solid phase (such as a microplate) onto which an inventive peptide antigen has been adsorbed directly or with a carrier and then an anti-immunoglobulin antibody (anti-mouse immunoglobulin antibody when a mouse cell is fused) or a protein A labeled with a radioactive substance or an enzyme is added whereby detecting a monoclonal antibody to the inventive peptide bound to the solid phase and a method in which a hybridoma culture supernatant is added to a solid phase onto which an anti-immunoglobulin antibody or a protein A has been adsorbed and a peptide of the invention labeled with a radioactive substance or an enzyme is added whereby detecting a monoclonal antibody to the inventive peptide bound to the solid phase.

A monoclonal antibody to a peptide of the invention can be screened by a method known per se or an equivalent method. An HAT (hypoxanthine, aminoputerine, thymidine)-supplemented culture medium for an animal cell is employed usually. A medium for screening and breeding may be any medium as long as a hybridoma can be grown. For example, a 1 to 20%, preferably 10 to 20% fetal bovine serum-supplemented RPMI 1640 medium, a 1 to 10% fetal bovine serum-supplemented GIT medium (WAKO PURE CHEMICAL INDUSTRIES, LTD.) or a serum-free medium for a hybridoma culture (SFM-101, NISSUI PHARMACEUTICAL CO., LTD.) can be employed. The incubation temperature may usually be 20 to 40° C., preferably about 37° C. The incubation time is usually 5 days to 3 weeks, preferably 1 week to 2 weeks. The incubation is conducted usually in the presence of 5% $CO_2$ gas. The antibody titre of a hybridoma culture supernatant can be determined similarly to the determination of the antibody titre to an inventive peptide in an antiserum described above.

(b) Purification of Monoclonal Antibody

A monoclonal antibody to an inventive peptide can be isolated as purified in accordance with a method for isolating and purifying an immunoglobulin similarly to an ordinary polyclonal antibody isolation and purification (e.g., salting out, alcohol sedimentation, isoelectric precipitation, electrophoresis, ion exchanger (e.g., DEAE) adsorption/desorption, ultracentrifugation, gel filtration, a specific purification in which an antibody is collected exclusively using an antigen-bound solid phase or an active adsorbent such as Protein A or G and then the bond is cleaved to yield the antibody).

Since each antibody to a peptide of the invention produced in accordance with Methods (a) and (b) described above can recognize the respective peptide of the invention specifically, it can be used to quantify the peptide of the invention in a sample solution, especially by means of a sandwich immunoassay. Thus, the present invention provides, for example:

(i) a method for quantifying a peptide of the invention in a sample solution in which an antibody reactive with the inventive peptide is reacted with the sample solution and a labeled peptide of the invention competitively and then the rate of the labeled inventive peptide bound to the antibody is determined; and, (ii) a method for quantifying a peptide of the invention in a sample solution in which the sample solution is reacted with an antibody insolubilized on a carrier and a labeled antibody simultaneously or continuously, wherein one antibody is an antibody recognizing the N-terminal of the peptide of the invention and the other antibody is an antibody reactive with a site other than the N-terminal of the peptide of the invention (such as the C-terminal).

A monoclonal antibody recognizing a peptide of the invention is used not only in an assay of the peptide of the invention but also in a detection on the basis of a tissue staining. For such purposes, an antibody molecule itself may be employed, or an F(ab') 2, Fab' or Fab fraction of the antibody molecule may also be employed. An assay using an antibody of the invention is not particularly specified, and may be any assay as long as it determines the amount of an antibody, antigen or antibody-antigen complex corresponding to the amount of the antigen (e.g., the level of a ligand peptide) in a sample solution and then calculates the level on the basis of the calibration curve obtained by using the standard solutions containing known amounts of the antigen. While the methods employed preferably may for example be a nephrometry, a competitive assay, an immunometric assay and a sandwich assay, a particularly preferred method is a sandwich assay described below in view of the sensitivity and the specificity.

A label employed in the assay using a labeled substance may for example be a radioisotope, an enzyme, a fluorescent substance and a luminescent substance. A radioisotope may for example be [$^{125}$I], [$^{131}$I], [$^{3}$H], [$^{14}$C] and the like, an enzyme may preferably a stable enzyme having a high specific activity, such as β-galactosidase, β-glucosidase, alkaline phosphatase, peroxidase, malate dehydrogenase and the like, a fluorescent substance may for example be fluorescamine, and fluorescenisothiocyanate and the like, and a luminescent substance may for example be luminol, a luminol derivative, luciferin, lucigenin and the like. A biotin-abidin system can also be employed to bind an antibody or an antigen to a label.

An insolubilization of an antigen or an antibody may be performed using a physical adsorption, or using a chemical bond employed usually for insolubilizing and immobilizing a protein or an enzyme. A carrier may for example be an insoluble saccharide such as agarose, dextran and cellulose, a synthetic resin such as polystyrene, polyacrylamide and silicon, as well as a glass.

In a sandwich assay, an insolubilized antibody to an inventive peptide is reacted with a sample solution (primary reaction), and then with a labeled antibody to an inventive peptide (secondary reaction), and subsequently the activity of the label on an insolubilized carrier is determined to quantify the peptide of the invention in the sample solution. The primary reaction and the secondary reaction may be performed in the reverse order, simultaneously or at a certain time interval.

A labeling and a insolubilization may be performed in accordance with the methods described above. In an immunoassay by a sandwich assay, an antibody employed as an antibody for a solid phase or as an antibody for labeling is not necessarily of a single type, and two or more antibodies may be used in a mixture for the purpose of obtaining a higher sensitivity of the assay.

In an inventive peptide assay utilizing a sandwich assay of the invention, an antibody to the inventive peptide employed in the primary and secondary reactions may preferably have the inventive peptide-binding sites which are different from each other. Thus, the antibodies employed in the primary and secondary reactions can be selected so that when the antibody employed in the second reaction recognizes the C-terminal of the inventive peptide then the antibody employed in the primary reaction is preferably an antibody which recognizes the site other than the C-terminal, such as the N-terminal.

An antibody to the peptide of the invention can be used in an assay system other than a sandwich assay, such as a competitive assay, an immunometric assay and a nephrometry. In a competitive assay, an antigen in a sample solution and a labeled antigen are reacted competitively with an antibody, and then an unreacted labeled antigen (F) and an antibody-binding antigen (B) are separated (B/F separation), and the label on either B or F is quantified whereby quantifying the antigen in the sample solution. In this reaction, a soluble antibody is employed as an antibody and the B/F separation is conducted by a liquid phase method using a second antibody to the polyethylene glycol and antibody described above, and by a solid phase method using as a first antibody a solidified antibody or using as a first antibody a soluble antibody and as a second antibody a solidified antibody.

In an immunometric assay, an antigen in a sample solution and a solidified antigen are reacted competitively with a certain amount of a labeled antibody and then the solid phase and the liquid phase are separated, or, in an alternative procedure, an antigen in a sample solution and an excess of a labeled antibody are reacted and then a solidified antigen is added to allow an unreacted labeled antibody to be bound to the solid phase, and subsequently the solid phase and the liquid phase are separated. Thereafter, the label in either phase is quantified whereby quantifying the antigen in the sample solution.

In a nephrometry, the amount of an insoluble sediment formed as a result of an antigen-antibody reaction in a gel or a solution is determined. Even when a sample solution contains only a trace amount of an antigen and the resultant sediment is sparse, a laser nephrometry utilizing a laser scatter can preferably be employed.

When applying any of the immunological techniques described above to an assay of the invention, no particular conditions and operations are specified. An usual condition and operation for each technique with a technical consideration of those skilled in the art may be acceptable for constructing an assay system for an inventive peptide or a part thereof. Such ordinary techniques are described in various literatures [e.g., H. Irie Ed., "Radioimmunoassay", KODANSHA, Published in 1974, H. Irie Ed., "Radioimmunoassay 2", KODANSHA, Published in 1979, E. Ishikawa et al., Ed., "Enzyme immunoassay", IGAKUSHOIN, Published in 1978, E. Ishikawa et al., Ed., "Enzyme immunoassay", (2nd edition) IGAKUSHOIN, Published in 1982, E. Ishikawa et al., Ed., "Enzyme immunoassay", (3rd edition) IGAKUSHOIN, Published in 1987, "Methods in ENZYMOLOGY", Vol. 70, Immunochemical Techniques (Part A), Vol. 73, Immunochemical Techniques (Part B), Vol. 74, Immunochemical Techniques (Part C), Vol. 84, Immunochemical Techniques (Part D: Selected immunoassays), Vol. 92, Immunochemical Techniques (Part E: Monoclonal Antibodies and General Immunoassay Methods), Vol. 121, Immunochemical Techniques (Part I: Hybridoma Technology and Monoclonal Antibodies), Academic Press, etc].

As described above, by using an antibody to a peptide of the invention, the peptide of the invention can sensitively be quantified.

In addition, by determining the concentration of a peptide of the invention using an antibody of the invention, a use as a diagnostic agent can be made. Thus:

(1) When a change in the concentration of a protein of the invention or equivalent is noted, then a diagnosis or a suggestion of a future risk of obesity, dementia, diabetes or pituitary tumor can be made.

An antibody of the invention can be used also for detecting an inventive protein present in a sample such as a body fluid or a tissue. It may be used also to produce an antibody column for purifying an inventive protein, to detect an inventive protein in each fraction during purification, or to analyze the behavior of an inventive protein in a test cell.

In the specification and attached Figures, a base or an amino acid when abbreviated is designated on the basis of IUPAC-IUB Commission on Biochemical Nomenclature or as customarily in the art, as exemplified below. An optical isomer of an amino acid, if any, is an L-form, unless otherwise specified.

DNA: Deoxyribonucleic acid
cDNA: Complementary deoxyribonucleic acid
A: Adenine
T: Thymine
G: Guanine
C: Cytosine
Y: Thymine or cytosine
N: Thymine, cytosine, adenine or guanine
R: Adenine or guanine
M: Cytosine or adenine
W: Thymine or adenine
S: Cytosine or guanine
I: Inosine
H: Adenine, thymine or cytosine
D: Guanine, adenine or thymine
B: Guanine, thymine or cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediamine tetracetic acid
SDS: Sodium dodecylsulfate
EIA: Enzyme immunoassay Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Aspargine
Gln or Q: Glutamine
pGlu: Pyroglutamic acid
Me: Methyl group
Et: Ethyl group
Bu: Butyl group
Ph: Phenyl group
TC: Thiazolidine-4(R)-carboxyamide group
Substituents, protective groups and reagents employed in the specification are designated as follows.
Tos: p-Toluenesulfonyl
HONB: N-Hydroxy-5-norbornene-2,3-dicarboxyimide
Bzl: Benzyl
Cl$_2$-Bzl: Dichlorobenzyl
Z: Benzyloxycarbonyl
Br-Z: 2-Bromobenzyloxycarbonyl
Cl-Z: 2-Clorobenzyloxycarbonyl
Boc: t-Butyloxycarbonyl
HOBt: 1-Hydroxybenzotriazole
DCC: N,N'-Dicyclohexylcarbodiimide
TFA: Trifluoroacetic acid
Fmoc: N-9-Fluorenylmethoxycarbonyl
DNP: Dinitrophenyl
Bum: t-Butoxymethyl
Trt: Trityl
PAM: Phenylacetoamidomethyl
BHA: Benzohydrylamine
Bom: Benzyloxymethyl
OcHex: Cyclohexylester
MeBzl: 4-Methylbenzyl
CHO: Formyl
NMP: N-Methylpyrrolidone The SEQ ID NOs in the sequence listing in the specification represents the following sequences.

[SEQ ID NO: 1]
This represents the entire amino acid sequence of rat GALR1 (galanin receptor type 1).

[SEQ ID NO: 2]
This represents the entire amino acid sequence of rat GALR2 (galanin receptor type 2).

[SEQ ID NO: 3]
This represents the entire amino acid sequence of rat GALR3 (galanin receptor type 3).

[SEQ ID NO: 4]
This represents the base sequence of a cDNA of rat GALR1 (galanin receptor type 1).

[SEQ ID NO: 5]
This represents the base sequence of a cDNA of rat GALR2 (galanin receptor type 2).

[SEQ ID NO: 6]
This represents the base sequence of a cDNA of rat GALR3 (galanin receptor type 3).

[SEQ ID NO: 7]
This represents the entire amino acid sequence of porcine galanin (29 residues).

[SEQ ID NO: 8]
This represents the amino acid sequence of porcine galanin precursor preprogalanin (1-123).

[SEQ ID NO: 9]
This represents the amino acid sequence of porcine galanin precursor preprogalanin (24-61).

[SEQ ID NO: 10]
This represents the amino acid sequence of porcine galanin precursor preprogalanin (37-61).

[SEQ ID NO: 11]
This represents the partial amino acid sequence (34 residues from N-terminal) of a porcine peptide of the invention.

[SEQ ID NO: 12]
This represents the partial amino acid sequence (32 residues from N-terminal) of a porcine peptide of the invention.

[SEQ ID NO: 13]
This represents the partial amino acid sequence (9 residues from N-terminal) of a chymotrypsin digestion fragment (CHY-1) of a porcine peptide of the invention.

[SEQ ID NO: 14]
This represents the partial amino acid sequence (6 residues) of a chymotrypsin digestion fragment (CHY-4) of a porcine peptide of the invention.

[SEQ ID NO: 15]
This represents the partial amino acid sequence (27 residues) of a chymotrypsin digestion fragment (CHY-3) of a porcine peptide of the invention.

[SEQ ID NO: 16]
This represents the partial amino acid sequence (11 residues) of a chymotrypsin digestion fragment (CHY-2) of a porcine peptide of the invention.

[SEQ ID NO: 17]
This represents the partial amino acid sequence (44 residues) of a porcine peptide of the invention.

[SEQ ID NO: 18]
This represents a synthetic DNA (primer 1) employed in a screening for a base sequence of cDNA encoding rat GALR2.

[SEQ ID NO: 19]
This represents a synthetic DNA (primer 2) employed in a screening for a base sequence of cDNA encoding rat GALR2.

[SEQ ID NO: 20]
This represents a synthetic DNA (primer pGAL4-7F) employed in a degenerated PCR.

[SEQ ID NO: 21]
This represents a synthetic DNA (primer pGAL9-3F) employed in a degenerated PCR.

[SEQ ID NO: 22]
This represents a synthetic DNA (primer pGAL34-1R) employed in a degenerated PCR.

[SEQ ID NO: 23]
This represents the base sequence of a nested PCR product in pCR100-6.

[SEQ ID NO: 24]
This represents the base sequence of a nested PCR product in pCR100-7.

[SEQ ID NO: 25]
This represents a synthetic DNA (primer pGAL9-3F) employed in the preparation of a hybridization probe.

[SEQ ID NO: 26]
This represents a synthetic DNA (primer pGAL34-8R) employed in the preparation of a hybridization probe.

[SEQ ID NO: 27]
This represents the base sequence of a cDNA in pGR2PL6 obtained in Example 5.

[SEQ ID NO: 28]
This represents the base sequence of a cDNA in pGR2PL3 obtained in Example 5.

[SEQ ID NO: 29]
This represents the sequence of a precursor of a peptide of the invention assumed from the base sequence of a cDNA in pGR2PL6.

[SEQ ID NO: 30]
This represents the sequence of a precursor of a peptide of the invention assumed from the base sequence of a cDNA in pGR2PL3.

[SEQ ID NO: 31]
This represents the sequence of a (porcine) mature protein of a peptide of the invention assumed from the base sequence of cDNAs in pGR2PL6 and pGR2PL3.

[SEQ ID NO: 32]
This represents a (porcine) cDNA sequence encoding a mature protein of an inventive peptide.

[SEQ ID NO: 33]
This represents the sequence of a (rat) mature protein of an inventive peptide.

[SEQ ID NO: 34]
This represents the sequence of a (human) mature protein of an inventive peptide.

[SEQ ID NO: 35]
This represents the partial amino acid sequence (9 residues from N-terminal) of a mature protein (common to rat and human) of an inventive peptide.

[SEQ ID NO: 36]
This represents the partial amino acid sequence (21 residues from N-terminal) of a mature protein (common to rat and human) of an inventive peptide.

[SEQ ID NO: 37]
This represents the amino acid sequence of a precursor protein of a (rat) mature protein of an inventive peptide.

[SEQ ID NO: 38]
This represents the amino acid sequence of a precursor protein of a (human) mature protein of an inventive peptide.

[SEQ ID NO: 39]
This represents the cDNA sequence encoding a (rat) mature protein of an inventive peptide.

[SEQ ID NO: 40]
This represents the cDNA sequence encoding a (human) mature protein of an inventive peptide.

[SEQ ID NO: 41]
This represents the cDNA sequence encoding a precursor protein of a (rat) mature protein of an inventive peptide.

[SEQ ID NO: 42]
This represents the cDNA sequence encoding a precursor protein of a (human) mature protein of an inventive peptide.

[SEQ ID NO: 43]
This represents the partial amino acid sequence (30 residue from N-terminal) of a (porcine) mature protein of an inventive peptide.

[SEQ ID NO: 44]
This represents the amino acid sequence of a peptide as an immunogen employed in Example 9.

[SEQ ID NO: 45]
This represents the DNA sequence of an EcoRI/BglII digestion fragment of plasmid pGR2PL6 employed in Example 18.

[SEQ ID NO: 46]
This represents the DNA sequence of primer pGAL1-1F employed in Example 18.

[SEQ ID NO: 47]
This represents the DNA sequence of primer pGAL88-1R employed in Example 18.

[SEQ ID NO: 48]
This represents the DNA sequence of primer F/R120 employed in Example 19.

[SEQ ID NO: 49]
This represents the DNA sequence of primer R/R120 employed in Example 19.

[SEQ ID NO: 50]
This represents the cDNA sequence obtained as a result of a PCR in Example 19.

[SEQ ID NO: 51]
This represents the DNA sequence of primer 1F/H120 employed in Example 19.

[SEQ ID NO: 52]
This represents the DNA sequence of primer 1R/H120 employed in Example 19.

[SEQ ID NO: 53]
This represents the DNA sequence of primer 1F/H470 employed in Example 19.

[SEQ ID NO: 54]
This represents the DNA sequence of primer 1R/H470 employed in Example 19.

[SEQ ID NO: 55]
This represents the DNA sequence of primer 1 employed in Example 20.

[SEQ ID NO: 56]
This represents the cDNA sequence of primer 2 employed in Example 20.

[SEQ ID NO: 57]

This represents the DNA sequence of primer 3 employed in Example 20.

[SEQ ID NO: 58]

This represents the DNA sequence of primer 4 employed in Example 20.

[SEQ ID NO: 59]

This represents the synthetic DNA sequence employed in Example 21.

[SEQ ID NO: 60]

This represents the synthetic DNA sequence employed in Example 21.

[SEQ ID NO: 61]

This represents the amino acid sequence of rat galanin (rat galanin is represented by SEQ ID NO: 61 whose C-terminal is amidated).

A transformant *Escherichia coli* TOP10/p GR2PL6 obtained in Example 5 described below has been deposited to Institute for Fermentation, Osaka (IFO) on Aug. 21, 1998 under the deposition No. IFO 16201 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Sep. 4, 1998 under the deposition No. FERM BP-6486.

A transformant *Escherichia coli* TOP10/p GR2HL14 obtained in Example 19 described below has been deposited to Institute for Fermentation, Osaka (IFO) on Feb. 5, 1999 under the deposition No. IFO 16256 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Feb. 22, 1999 under the deposition No. FERM BP-6657.

A transformant *Escherichia coli* TOP10/p GR2RL4 obtained in Example 18 described below has been deposited to Institute for Fermentation, Osaka (IFO) on Feb. 5, 1999 under the deposition No. IFO 16257 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Feb. 22, 1999 under the deposition No. FERM BP-6658.

A transformant *Escherichia coli* MM294(DE3)/pTFC-GAL obtained in Example 21 described below has been deposited to Institute for Fermentation, Osaka (IFO) on Feb. 26, 1999 under the deposition No. IFO 16260 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Mar. 10, 1999 under the deposition No. FERM BP-6678.

A transformant *Escherichia coli* MM294(DE3)/pTB960-11 employed in Example 21 described below has been deposited to Institute for Fermentation, Osaka (IFO) on Jun. 25, 1997 under the deposition No. IFO 16100 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Jun. 15, 1998 under the deposition No. FERM BP-6388.

A transformant *Escherichia coli* MM294(DE3)/pTCIId23-MPIF1 employed in Example 21 described below has been deposited to Institute for Fermentation, Osaka (IFO) on Oct. 27, 1998 under the deposition No. IFO 16212 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Nov. 23, 1998 under the deposition No. FERM BP-6582.

GR2-1N employed in Example 13 described below has been deposited to Institute for Fermentation, Osaka (IFO) on Mar. 11, 1999 under the deposition No. IFO 50515 and to National Institute of Bioscience and Human Technology of Agency of Industrial Science and Technology of the Ministry of International Trade and Industry (NIBH, 1-1-3, Higashi, Tsukuba-City, Ibaragi Pref. Japan) on Mar. 17, 1999 under the deposition No. FERM BP-6682.

The present invention is described in more detail in the following examples, which are not intended to restrict the invention.

EXAMPLE 1

Detection of Galanin Receptor (GALR1, GALR2) Activating Effect (1-1) Construction of Rat Galanin Receptor (GALR1, GALR2)-Expressing Cell In order to obtain a rat GALR2 gene, 2 µl of a rat hypothalamic cDNA (CLONTECH), each 1 µl of 10 µM primer 1 (5'-GTCGACATGAATGGCTCCGGCAGCCAG-3', SEQ ID NO: 18) and primer 2 (5'-ACTAGTTTAA-CAAGCCGGATCCAGGGTTCTAC-3', SEQ ID NO: 19), 5 µl of a 10-fold concentrated buffer solution (attached to Klen Taq Polymerase, CLONTECH), 1 µl of 10 mM deoxynucleotide mixture (Invitrogen), 1 µl of Klen Taq DNA Polymerase (CLONTECH) and 39 µl of a distilled water for injection (OTSUKA PHARMACEUTICAL) were mixed to prepare a PCR solution. A PCR was performed using a Gene Amp PCR System 9700 (PERKIN ELMER) and involved [1] 1 cycle of 5 minutes at 95° C., [2] 3 cycles of 30 seconds at 95° C. followed by 15 seconds at 76° C. followed by 2 minutes at 72° C., [3] 3 cycles of 30 seconds at 95° C. followed by 15 seconds at 72° C. followed by 2 minutes at 72° C., [4] 3 cycles of 30 seconds at 95° C. followed by 15 seconds at 68° C. followed by 2 minutes at 72° C., [5] 3 cycles of 30 seconds at 95° C. followed by 15 seconds at 64° C. followed by 2 minutes at 72° C., [6] 3 cycles of 30 seconds at 95° C. followed by 15 seconds at 60° C. followed by 2 minutes at 72° C. and [7] 20 cycles of 30 seconds at 95° C. followed by 15 seconds at 56° C. followed by 2 minutes at 72° C. 10 µl of the solution after this PCR was subjected to an electrophoresis on a 1% low melting point agarose gel (Sea Plaque GTG:FTN) and the PCR products were identified by an ethidium bromide staining. A DNA band at about 1.2 kbp obtained as a PCR product was recovered from the agarose gel by a known method. Thus, an agarose gel piece was transferred to a 0.5 ml sampling tube and melted by heating at 70° C., and then equilibrated at 40° C., and then combined with 0.5 µl of beta-agarase (NIPPON GENE) to effect a reaction for 60 minutes, whereby degrading the agarose. The desired DNA fragment was recovered from the reaction mixture by a known ethanol precipitation method and ligated with a PCR-SCRIPT (STRATAGENE) plasmid vector. The reaction mixture was added to a Competent High (JM109: TOYOBO) to effect a transformation, and then incubated overnight in a 100 µg/ml ampicillin-supplemented LD agar medium (WAKO PURE CHEMICAL). The colonies formed on the medium were examined for the presence of the insertion of the intended DNA fragment by means of a colony-PCR method. A colony having an inserted DNA fragment was incubated overnight in a 100 µg/ml ampicillin-supplemented LD medium (WAKO PURE CHEMICAL) and then from the culture a plasmid having an inserted DNA fragment was recovered using a Plasmid Mini Kit (QIAGEN). A reaction for the base sequencing was performed using a Dye primer cycle sequencing ready reaction (ABI) and it was revealed, on the basis of the base sequencing using a fluorescent automatic sequencer, that the inserted DNA fragment in the plasmid was a DNA encoding GALR2 of 1119 bp.

The method described in Example 4 in JP-A-7-304797 was employed to prepare an expression vector pAKKO-1.11 for an animal cell. By a known method, a GALR2-encoding DNA fragment was recovered from this plasmid, ligated to a vector pAKKO-1.11, transduced into an E. coli DH5α, whereby obtaining a transformant. This transformant was incubated to produce a plasmid containing a DNA encoding GALR2.

This plasmid was transduced into a CHO cell according to the procedure described below using a CellPhect Transfection Kit (Pharmacia) to obtain an intended GALR2-expressing cell. Thus, 9.6 mg of a plasmid DNA dissolved in 240 µl of distilled water was combined with 240 µl of Buffer A (attached to CellPhect Transfection Kit), stirred, allowed to stand for 10 minutes, combined with 480 µl of Buffer B (attached to CellPhect Transfection Kit), stirred vigorously to form a liposome containing the DNA. $4 \times 10^5$ cells of CHO/dhfr$^-$ cell (obtained from ATCC) were inoculated to a petri dish, incubated in a 10% fetal calf serum (BIO WHITTAKER)-supplemented Ham's F-12 medium (NISSUI SEIYAKU) at 37° C. under a 5% $CO_2$ for 2 days, and then 480 µl of this liposome was added dropwise to the cell on the petri dish. The cell was incubated at 37° C. under a 5% $CO_2$ for 6 hours, and then washed twice with a serum-free Ham's F-12 medium, and then 3 ml of a 15% glycerol was added onto the cell on the petri dish, which was thus treated for 2 minutes. After washing further twice with a serum-free Ham's F-12 medium, the cell was incubated in a 10% fetal calf serum-supplemented Ham's F-12 medium at 37° C. under a 5% $CO_2$ for 15 hours. The cell was distributed by a trypsin treatment and recovered from the petri dish, and $1.25 \times 10^4$ cells were inoculated to a 6-well plate, which was subjected to an incubation in a dialyzed 10% fetal calf serum (JRH BIOSCIENCES)-supplemented Dulbecco's modified Eagle medium (DMEM) (NISSUI SEIYAKU) at 37° C. under a 5% $CO_2$. Since a plasmid-transduced transformant CHO cell was grown in this medium but a non-transduced cell was eradicated gradually, the culture medium was replaced on the 1st and 2nd days of the incubation to eliminate the dead cells. 8 Days after initiating the incubation, 20 colonies of a grown transformant CHO cell (20 types of the CHO cell clones) were selected. Each selected cell (20 types of the CHO cell clones) was recovered and formulated into a cell fraction by the method used in Example (1-2) described below. The level of the binding of a porcine $^{125}$I-galanin (New England Nuclear) to the membrane fraction was determined by a known method (e.g., method described in an example of EP-0711830A) and a strain expressing GALR2 at a high level was selected and subjected to the subsequent experiments.

A GALR1-encoding cDNA was obtained in a manner similar to that employed for obtaining a GALR2-encoding cDNA described above. Using primers 3 and 4 together with a brain cDNA library (CLONTECH), a PCR was performed to obtain a rat GALR1 cDNA of 1486 bp, which was inserted into pUC119 (TAKARA SHUZO), which was then designated as plasmid pRGR2.

This plasmid was double-digested with EcoRI and PstI to obtain a cDNA fragment, which was integrated into an expression plasmid vector for an animal cell, namely, pcDNA I (Invitrogen), at the site which was double-digested with EcoRI and NsiI, which was then designated as plasmid pRGRPC. This plasmid pRGRPC was double-digested with Hind III and Xba I to obtain a cDNA fragment, which was integrated into an expression plasmid vector for an animal cell, namely, pRC/CMV (Invitrogen), which was double-digested with Hind III and Xba I, whereby obtaining a rat GALR1 cDNA-expressing plasmid pRGR 1.

A known calcium phosphate method using CellPhect Transfection Kit (Pharmacia) was employed to transduce the rat GALR1 cDNA-expressing plasmid pRGR 1 into a CHO—KI cell (obtained from ATCC) which had been incubated in a Ham's F12 medium (NISSUI SEIYAKU), and finally 24 clones which were resistant to G-418 at 500 µg/ml were isolated using a stainless steel cylinder. A part of the cells of the 24 clones thus isolated were inoculated to a 6-well plate, and incubated until confluent, and then examined for the binding to 100 pM porcine• $^{125}$I-galanin (New England Nuclear) (for example by the method described in an example in EP-0711830A) to investigate the level of the expression of a rat galanine receptor by 24 clones. As a result, Cell No. 3 exhibited the highest porcine• $^{125}$I-galanin binding activity, suggesting the highest GALR1 expression level. Accordingly, a limiting dilution method was employed to inoculate 2 wells of a 96-well microplate with a single cell, from which the proliferation was effected. From indiviuallized cells, 12 clone cells were isolated and a part of them were subjected to the similar binding test again. As a result, Clone Cell No. 3-10 was selected to be used as a GALR1-expressing cell thereafter since it was considered to have the highest $^{125}$I-porcine galanin binding activity and to exhibit the highest GALR1 expression level.

(1-2) Preparation of Galanin Receptor (GALR1, GALR2)-Expressing Cell Membrane Fraction A GALR2-expressing cell obtained in Section (1-1) described above was incubated until sub-confluent (80 to 90% confluent) in a Dulbecco's modifier Eagle medium containing 10% fetal calf serum, glutamine, penicillin and streptomycin. After the incubation, the cell was combined with and suspended in a phosphate buffer containing 2.7 mM ethylene diamine N,N,N',N'-tetraacetic acid (EDTA) [2.7 mM EDTA/Phosphate-buffer saline (138 mM NaCl, 2.7 mM KCl, 8 mM $Na_2HPO_4$, 1 mM $KH_2PO_4$) to be released from the incubator and then recovered by a centrifugation. The cell was homogenized in a buffer of 10 mM sodium hydrogen carbonate and 5 mM EDTA (pH 7.3) containing a protease inhibitor mixture (final concentrations of 0.5 mM phenylmethylsulfonyl fluoride, 20 µg/ml leupeptin, 4 µg/ml E-64, 10 µg/ml pepstatin) using a POLYTRON HOMOGENIZER. The homogenate was centrifuged at 2500 rpm for 10 minutes using a high speed centrifuge (CR26H, Rotor Model RR24A: HITACHI) to obtain a supernatant, which was then ultracentrifuged (SCP70H, Rotor Model RR42: HITACHI) at 30,000 rpm for 1 hour to obtain a pellet. This pellet was suspended again in a buffer of 10 mM sodium hydrogen carbonate and 5 mM EDTA (pH 7.3) containing a protease inhibitor mixture (0.5 mM phenylmethylsulfonyl fluoride, 20 µg/ml leupeptine, 4 µg/ml E-64, 10 µg/ml pepstatin), and used as a membrane fraction for detecting a galanin receptor activating effect (stored at −70° C.).

(1-3) Detection of Galanin Receptor Activating Effect by [$^{35}$S]GTPγS Binding Test The membrane fraction prepared in Section (1-2) described above was suspended at 40 μg/ml (for GALR1 membrane fraction) or at 32 μg/ml (for GALR2 membrane fraction) in a 50 mM tris-buffer (pH 7.4) containing 1 μM guanosin-5'-diphosphate (GDP), 0.1% bovine serum albumin (BSA), 5 mM MgCl$_2$ and 150 mM NaCl, and each 0.2 ml was dispensed into a small polypropylene tube (Falcon 2053). The membrane fraction thus dispensed was combined with 2 μl of 50 nM [$^{35}$S]GTPγS (New England Nuclear) and 2 μl of porcine galanin as an agonist (at 100 μM, 10 μM, 1 μM, 100 nM, 10 nM, 1 nM, 100 pM or 10 pM), and the mixture was reacted at 25° C. for 60 minutes. This reaction mixture was combined with 1.5 ml of a 50 mM tris buffer (pH 7.4) containing 0.05% 3-[(3-cholamidopropyl)dimethylammonio]propanesulfonic acid (CHAPS), 0.1% BSA, 5 mM MgCl$_2$, 1 mM EDTA and filtered through a GF/F glass fiber filter (Watmann). This filter was washed with 1.5 ml of the same buffer, dried and then examined for its radioactivity using a liquid scintillation counter.

As a result, a galanin concentration-dependent increase in the [$^{35}$S]GTPγS binding level [FIG. 1], revealing that this method is capable of determining the galanin receptor agonist activity.

An EC50 level of rat galanin (concentration providing a half of the maximum binding level) was about 3 nM for GALR1 and was about 10 nM for GALR2.

EXAMPLE 2

Screening for GALR2 (Galanin Receptor Type 2)-Activating Compounds (2-1) Preparation of Porcine Hypothalamic Extract Within 3 hours after purchasing porcine hypothalami from TOKYO SHIBAURA ZOKI, the following procedure was completed to obtain an extract.

First, 35 porcine hypothalami (about 500 g) were cut by a knife into small pieces, which were placed in a 3000 ml beaker containing 1250 ml of a boiling distilled water and boiled for 10 minutes. The hypothalamic preparation after boiling was cooled on a water bath followed by an ice bath while still being contained in the beaker, whereby cooling to about 4° C. This hypothalamic preparation was combined with the distilled water employed in the boiling and then homogenized for 10 minutes using a POLYTRON HOMOGENIZER. The homogenate thus obtained was treated dropwise with 90 ml of acetic acid at the final concentration of 1 M, and then stirred for 1 hour. The homogenate was centrifuged at 10,000 rpm for 30 minutes using a high speed centrifuge (CR26H, Rotor Model RR10A, HITACHI) to obtain a supernatant (1). On the other hand, the pellet obtained after the centrifugation was combined again with 2000 ml of 1M acetic acid and then homogenized for 10 minutes using a POLYTRON HOMOGENIZER. This homogenate was stirred overnight (for about 16 hours) using a stirring fin and then homogenized for 10 minutes using a POLYTRON HOMOGENIZER to obtain a supernatant (2). Supernatants (1) and (2) were mixed, and combined with 2 volumes of acetone, stirred at 4° C. for 1 hour, then centrifuged at 10,000 rpm for 15 minutes using a high speed centrifuge (CR26H, Rotor Model RR10A, HITACHI) to obtain a supernatant. The supernatant thus obtained was subjected to a rotary evaporator to remove acetone, and concentrated finally to the volume of 4000 ml. This concentrate was centrifuged at 35,000 rpm for 1 hour using an ultracentrifuge (SCP70H, Rotor Hitachi Model RPZ35T, HITACHI) to obtain a clear supernatant. Each 1000 ml of the supernatant thus obtained was combined with 500 ml of diethylether and mixed vigorously in a separation funnel and then allowed to separate into 2 phases, whereby obtaining an aqueous phase. This aqueous phase was concentrated on a rotary evaporator to the volume of 1000 ml, whereby yielding a final extract.

(2-2) Purification of Porcine Hypothalmic Extract by Octadodecyl Reverse Chromatography An octadodecylated silica gel ODS-AM 120-S50 (YMC) was swollen with methanol and then packed into a glass column ume of 5 cm in diameter to the volume of 130 ml, which was then equilibrated with 1M acetic acid. To this column, the extract (corresponding to 500 g of the hypothalami) prepared in Step (2-1) was loaded at the flow rate of 400 ml/h. Subsequently, this column was eluted with about 500 ml of 1M acetic acid followed by about 500 ml of 20% acetonitrile/0.1% trifluoroacetic acid at the flow rate of 400 ml/h, whereby washing the gel. Finally, this column was eluted with about 500 ml 50% acetonitrile/0.1% trifluoroacetic acid at the flow rate of 400 ml/h, whereby eluting an intended crude peptide component. The extract thus obtained was concentrated on a rotary evaporator and then lyophilized by a freeze drier (12EL, VirTis).

(2-3) Purification of Porcine Hypothalmic Extract by TSKgel ODS80™ Reverse Phase High Performance Liquid Chromatography A TSKgel ODS80™ reverse phase high performance liquid chromatography column (TOSOH, 22.5 mm×30 cm) was eluted with Solvent A (0.1% trifluoroacetic acid/distilled water) at the flow rate of 8 ml/min to be equilibrated. A lyophilized material obtained in Step (2-2) described above was dissolved in 40 ml of 1M acetic acid, and four 10 ml aliquots were subjected to the chromatography. Thus, 10 ml of a solution of the lyophilized material in acetic acid was loaded on the column, which was then eluted at 8 ml/min over 60 min with a linear gradient from 80% by volume of Solvent A (0.1% trifluoroacetic acid/distilled water)/20% by volume of Solvent B (0.1% trifluoroacetic acid/100% acetonitrile) to 40% by volume of Solvent A (0.1% trifluoroacetic acid/distilled water)/60% by volume of Solvent B (0.1% trifluoroacetic acid/100% acetonitrile).

The effluent was collected in 8 ml aliquots each of which was designated by Fraction No., which was dispensed in 1 ml aliquots and concentrated into dryness using a vacuum concentrating machine (Savant). The dried material thus obtained was dissolved in 0.03 ml of dimethyl sulfoxide and used as an assay sample for determining the GALR1 and GALR2 activating effects.

(2-4) Isolation and Purification of GALR2 (Galanin Receptor Type 2)-Activating Compounds by [$^{35}$S]GTPγS Binding Test An assay sample obtained in Step (2-3) described above was examined for the galanin receptor activating effect by the [$^{35}$S]GTPγS binding test using GALR1 or GALR2 membrane fraction described in Step (1-3) described above.

Figure 2:
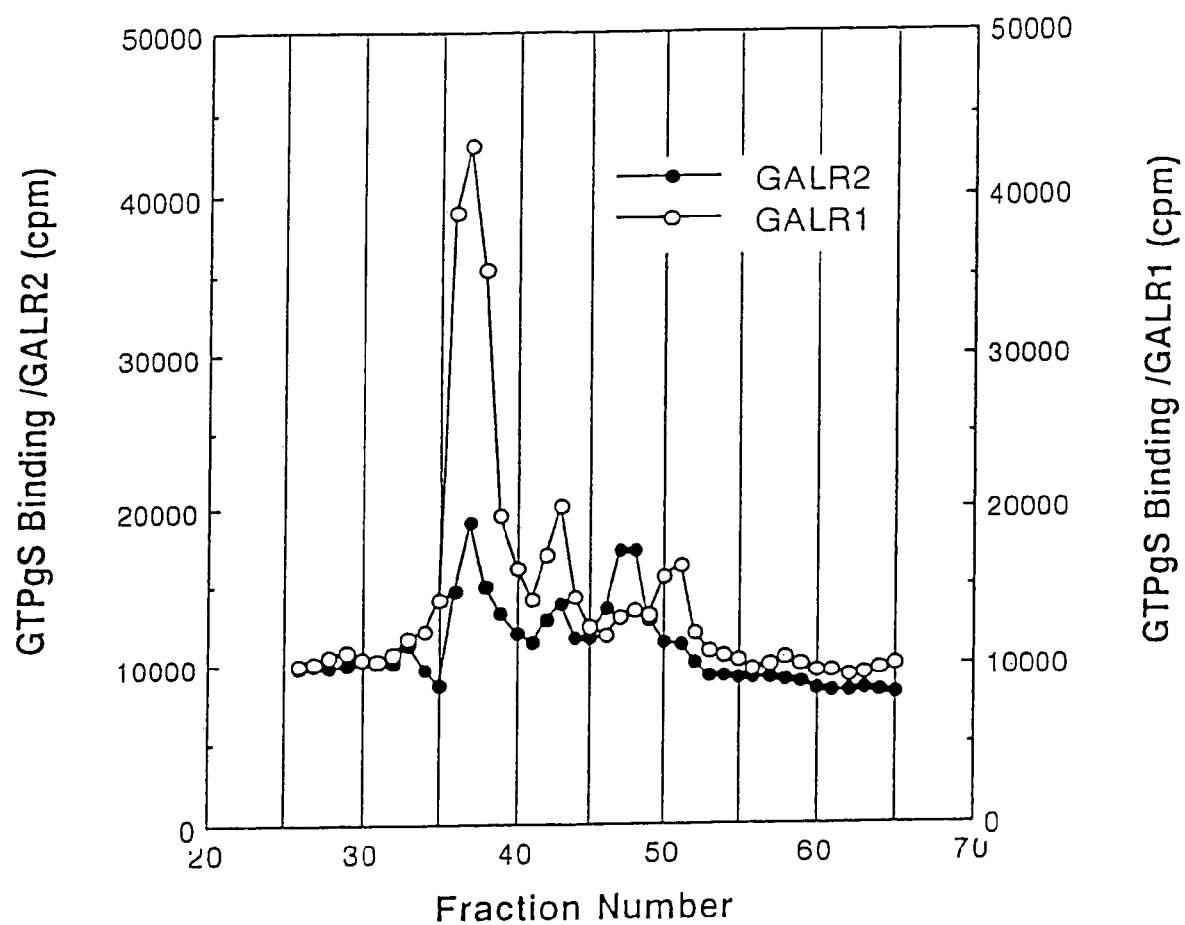
FIG. 2 shows the results of [$^{35}$S]GTPγS binding test using a GALR2-expressing cell membrane fraction in the sample fractions obtained in Example 2 (2-3).

Fraction Nos. 36 to 39 and Nos. 42 to 43 exhibited a [$^{35}$S]GTPγS binding-promoting effect in the [$^{35}$S]GTPγS binding test using a GALR1-expressing cell membrane fraction, while Fraction Nos. 36 to 39, Nos. 42 to 43 and Nos. 46 to 49 exhibited a [$^{35}$S]GTPγS binding-promoting effect in the [$^{35}$S]GTPγS binding test using a GALR2-expressing cell membrane fraction [FIG. 2].

Figure 3:
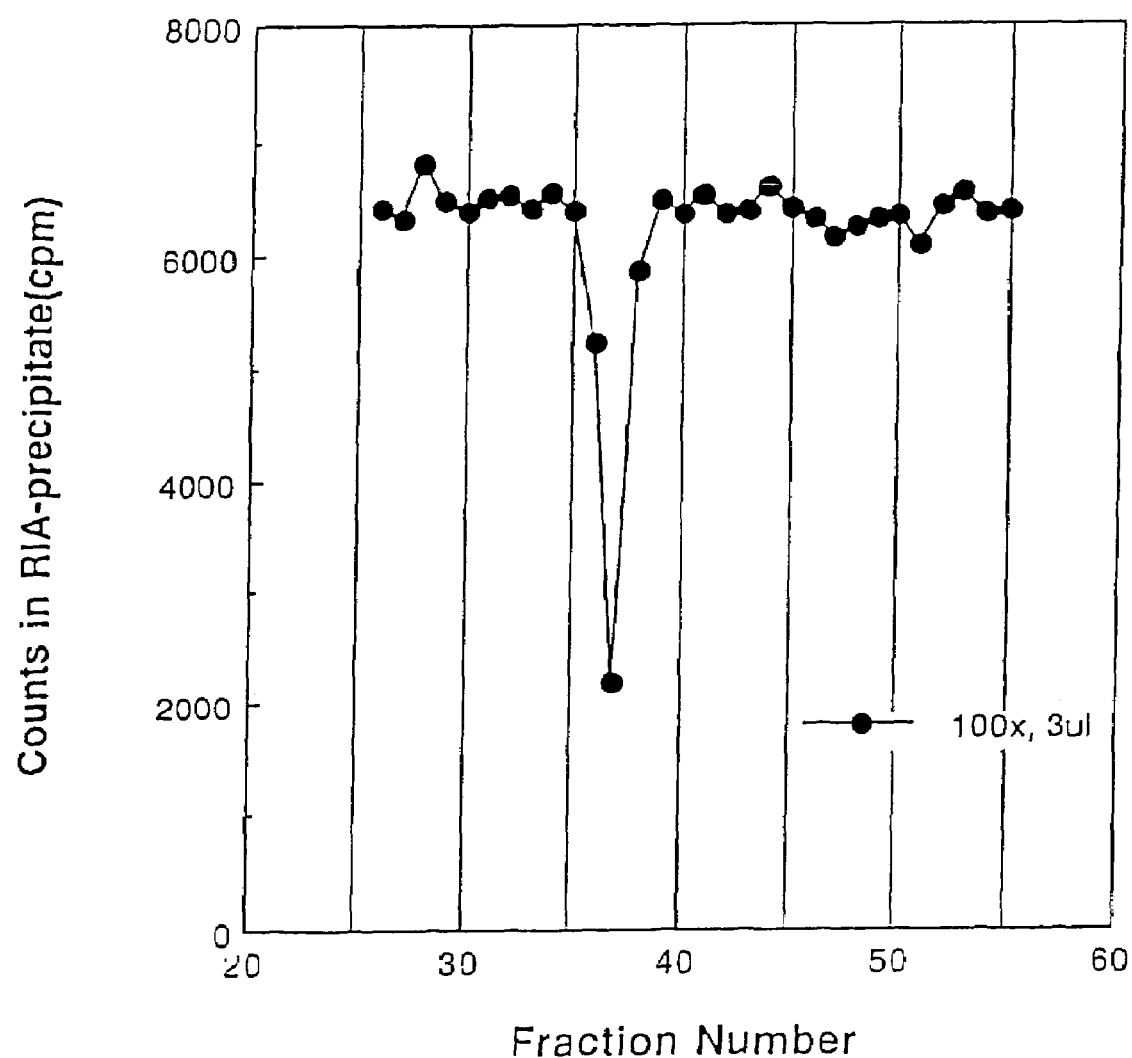
FIG. 3 shows the results of the analysis of a sample fraction obtained in Example 2 (2-3) using a porcine galanin radioimmunoassay kit (Peninsula).

When an assay sample was subjected to a 100-fold dilution with dimethyl sulfoxide and 3 ml of the diluted sample was analyzed by a porcine galanin radioimmunoassay kit (Peninsula), the results indicated a galanin immune activity in Fraction Nos. 36 to 38 [FIG. 3].

Based on the results described above, the component having the GALR1- and GALR2-activating effects in Fraction Nos. 36 to 39 were judged to be porcine galanin. On the other hand, the component having the GALR2-activating effect in Fraction Nos. 46 to 49 were assumed to be a compound different from porcine galanin.

(2-5) Determination of Molecular Weight of GALR2 (Galanin Receptor Type 2)-Activating Compound By means of a known gel filtration high performance liquid chromatography, the molecular weight of the GALR2-activating component (Fraction Nos. 46 to 49) obtained in Step (2-4) described above was determined.

Zero point zero two milliliter of a sample mixture of Fraction Nos. 46 to 49 was diluted with 0.08 ml of 0.1% trifluoroacetic acid/distilled water, and a 0.05 ml aliquot was loaded onto a G2000SWXL (TOSOH) column, which was eluted with 0.1% trifluoroacetic acid/10% acetonitrile at 0.5 ml/min and the effluent was collected in 0.25 ml aliquots (at an interval of 0.5 minutes). The fractions thus obtained were concentrated into dryness (SpeedVac Plus SC210A; Savant) and dissolved directly in a suspension of the membrane fraction, which was then supplemented with 2 μL of 50 nM [$^{35}$S]GTPγS (New England Nuclear) and examined for the [$^{35}$S]GTPγS binding level thereafter by the method described in Step (1-3).

Figure 4:
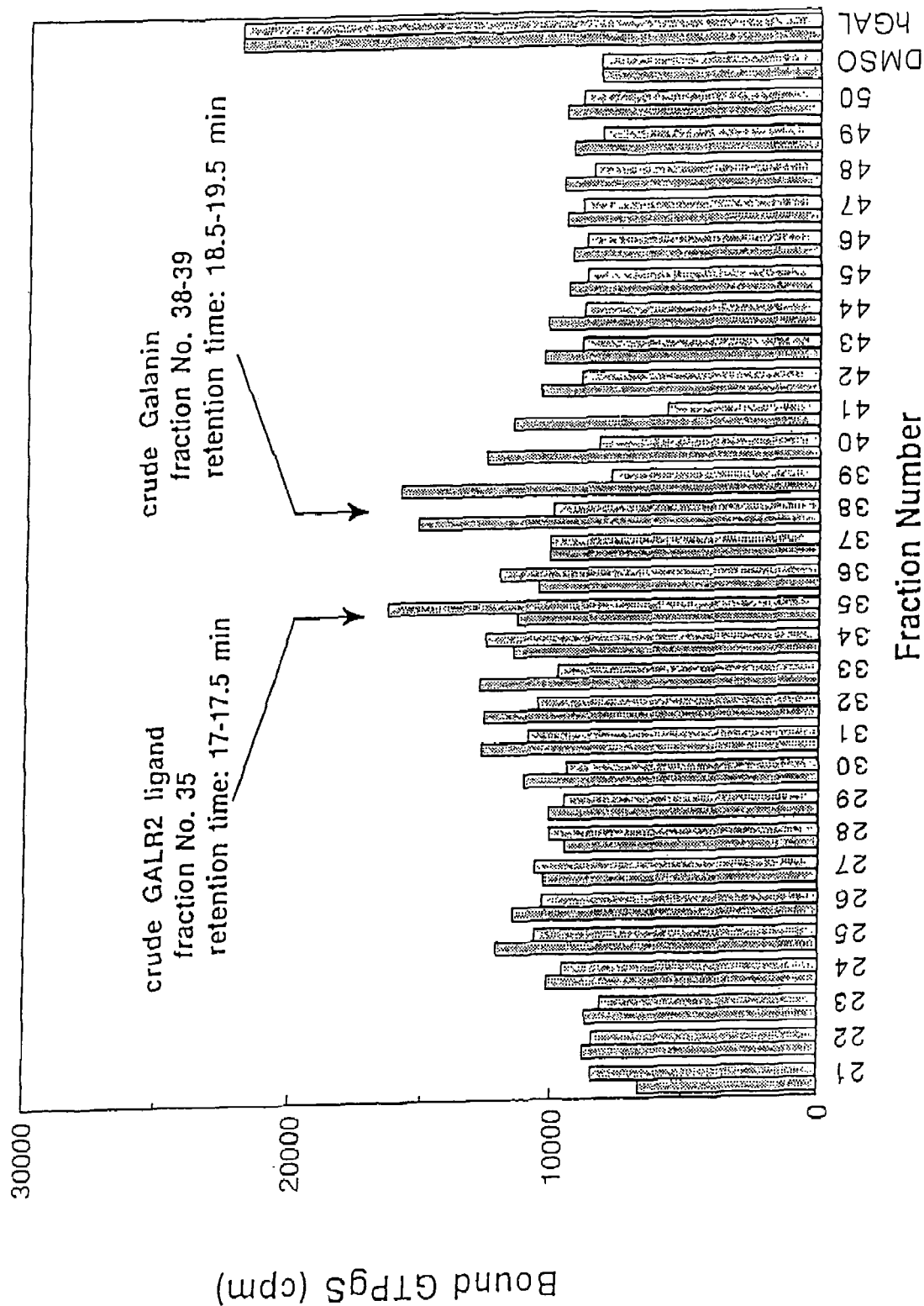
FIG. 4 shows the molecular weight of a component having a GALR2 activating effect ([$^{35}$S]GTPγS binding promoting effect) obtained in Example 2 (2-4) when determined by a gel filtration HPLC.
Figure 5:
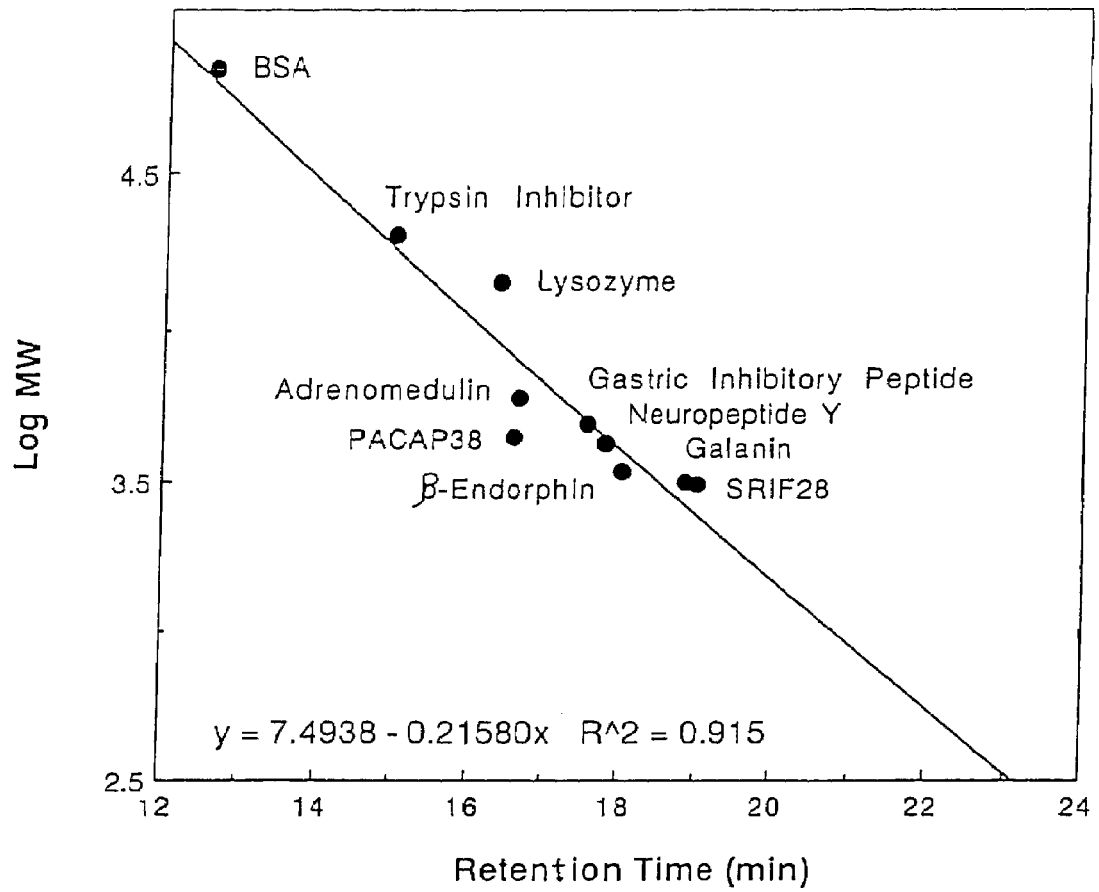
FIG. 5 shows the molecular weight of a known peptide in Example 2 (2-4) when determined by a gel filtration HPLC.

As a result, the component having a GALR2-activating effect ([$^{35}$S]GTPγS binding-promoting effect) was eluted into Fraction No. 35 (retention time: 17 to 17.5 minutes) [FIG. 4]. A comparison and an investigation using known peptides which were analyzed in the same conditions (adrenomedulin, gastric inhibitory peptide, PACAP38, neuropeptide Y, β-endorphine, galanin, SRIF28 (Somatostatin 28), bovin serum albumin, trypsin inhibitor lysozyme) [FIG. 5] revealed the molecular weight of the component having the GALR2-activating effect in Fraction Nos. 46 to 49 was assumed to be about 5000 to about 7000.

On the other hand, the molecular weight of known porcine galanin (PEPTIDE KENKYUSHO) is 3157.4 (retention time: 18.858 minutes). Accordingly, it was suggested that the component having the GALR2-activating effect in Fraction Nos. 46 to 49 was a substance different from known galanin.

EXAMPLE 3

Purification of Compound having GALR2 (Galanin Receptor Type 2)-Activating Effect (3-1) Preparation of Porcine Hypothalamic Extract In order to prepare a large amount of a hypothalamic extract, the method in Step (2-1) described above was simplified as described below.

Fifty frozen porcine hypothalami (TOKYO SHIBAURA ZOKI) (about 1 kg) were cut by a knife into thin slices, which were placed in a 5000 ml beaker containing 2500 ml of a boiling distilled water and boiled for 10 minutes. The hypothalamic preparation after boiling was cooled on a water bath followed by an ice bath while still being contained in the beaker, whereby cooling to about 4° C., and then was combined with the distilled water employed in the boiling and then homogenized for 10 minutes using a POLYTRON HOMOGENIZER. The homogenate thus obtained was treated dropwise with 150 ml of acetic acid and 8 ml of 6N hydrochloric acid at the final concentrations of 1 M and 20 mM, respectively, and then stirred overnight (about 16 hours) using a stirring fin. The homogenate was centrifuged at 8000 rpm for 30 minutes using a high speed centrifuge (CR26H, Rotor Model RR10A, HITACHI) to obtain a supernatant, which was filtered through a gauze to remove any lipid debris. This procedure was repeated 4 times to prepare an extract from about 4 kg of the hypothalami.

(3-2) Concentration and Crude Fractionation of Porcine Hypothalamic Extract (3-2-1) Purification by Octadodecyl Reverse Phase Chromatography An octadodecylated silica gel (YMC, ODS-AM 120-S50 was swollen with methanol and then packed into a glass column of 5 cm in diameter to the volume of 400 ml, which was then equilibrated with 1M acetic acid.

To this column, a half of the extract (corresponding to 2 kg of the hypothalami) prepared in Step (3-1) was loaded at the flow rate of 400 ml/h. Subsequently, this column was eluted with about 1000 ml of 1M acetic acid followed by about 1200 ml of 20% acetonitrile/0.1% trifluoroacetic acid at the flow rate of 400 ml/h, whereby washing the gel. Finally, this column was eluted with about 2000 ml 60% acetonitrile/0.1% trifluoroacetic acid at the flow rate of 400 ml/h, whereby eluting an intended crude peptide fraction. The extract thus obtained was concentrated on an evaporator and then lyophilized by a freeze drier (12EL, VirTis). This procedure was repeated twice to prepare a lyophilized powder of the hypothalamic extract corresponding to about 4 kg (200 organs).

(3-2-2) Purification by SP-Sephadex Ion Exchange Chromatography

An SP-Sephadex C25 (Pharmacia Biotech) swollen with 10 mM hydrochloric acid was packed into a glass column 5 cm in diameter to the volume of 120 ml, which was washed with 100 mM hydrochloric acid then equilibrated with 1M acetic acid. The lyophilized powder of the hypothalamic extract obtained in Step (3-2-1) was dissolved in about 800 ml of 1M acetic acid and loaded onto an equilibrated SP-Sephadex C25 column at the flow rate of 400 ml/h, and eluted sequentially with about 600 ml of 1M acetic acid, about 600 ml of 1M pyridine and then about 600 ml of 1M pyridine- acetic acid (pH 5.0) at the flow rate of 400 ml/h, and the effluent was collected in 40 ml aliquots, which were dispensed in 0.2 ml aliquots and concentrated into dryness using a vacuum concentrating machine (Savant). The dried material thus obtained was dissolved in 0.04 ml of dimethyl sulfoxide and examined for the GALR2-activating effect by the method in Step (1-3) described above.

As a result, it was revealed that an intended component having the GALR2-activating effect was eluted with 1M pyridine• acetic acid (pH 5.0). These results suggested that the component (compound) having the GALR2-activating effect was a strongly basic substance.

(3-2-3) Purification by Sephadex G50 Gel Filtration Chromatography

A fraction eluted with 1M pyridine• acetic acid (pH 5.0) obtained in Step (3-2-2) described above was concentrated on an evaporator to 100 ml, which was loaded at the flow rate of 400 ml/h onto a Sephadex G50 (Pharmacia Biotech) column (6 cm in diameter, 3000 ml in volume) equilibrated with 1M acetic acid, and then eluted with 1M acetic acid at the flow rate of 400 ml/h, and then the effluent was collected in 33 ml aliquots each of which was designated by Fraction No., which was dispensed in 0.25 ml aliquots and concentrated into dryness using a vacuum concentrating machine (Savant). The dried material thus obtained was dissolved in 0.03 ml of dimethyl sulfoxide and examined for the GALR2-activating effect by the method in Step (1-3) described above.

As a result, it was revealed that an intended component having the GALR2-activating effect was eluted mainly in Fraction Nos. 66 to 80. A weak activity was noted also in Fraction Nos. 55 to 65 and Nos. 45 to 54. Each of Fraction Nos. 66 to 80, Nos. 55 to 65 and Nos. 45 to 54 was mixed and lyophilized.

(3-3) Purification of Compound having GALR2-Activating Effect using HPLC (3-3-1) Purification by TSKgel ODS80™ Reverse Phase High Performance Liquid Chromatography A TSKgel ODS80™ reverse phase high performance liquid chromatography column (TOSOH, 22.5 mm×30 cm) was eluted with Solvent A (0.1% trifluoroacetic acid/distilled water) at the flow rate of 4 ml/min at 40° C. to be equilibrated.

A lyophilized material of a Sephadex G50 fraction obtained in Step (3-2-3) described above was dissolved in 1M acetic acid, and loaded onto the column, and then eluted at the flow rate of 4 ml/min over 120 min with a linear gradient from 67% by volume of Solvent A (0.1% trifluoroacetic acid/distilled water)/33% by volume of Solvent B (0.1% trifluoroacetic acid/60% acetonitrile) to 100% by volume of Solvent B (0.1% trifluoroacetic acid/60% acetonitrile) to recover the effluent.

The effluent was collected in 8 ml aliquots each of which was designated by Fraction No. The lyophilized material of Fraction Nos. 66 to 80 was subjected to the chromatograpy in two portions, and each of Fraction Nos. 55 to 65 and Nos. 45 to 54 was chromatographed just once.

Four microliter of the fraction was used directly to examine the GALR2-activating effect by the method in Step (1-3) described above. As a result, every chromatography exhibited three active peaks. The retention time of the component having the acivating effect noted in Fraction Nos. 35 to 38 was almost in agreement with that of galanin described in Example 2. The activating component noted in Fraction Nos. 47 to 50 was almost in agreement with the retention time of the component having the GALR2-activating effect described in Example 2 (which did not activate GALR1 and was not detected by the porcine galanin radioimmunoassay kit described above). Accordingly, it was decided that Fraction Nos. 47 to 50 were used for the purification of the component having the GALR2-activating effect, and thus were combined and lyophilized.

(3-3-2) Purification by TSKgel CM-2SW Ion Exchange High Performance Liquid Chromatography A TSKgel CM-2SW ion exchange high performance liquid chromatography column (TOSOH, 0.46 cm×25 cm) was eluted at 20° C. at the flow rate of the flow rate of 1 ml/min with Solvent A (10 mM ammonium formate/40% acetonitrile) to be equilibrated.

A lyophilized material of a reverse phase high performance liquid chromatography fraction obtained in Step (3-3-1) described above was dissolved in Solvent A and loaded onto the column, and then eluted at 1 ml/min over 60 min with a linear gradient from 100% by volume of Solvent A (10 mM ammonium formate/40% acetonitrile) to 100% by volume of Solvent B (500 mM ammonium formate/40% acetonitrile) to recover the effluent.

The effluent was collected in 0.5 ml aliquots each of which was designated by Fraction No. One microliter of the fraction was used directly to examine the GALR2-activating effect by the method in Step (1-3) described above. As a result, a major active peak was detected in Fraction Nos. 89 to 92. These fractions were combined to subject a subsequent purification.

(3-3-3) Purification by Diphenyl Reverse Phase High Performance Liquid Chromatography A diphenyl reverse phase high performance liquid chromatography column (Vydak219TP54, 0.46 cm×25 cm) was eluted at 40° C. at the flow rate of the flow rate of 1 ml/min with Solvent A (0.1% trifluoroacetic acid/distilled water) to be equilibrated.

An ion exchange high performance liquid chromatography fraction obtained in Step (3-3-2) described above was loaded directly onto the column, and then eluted at 1 ml/min within 1 minute with 100% by volume of Solvent A (0.1% trifluoroacetic acid/distilled water) changed rapidly to 50% by volume of Solvent B (0.1% trifluoroacetic acid/60% acetonitrile) and then at the flow rate of 1 ml/min over 60 minutes with a linear gradient to 100% by volume of Solvent B to recover the effluent.

The effluent was collected in 1 ml aliquots each of which was designated by Fraction No. One microliter of the fraction was used directly to examine the GALR2-activating effect by the method in Step (1-3) described above. As a result, a major active peak was detected in Fraction Nos. 24 to 26. These fractions were combined to subject a subsequent purification.

(3-3-4) Purification by Super Phenyl Reverse Phase High Performance Liquid Chromatography A TSKgel super phenyl reverse phase high performance liquid chromatography column (TOSOH, 0.46 cm×10 cm) was eluted at 40° C. at the flow rate of 1 ml/min with Solvent A (0.1% trifluoroacetic acid/distilled water) to be equilibrated.

A diphenyl reverse phase high performance liquid chromatography fraction obtained in Step (3-3-3) described above was loaded directly onto the column, and then eluted at the flow rate of 1 ml/min within 1 minutes with 100% by volume of Solvent A (0.1% trifluoroacetic acid/distilled water) changed rapidly to 45% by volume of Solvent B (0.1% trifluoroacetic acid/60% acetonitrile) and then at the flow rate of 1 ml/min over 80 minutes with a linear gradient to 55% of Solvent B to recover the effluent.

The effluent was collected in 1 ml aliquots each of which was designated by Fraction No. One microliter of the fraction was used directly to examine the GALR2-activating effect by the method in Step (1-3) described above. As a result, a major active peak was detected in Fraction Nos. 44 to 45 and 50 to 52. Fraction Nos. 44 to 45 were combined and chromatographed again in the same conditions to obtain the effluent fractions as 0.5 ml aliquots. On the other hand, each of Fraction Nos. 50, 51 and 52 was chromatographed again individually in the same conditions to obtain the effluent fractions as 0.5 ml aliquots.

Two microliter of each fraction was used directly to examine the GALR2-activating effect by the method in Step (1-3) described above. As a result, an active peak was detected in Fraction Nos. 93 to 95 obtained by the second chromatography of Fraction Nos. 44 to 45 and in Fraction Nos. 105 to 107 obtained by the second chromatography of Fraction No. 50. The second chromatography of Fraction No. 51 revealed a major active peak in Fraction Nos. 105 to 107 and a weakly active peak in Fraction Nos. 108 to 109. In addition, the second chromatography of Fraction No. 52 revealed a broad major active peak in Fraction Nos. 106 to 110.

(3-3-5) Purification by Super ODS Reverse Phase High Performance Liquid Chromatography (3-3-5-1) Purification of Main GALR2-Activating Component (3-3-5-1-1) Chromatography in the Presence of Trifluoroacetic acid A TSKgel super ODS reverse phase high performance liquid chromatography column (TOSOH, 0.46 cm×10 cm) was eluted at 40° C. at the flow rate of 1 ml/min with Solvent A (0.1% trifluoroacetic acid/distilled water) to be equilibrated.

A super phenyl reverse phase high performance liquid chromatography fraction obtained in Step (3-3-4) described above was loaded directly onto the column, and then eluted at the flow rate of 1 ml/min within 1 minute with a linear gradient from 100% by volume of Solvent A (0.1% trifluoroacetic acid/distilled water) to 50% by volume of Solvent B (0.1% trifluoroacetic acid/60% acetonitrile) and then at the flow rate of 1 ml/min over 84 minutes with a linear gradient to 62.5% of Solvent B to recover the effluent.

The effluent was collected in 0.5 ml aliquots each of which was designated by Fraction No. Two microliter of the fraction was used directly to examine the GALR2-activating effect by the method in Step (1-3) described above. As a result, a major active peak was detected in Fraction Nos. 96 to 97.

The Fraction Nos. 96 to 97 were combined and chromatographed again in the same conditions to obtain the fractions as 0.5 ml aliquots. While a single peak was detected in a UV absorption spectrum at 210 nm, the peak had a shoulder which reflected the presence of impurities. Two microliter of each fraction was used directly to examine the GALR2-activating effect by the method in Step (1-3) described above. As a result, an active peak was detected in Fraction Nos. 98 to 100, and corresponded to the peak which was detected in the UV absorption spectrum at 210 nm but whose shoulder was eliminated this time. In order to remove the impurities corresponding to the shoulder of the peak, a further purification was conducted by the method described in Step (3-3-5-1-2).

(3-3-5-1-2) Chromatography in the Presence of Heptafluorobutyric Acid

A TSKgel super ODS reverse phase high performance liquid chromatography column (TOSOH, 0.46 cm×10 cm) was eluted at 40° C. at the flow rate of 1 ml/min with Solvent A (0.1% heptafluorobutyric acid/distilled water) to be equilibrated.

Fraction Nos. 98 to 100 obtained in Step (3-3-5-1-1) were loaded directly onto the column, and then eluted at the flow rate of 1 ml/min within 1 minutes with 100% by volume of Solvent A (0.1% heptafluorobutyric acid/distilled water) changed rapidly to 35% by volume of Solvent B (0.1% heptafluorobutyric acid/100% acetonitrile) and then at the flow rate of 1 ml/min over 60 minutes with a linear gradient to 50% of Solvent B to recover the effluent.

The effluent was collected in 0.5 ml aliquots each of which was designated by Fraction No. Two microliters of the fraction was used directly to examine the GALR2-activating effect by the method in Step (1-3) described above. As a result, an active peak was detected in Fraction Nos. 67 to 69. This active peak was in a complete agreement with the earlier UV absorption peak of the twin peaks at 210 nm, indicating a single purified peptide. This component having the activating effect was designated as a main GALR2-activating component.

(3-3-5-2) Purification of Auxiliary GALR2-Activating Component (1)

A TSKgel super ODS reverse phase high performance liquid chromatography column (TOSOH, 0.46 cm×10 cm) was eluted at 40° C. at the flow rate of 1 ml/min with Solvent A (0.1% heptafluorobutyric acid/distilled water) to be equilibrated.

The super phenyl reverse phase high performance liquid chromatography Fraction Nos. 105 to 107 (derived from Fraction No. 50), Fraction Nos. 105 to 107 (derived from Fraction No. 51) and Fraction Nos. 106 to 107 (derived from Fraction No. 52) obtained in Step (3-3-4) were mixed and loaded directly onto the column, and then eluted at the flow rate of 1 ml/min within 1 minute with 100% by volume of Solvent A (0.1% trifluoroacetic acid/distilled water) changed rapidly to 52.5% by volume of Solvent B (0.1% trifluoroacetic acid/60% acetonitrile) and then at the flow rate of 1 ml/min over 84 minutes with a linear gradient to 65% of Solvent B to recover the effluent. The effluent was collected in 0.5 ml aliquots each of which was designated by Fraction No.

Two microliters of the fraction was used directly to examine the GALR2-activating effect by the method in Step (1-3) described above. As a result, an active peak was detected in Fraction Nos. 75 to 76. Fraction Nos. 75 to 76 were mixed and chromatographed again in the same conditions to collect 0.5 ml aliquots each of which was designated by Fraction No. The effluent was detected as a single peak in the UV absorption spectrum at 210 nm. Three microliters of the fraction was used directly to examine the GALR2-activating effect by the method in Step (1-3) described above. As a result, an active peak was detected in Fraction Nos. 76 to 78. This active peak was in an agreement with the UV absorption peak at 210 nm, indicating a single purified peptide. This component having the activating effect was designated as an auxiliary GALR2-activating component (1).

(3-3-5-3) Purification of Auxiliary GALR2-Activating Component (2)

A TSKgel super ODS reverse phase high performance liquid chromatography column (TOSOH, 0.46 cm×10 cm) was eluted at 40° C. at the flow rate of 1 ml/min with Solvent A (0.1% heptafluorobutyric acid/distilled water) to be equilibrated.

The super phenyl reverse phase high performance liquid chromatography Fraction Nos. 108 to 109 (derived from Fraction No. 51) and Fraction Nos. 108 to 110 (derived from Fraction No. 52) obtained in Step (3-3-4) were mixed and loaded directly onto the column, and then eluted at the flow rate of 1 ml/min within 1 minute with 100% by volume of Solvent A changed rapidly to 52.5% by volume of Solvent B (0.1% trifluoroacetic acid/60% acetonitrile) and then at 1 ml/min over 84 minutes with a linear gradient to 65% of Solvent B to recover the effluent. The effluent was collected in 0.5 ml aliquots each of which was designated by Fraction No.

Two microliters of the fraction was used directly to examine the GALR2-activating effect by the method in Step (1-3) described above. As a result, an active peak was detected in Fraction Nos. 79 to 80.

Fraction Nos. 79 to 80 were mixed and chromatographed again in the same conditions to collect 0.5 ml aliquots, which were detected as a single peak in the UV absorption spectrum at 210 nm.

Three microliters of the fraction was used directly to examine the GALR2-activating effect by the method in Step (1-3) described above. As a result, a major active peak was detected in Fraction Nos. 79 to 81. This active peak was in a complete agreement with the UV absorption peak at 210 nm, indicating a single purified peptide. This component having the activating effect was designated as an auxiliary GALR2-activating component (2).

EXAMPLE 4

Amino Acid Sequencing (4-1) N-Terminal Amino Acid Sequencing of Main Component having GALR2-Activating Effect The main GALR2-activating component of Fraction Nos. 67 to 69 obtained in Step (3-3-5-1-2) described above was dissolved in 20 µl of 0.1% trifluoroacetic acid/30% acetonitrile and added dropwise to a peptide support disk (BECKMAN), which was then dried over a nitrogen gas. The disk was mounted on a protein sequencer (BECKMAN, LF3400DT) and an automatic Edman's degradation by a standard analysis (procedure 40) was performed to sequence the amino acid. Each cycle identified the PHT amino acid shown in Table 1.

TABLE 1

N-terminal amino acid sequence of main GALR2-activating component

| Cycle No. | PTH amino acid | Amount (pmol) |
|---|---|---|
| 1 | A | 131 |
| 2 | P | 89.9 |
| 3 | V | 138 |
| 4 | H | 81.7 |
| 5 | R | 47.3 |
| 6 | G | 92.1 |
| 7 | R | 45.6 |
| 8 | G | 72.9 |
| 9 | G | 78.2 |
| 10 | W | 24.1 |
| 11 | T | 24.0 |
| 12 | L | 51.5 |
| 13 | N | 34.0 |
| 14 | S* | 9.3 |
| 15 | A | 25.4 |
| 16 | G | 26.8 |
| 17 | Y | 24.6 |
| 18 | L | 32.4 |
| 19 | L | 43.5 |
| 20 | G | 24.0 |
| 21 | P | 14.6 |
| 22 | V | 17.2 |
| 23 | L | 26.4 |
| 24 | H | 1.4 |
| 25 | P | 16.1 |
| 26 | P | 22.6 |
| 27 | S* | 2.9 |
| 28 | X | |
| 29 | A | 11.1 |
| 30 | E | 3.8 |
| 31 | G | 13.0 |
| 32 | G | 19.6 |

TABLE 1-continued

N-terminal amino acid sequence of main GALR2-activating component

| Cycle No. | PTH amino acid | Amount (pmol) |
|---|---|---|
| 33 | G | 20.4 |
| 34 | K | 4.4 |

1) Raw data without correction for lag
2) S*: In addition to PTH-Ser, its degradation product (PTH-dehydroalanin-DTT adduct) was also detected.
3) No PTH amino acid was identified in the 28th cycle.

From Table 1, the amino acid sequence from the N-terminal to the 34th residue of the main GALR2-activating component was determined as shown below (the 28th residue X was unknown).

APVHRGRGGWTLNSAGYLLGPVLHPPSXAEGGGK
(N-terminal amino acid sequence of main GALR2-activating component: SEQ ID NO: 11)

The sequence consisting of 13 residues from the 9th residue to the 21st residue from the N-terminal of the amino acid sequence obtained was in agreement with the N-terminal amino acid sequence of known porcine galanin. However, the amino acid sequences in the adjacent regions were not in agreement with any of the sequences of the porcine galanin and its precursors.

Also since no known peptide in agreement with this amino acid sequence was found, the main GALR2-activating component obtained here was assumed to be a novel peptide.

(4-2) N-Terminal Amino Acid Sequencing of Auxiliary Component (1) having GALR2-Activating Effect The auxiliary GALR2-activating component in Fraction Nos. 76 to 78 obtained in Step (3-3-5-2) described above was analyzed similarly to Step (4-1).

Each cycle identified the amino acid shown in Table 2.

TABLE 2

N-terminal amino acid sequence of auxiliary activating component (1)

| Cycle No. | PTH amino acid | Amount (pmol) |
|---|---|---|
| 1 | A | 50.7 |
| 2 | P | 36.7 |
| 3 | V | 51.3 |
| 4 | H | 31.4 |
| 5 | R | 18.8 |
| 6 | G | 38.9 |
| 7 | R | 17.2 |
| 8 | G | 32.2 |
| 9 | G | 32.5 |
| 10 | W | 9.7 |
| 11 | T | 9.2 |
| 12 | L | 19.0 |
| 13 | N | 13.9 |
| 14 | S* | 3.6 |
| 15 | A | 12.2 |
| 16 | G | 12.0 |
| 17 | Y | 10.9 |
| 18 | L | 15.0 |
| 19 | L | 18.7 |
| 20 | G | 9.9 |
| 21 | P | 6.8 |
| 22 | V | 7.5 |
| 23 | L | 11.4 |
| 24 | H | —** |
| 25 | P | 7.0 |
| 26 | P | 9.7 |
| 27 | S* | 1.2 |

TABLE 2-continued

N-terminal amino acid sequence of auxiliary activating component (1)

| Cycle No. | PTH amino acid | Amount (pmol) |
|---|---|---|
| 28 | X | |
| 29 | A | 5.3 |
| 30 | E | 2.3 |
| 31 | G | 6.4 |
| 32 | G | 7.4 |

1) Raw data without correction for lag
2) S*: In addition to PTH-Ser, its degradation product (PTH-dehydroalanin-DTT adduct) was also detected.
3) Although the peak of the PTH-His was observed in the 24th cycle, it was below the quantification limit.
4) No PTH amino acid was identified in the 28th cycle.

From Table 2, the amino acid sequence from the N-terminal to the 32nd residue of the auxiliary GALR2-activating component (1) was determined as shown below (the 28th residue X was unknown).

APVHRGRGGWTLNSAGYLLGPVLHPPSXAEGG
(N-terminal amino acid sequence of auxiliary GALR2-activating component (1): SEQ ID NO: 12)

This amino acid sequence was in a complete agreement with the 32 residues of the N-terminal amino acid sequence of the main GALR2-activating component obtained in Step (4-1) described above.

(4-3) N-Terminal Amino Acid Sequencing of Auxiliary Component (2) having GALR2-Activating Effect The auxiliary GALR2-activating component (2) in Fraction Nos. 79 to 81 obtained in Step (3-3-5-3) described above was dissolved in 20 μl of 0.1% trifluoroacetic acid/30% acetonitrile, and ammonium bicarbonate (final concentration: 1%), TLCK-chymotrypsin (final concentration: 10 pmol, Sigma) and distilled water were added to make 50 μl, which was allowed to react at 37° C. for 1 hour.

A Spheri-5 RP-18 reverse phase high performance liquid chromatography column (BROWNLY, 2.1 mm×30 mm) was eluted with Solvent A (0.1% trifluoroacetic acid) at 25° C. and at the flow rate of 300 μl/min to be equilibrated.

The column was loaded with the entire amount of the enzyme reaction mixture, and then eluted at 300 μl/min over 30 minutes with 100% by volume of Solvent A (0.1% trifluoroacetic acid) which was changed into 70% by volume of Solvent B (0.1% trifluoroacetic acid/70% acetonitrile) to collect the effluent fractions corresponding to the four effluent peaks showing the UV absorption at 210 nm (CHY-1, CHY-2, CHY-3 and CHY-4).

The 4 fractions thus obtained (chymotrypsin-digested fragments) were concentrated under a nitrogen flow to a volume less than 50 μl, and then subjected to an N-terminal amino acid sequencing using a protein sequencer similarly to Step (4-1). CHY-3 was analyzed by a BECKMAN Model LF3400DT protein sequencer, while CHY-1, CHY-2 and CHY-4 were analyzed by an APPLIED BIOSYSTEM Model 477A protein sequencer.

The N-terminal amino acid sequencing revealed the following sequences.

```
                                         (SEQ ID NO: 13)
CHY-1: APVHRGRGG (SEQ ID NO: 16)
CHY-2: XAIDGLPYPQS (X is unknown)

(SEQ ID NO: 15)
CHY-3: LLGPVLHPPSXAEGGGKTALGILDL (X is unknown)

(SEQ ID NO: 14)
CHY-4: TLNSAG
```

Based on the N-terminal amino acid sequence of the main GALR2-activating component obtained in Step (4-1) described above or the auxiliary GALR2-activating component (1) obtained in Step (4-2) described above, the N-terminal amino acid sequence of the auxiliary GALR2-activating component (2) was assumed as follows.

```
                                         (SEQ ID NO: 17)
APVHRGRGGWTLNSAGYLLGPVLHPPSXAEGGGKTALGILDL
```

EXAMPLE 5 cDNA Encoding Porcine Ligand Peptide (1-60)

1) Cloning of Porcine GALR2-Activating Factor Gene Fragment by Degenerated PCR

From a porcine whole brain, a total RNA was extracted using a TRIZOL reagent (Gibco BRL) in accordance with the method described in an attached instruction. Subsequently, a poly(A)$^+$RNA was prepared from this total RNA using an oligo dT cellulose column (mRNA Purification Kit, Pharmacia) in accordance with the method described in an attached instruction. Then, a first strand cDNA was synthesized from this poly(A)$^+$RNA using a 3' RACE System for rapid amplification of cDNA ends (Gibco BRL) in accordance with the method described in an attached instruction. The following degenerative primers were synthesized based on the partial amino acid sequence of the porcine GALR2-activating component.

```
                                         (SEQ ID NO: 20)
pGAL4-7F:  5'-CAYMGNGGIMGNGGIGGSTGGAC-3'

(SEQ ID NO: 21)
pGAL9-3F:  5'-GGHTGGACNCTNAAYAGYGC-3'

(SEQ ID NO: 22)
pGAL34-1R: 5'-ATICCNAGIGCNGTYTTICCYTT-3'
```

The first strand cDNA described above was employed as a template to perform an initial PCR using pGAL4-7F and pGAL34-1R as primers. In this PCR, the reaction mixture was prepared by mixing 0.5 μl of Taq polymerase (TAKARA), 10 μl of each attached 10× PCR buffer (500 mM KCl-100 mM Tris.HCl, pH 8.3), 6 μl of 25 mM MgCl$_2$, 8 μl of 2.5 mM dNTP mixture, each 10 μl of primer pGAL4-7F and primer pGAL34-1R (both 10 μM), 8 μl of the template cDNA (first strand cDNA described above) and 47.5 μl of distilled water. This PCR involved 1) an initial degeneration (94° C. 30 seconds), 2) 32 cycles (94° C. 20 seconds −55° C. 30 seconds −72° C. 30 seconds) and then 3) a final elongation (72° C. 4 minutes), and yielded an initial PCR product.

The initial PCR product thus obtained was used as a template to perform the second PCR (nested PCR). The reaction mixture was prepared by mixing 0.5 μl of Taq polymerase (TAKARA), 10 μl of attached 10× PCR buffer (500 mM KCl-100 mM Tris.HCl, pH 8.3), 6 μl of 25 mM MgCl$_2$, 8 μl of 2.5 mM dNTP mixture, each 10 μl of primer pGAL9-3F and primer pGAL34-1R (both 10 µM), 5 µl of the template cDNA (initial PCR product) and 50.5 µl of distilled water. This PCR involved 1) an initial degeneration (94° C. 30 seconds), 2) 32 cycles (94° C. 20 seconds −55° C. 30 seconds −72° C. 30 seconds) and then 3) a final elongation (72° C. 10 minutes), and yielded a nested PCR product.

Furthermore, this nested PCR product was subjected to an electrophoresis on a 2.0% agarose gel, and a gel piece containing about 100 bp cybergreen-stained band was cut out by a knife. From this gel piece, a DNA fragment which was a nested PCR product was recovered using a Gene Clean DNA extraction kit (BIO 101). This DNA fragment was ligated using a TOPO TA Cloning Kit (Invitrogen) to a plasmid vector PCRII which was attached to the kit in accordance with the method described in an attached instruction. The plasmid thus obtained was purified using a QIAwell 8 Ultra plasmid purification kit (QIAGEN). The reaction for sequencing the base of the nested PCR product in this plasmid was performed using a Dye Terminator Cycle Sequencing Kit (Applied Biosystems, Perkin Elmer) and the base sequence of the nested PCR product was interpreted using a fluorescent automatic sequencer (DNA sequencer Prism 377; Applied Biosystems, Perkin Elmer). As a result, several plasmids each having a 98 bp DNA fragment encoding a partial peptide of a porcine GALR2-activating factor were obtained. Since the degenerate primers were employed in the PCR, the DNAs in these several plasmids differed from each other in the base sequences of the parts corresponding to the primers. The base sequences of the nested PCR products in the representative 2 clones, namely, pCR100-6 and pCR100-7.

```
pCR100-6:
                                            (SEQ ID NO: 23)
GGCTGGACTT TAAATAGTGC TGGTTACCTC CTGGGTCCCG
TACTCCATCC GCCCTCCAGG GCTGAAGGAG GCGGGAAGGG
CAAAACAGCC CTGGGCAT pCR100-7:
                                            (SEQ ID NO: 24)
GGTTGGACTT TGAACAGTGC TGGTTACCTC CTGGGTCCCG
TACTCCATCC GCCCTCCAGG GCTGAAGGAG GCGGGAAGGG
CAAAACCGCC CTAGGCAT
```

2) Cloning of cDNA Encoding Porcine Ligand Peptide (1-60)

From the poly(A)+RNA obtained from a porcine whole brain, a porcine whole brain cDNA phage library was prepared using a ZAP-cDNA Gigapack III Gold cloning kit (STRATAGENE). The method was in accordance with that described in an attached instruction. A resultant phage (2,200,000 plaque forming units) was infected with an E. coli XL1-Blue MRF' (STRATAGENE) by the method described in the instruction, and inoculated to 120 NZY medium agar plates, which were incubated at 37° C. for 8 hours. From an E. coli plaque thus obtained, a phage was transferred onto a Hybond-N+ nylon membrane (Amersham). This nylon membrane was immersed sequentially in a 0.5 N sodium hydroxide solution containing 1.5 M sodium chloride, a 0.5 M tris-buffer (pH 7.0) containing 1.5 M sodium chloride and 2×SSC solution, and then air-dried.

The resultant nylon membrane was kept in a hybridization buffer (5×SSPE, 5× Denhardt's solution, 0.5% SDS, 0.1 mg/ml salmon sperm DNA) at 60° C. for 24 hours, and then kept in a hybridization buffer similar to the former except for further containing a hybridization probe (5×10$^5$ cpm/ml) at 60° C. for 24 hours. This hybridization probe was a DNA amplified by the following 2 primers pGAL9-3F and pGAL34-8R using as a template a 1:1 mixture of the plasmids pCR100-6 and pCR100-7 described above.

```
                                            (SEQ ID NO: 25)
pGAL9-3F: 5'-GGHTGGACNCTNAAYAGYGC-3'

(SEQ ID NO: 26)
pGAL34-8R: 5'-ATDCCBAGGGCDGTTTTGCCCTT-3'
```

Thus, this amplification reaction [with the reaction mixture prepared by mixing 0.5 ml of ExTaq (TAKARA), 5 µl of attached 10×ExTaq buffer (containing 20 mM MgCl$_2$), 4 µl of 2.5 mM dNTP mixture, 10 µl of [α-$^{32}$P]dCTP(6000 Ci/mmol), each 0.5 µl of primer pGAL9-3F and primer pGAL34-8R (both 10 µM), 1 µl of the template cDNA and 29 µl of distilled water] involved an initial degeneration at 96° C. for 30 seconds, followed by 32 cycles of 94° C. 20 seconds −55° C. 30 seconds −72° C. 30 seconds, followed by a final elongation at 72° C. for 4 minutes, and yielded an amplified DNA fragment.

The nylon membrane after this hybridization reaction was washed with a 0.2×SSC buffer solution containing 0.1% SDS at 50° C. for 30 minutes and then subjected to an autoradiography using an X-ray film (Kodak, BioMax MS) in the presence of a sensitization screen (exposure at −70° C. for 3 days). A positive plaque detected as a result of the autoradiography was isolated and a phage was extracted into 5 ml of an SM buffer solution (100 mM NaCl, 8 mM MgSO$_4$, 0.01% gelatin, 50 mM Tris.HCl, pH 7.5) containing 0.1 ml of chloroform.

A resultant phage was infected again with E. coli XL1-Blue MRF' and then inoculated to NZY medium agar plates, which were incubated at 37° C. for 8 hours. From an E. coli plaque thus obtained, a phage was transferred onto a nylon membrane (Amersham, Hybond-N+), and a hybridization was performed as described above. A single positive clone was isolated by an autoradiography, and a series of the procedures described above were repeated again to obtain a completely single phage clone.

Subsequently, a plasmid was isolated from this phage clone and purified by the method described below. A phage solution (1 µl) was mixed with an E. coli XPORT (50 µl), a helper phage (10 µl) and an E. coli XLOLR (5 µl) and inoculated onto an NZY agar plate, which was incubated at 37° C. for 8 hours. A small colony of the E. coli XLOLR formed in the E. coli XPORT plaque was picked up with a toothpick and incubated in an LB medium containing ampicillin and tetracyclin overnight at 37° C. From a single colony, the E. coli XLOLR was picked up and subjected to a liquid incubation in an LB medium. After completing the incubation, the E. coli XLOLR was collected and a plasmid was purified using a plasmid purification kit (QIAGENE QIAwell 8 Ultra).

The reaction for the base sequencing of the cDNA encoding the porcine GALR2-activating factor in this plasmid was performed using a Dye Terminator Cycle Sequencing Kit (Applied Biosystems, Perkin Elmer) and the base sequence of the cDNA encoding the porcine GALR2-activating factor was interpreted using a fluorescent automatic sequencer (DNA sequencer Prism 377; Applied Biosystems, Perkin Elmer). As a result, a plasmid pGR2PL6 having a 974 bp DNA fragment and a plasmid pGR2PL3 having a 1007 bp DNA fragment, which encoded the entire peptide of the porcine GALR2-activating factor, were obtained. Although the chain lengths and the amino acid sequences of the precursors of the GALR2-activating factor encoded by the both DNA sequences differed greatly from each other, the sequences of the part of the mature activating factor (mature peptide) assumed to be produced by a processing were same to each other.

Each of the two plasmids thus obtained was transduced into an E. coli TOP10 by a known method to produce the transformants, TOP10/pGR2PL6 and TOP10/pGR2PL3.

EXAMPLE 6

Production of Porcine Ligand Peptide (1-60): Ala-Pro-Val-His-Arg-Gly-Arg-Gly-Gly-Trp-Thr-Leu-Asn-Ser-Ala-Gly-Tyr-Leu-Leu-Gly-Pro-Val-Leu-His-Pro-Pro-Ser-Arg-Ala-Glu-Gly-Gly-Gly-Lys-Gly-Lys-Thr-Ala-Leu-Gly-Ile-Leu-Asp-Leu-Trp-Lys-Ala-Ile-Asp-Gly-Leu-Pro-Tyr-Pro-Gln-Ser-Gln-Leu-Ala-Ser (SEQ ID NO: 31)

A commercially available Boc-Ser(Bzl)1-OCH$_2$-PAM resin (0.73 m mole/g resin) in the amount corresponding to 0.5 mmole was placed in a reactor of a peptide synthesizer ABI 430A, and Boc-Ala, Boc-Leu, Boc-Gln, Boc-Ser(Bzl), Boc-Pro, Boc-Tyr (Br-Z), Boc-Gly, Boc-Asp(OcHex), Boc-Ile, Boc-Lys(Cl-Z), Boc-Trp(CHO), Boc-Thr(Bzl), Boc-Glu (OcHex), Boc-Arg(Tos), Boc-His(Bom), Boc-Val and Boc-Asn were introduced in the desirable order of the amino acids by a Boc-strategy (NMP-HOBt) peptide synthesis method, whereby obtaining an intended protected peptide resin. Zero point one zero five grams of this resin was stirred together with 1.1 g of p-cresol and 1.2 ml of 1,4-butanedithiol in 10 ml of anhydrous hydrogen fluoride at 0° C. for 60 minutes, and then the hydrogen fluoride was distilled off under reduced pressure to obtain a residue, which was combined with diethylether to collect the precipitate by a filtration. This precipitate was extracted with a 50% aqueous acetic acid, and insolubles were removed, and the extract was concentrated thoroughly and then loaded onto a Sephadex® G-25 column (2.0×80 cm) packed with a 50% aqueous acetic acid, and eluted with the same solvent to collect a major fraction, which was subjected to a reverse phase chromatography column (2.6×60 cm) packed with a LiChroprep® RP-18, which was washed with 200 ml of a 0.1% aqueous TFA and then eluted with a linear gradient using 300 ml of a 0.1% aqueous TFA and 300 ml of a 50% aqueous acetonitrile containing 0.1% TFA, and a major fraction was collected, concentrated, lyophilized to obtain 39 mg of a white powder. This material was further loaded onto an ion exchange chromatography column packed with a CM-Cellulofine® and eluted with a linear gradient from 50 mM to 200 mM ammonium acetate to collect a major fraction, which was lyophilized repetitively to obtain 10 mg of a white powder.

(M+H)$^+$ in MS: Found: 6204.7 (calculated: 6205.2)

HPLC retention time: 21.8 minutes

Column Conditions

Column: Wakosil 5C18T, 4.6×100 mm

Eluent: Using Solvent A:0.1% aqueous TFA and Solvent B :0.1% TFA-containing acetonitrile with the linear gradient from A/B:95/5 to 45/55 (over 25 minutes)

Flow rate: 1.0 ml/min

EXAMPLE 7

Production of Rat Ligand Peptide (1-60): Ala-Pro-Ala-His-Arg-Gly-Arg-Gly-Gly-Trp-Thr-Leu-Asn-Ser-Ala-Gly-Tyr-Leu-Leu-Gly-Pro-Val-Leu-His-Leu-Ser-Ser-Lys-Ala-Asn-Gln-Gly-Arg-Lys-Thr-Asp-Ser-Ala-Leu-Glu-Ile-Leu-Asp-Leu-Trp-Lys-Ala-Ile-Asp-Gly-Leu-Pro-Tyr-Ser-Arg-Ser-Pro-Arg-Met-Thr (SEQ ID NO: 33) and Human Ligand Polypeptide (1-60): Ala-Pro-Ala-His-Arg-Gly-Arg-Gly-Gly-Trp-Thr-Leu-Asn-Ser-Ala-Gly-Tyr-Leu-Leu-Gly-Pro-Val-Leu-His-Leu-Pro-Gln-Met-Gly-Asp-Gln-Asp-Gly-Lys-Arg-Glu-Thr-Ala-Leu-Glu-Ile-Leu-Asp-Leu-Trp-Lys-Ala-Ile-Asp-Gly-Leu-Pro-Tyr-Ser-His-Pro-Pro-Gln-Pro-Ser (SEQ ID NO: 34)

A commercially available Boc-Thr(Bzl)1-OCH$_2$-PAM resin can be employed to perform the synthesis and the purification similarly to Example 1 to obtain the peptides.

EXAMPLE 8

Production of Antigen Peptide, Ala-Pro-Ala-His-Arg-Gly-Arg-Gly-Gly-Cys-NH$_2$ (amide form of SEQ ID NO: 44), Employed for Producing Monoclonal Antibody A commercially available p-methyl MBH resin (0.77 mmole/g resin) was employed in the manner similar to that in Example 1 to condense Boc-Cys(MeBzl), Boc-Gly, Boc-Arg(Tos), Boc-His(Bom), Boc-Ala and Boc-Pro in the desirable order of the amino acids, and then treated with hydrogen fluoride, purified on a Sephadex® G-25 column (2.0×80 cm) packed with a 50% aqueous acetic acid, lyophilized to obtain 50 mg of a white powder.

(M+H)$^+$ in MS: Found: 980.5 (calculated: 980.5)

HPLC retention time: 5.2 minutes

Column Conditions

Column: Wakosil 5C18T, 4.6×100 mm

Eluent: Using Solvent A:0.1% aqueous TFA and Solvent B :0.1% TFA-containing acetonitrile with the linear gradient from 0 to 50% Solvent B (over 25 minutes)

Flow rate: 1.0 ml/min

EXAMPLE 9

Production of Immunogen Containing Ala-Pro-Ala-His-Arg-Gly-Arg-Gly-Gly (SEQ ID NO: 35)

Using the peptide represented by Ala-Pro-Ala-His-Arg-Gly-Arg-Gly-Gly-Cys-NH$_2$(amide form of SEQ ID NO: 44) obtained in Example 8 described above was complexed with a keyhole limpet hemocyanin (KLH) to obtain an immunogen. Thus, 20 mg of KLH was dissolved in 1.4 ml of a 0.1 M phosphate buffer (pH 6.5), and then mixed with 100 μl of a DMF solution containing 2.2 mg (8 μmol) of N-(γ-maleimidobutyloxy)succinimide (GMBS) and reacted at room temperature for 40 minutes. After the reaction, the mixture was fractionated on a Sephadex G-25 column, and mixed with 15 mg of maleimide group-substituted KLH and 1.6 mg of the peptide represented by Ala-Pro-Ala-His-Arg-Gly-Arg-Gly-Gly-Cys-NH$_2$(amide form of SEQ ID NO: 44) and reacted at 4° C. for 2 days. After the reaction, the mixture was dialyzed against physiological saline at 4° C. for 2 days.

EXAMPLE 10

Immunization

A 6 to 8 weeks old BALB/C female mouse was immunized subcutaneously with about 30 μg/animal of the immunogen described in Example 9, i.e., Ala-Pro-Ala-His-Arg-Gly-Arg-Gly-Gly-Cys(-NH$_2$)—KLH together with a complete Freund's adjuvant. Thereafter an animal was boosted twice with the same amount of the immunogen together with the incomplete Freund's adjuvant every three weeks.

EXAMPLE 11

Preparation of Enzyme-Labeled Antigen Preparation of Horse Radish Peroxidase (HRP)-Labeled Peptide Ala-Pro-Ala-His-Arg-Gly-Arg-Gly-Gly-Cys-NH$_2$(Amide Form of SEQ ID NO: 44)

A peptide represented by Ala-Pro-Ala-His-Arg-Gly-Arg-Gly-Gly-Cys-NH$_2$(amide form of SEQ ID NO: 44) obtained in Example 8 was crosslinked with HRP (for enzyme immunoassay, Boehringer Mannheim) to obtain a labeled form for an enzyme immunoassay (EIA). Thus, 6 mg (150 nmol) of HRP was dissolved in 0.95 ml of a 0.1 M phosphate buffer (pH 6.5) and mixed with 50 μl of a DMF solution containing 0.42 mg (1.5 μmol) of GMBS and then the mixture was reacted at room temperature for 30 minutes and fractionated on a Sephadex G-25 column. Four point two milligrams (105 nmol) of the maleimide group-substituted HRP thus obtained and 0.31 mg (315 nmol) of the peptide represented by Ala-Pro-Ala-His-Arg-Gly-Arg-Gly-Gly-Cys-NH$_2$ (amide form of SEQ ID NO: 44) obtained in Example 9 were mixed and reacted at 4° C. for a day. After the reaction, the mixture was fractionated on an Ultrogel AcA44 (LKB-Pharmacia) column to obtain an HRP-labeled Ala-Pro-Ala-His-Arg-Gly-Arg-Gly-Gly-Cys-NH$_2$.

EXAMPLE 12

Determination of Antibody Titre in Antiserum of Mouse Immunized with Ala-Pro-Ala-His-Arg-Gly-Arg-Gly-Gly-Cys(-NH$_2$)—KLH Complex The antibody titre in a mouse antiserum immunized with an Ala-Pro-Ala-His-Arg-Gly-Arg-Gly-Gly-Cys(-NH$_2$)—KLH complex obtained in Example 9 was determined by the method described below. For preparing an anti-mouse immunoglobulin antibody-bound microplate, each 100 μl of a 0.1 M carbonate buffer (pH 9.6) containing 100 μg/ml of an anti-mouse immunoglobulin antibody (IgG fraction, KAPPEL) was dispensed to the 96-well microplate, which was allowed to stand at 4° C. for 24 hours. The plate was washed with a phosphate buffered saline (PBS, pH 7.4) and then each 300 μl of PBS containing 25% BLOCKACE (SNOW BRAND MILK PRODUCTS) was dispensed for the purpose of masking the excessive binding sites in a well, and then the treatment was continued for at least 24 hours at 4° C.

Figure 7:
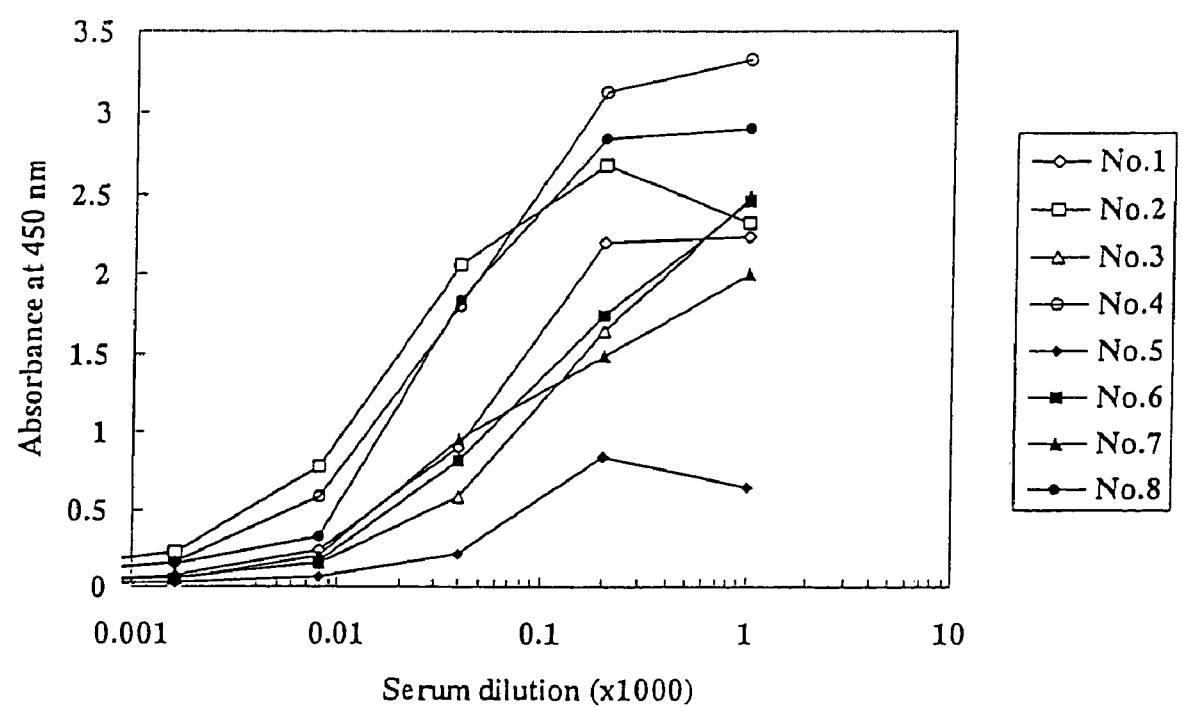
FIG. 7 shows the results of the antibody titre of a mouse immunized with an Ala-Pro-Ala-His-Arg-Gly-Arg-Gly-Gly-Cys(-NH$_2$)—KLH complex determined using HPR-labeled Ala-Pro-Ala-His-Arg-Gly-Arg-Gly-Gly-Cys-NH$_2$.

Each well of the anti-mouse immunoglobulin antibody-bound microplate obtained above received 50 μl of Buffer C[0.02 M phosphate buffer containing 1% BSA, 0.4M NaCl and 2 mM EDTA, pH 7.0] and 100 [1 of an Ala-Pro-Ala-His-Arg-Gly-Arg-Gly-Gly-Cys(-NH$_2$)—KLH complexed antiserum diluted with Buffer C, and was allowed to react at 4° C. for 16 hours. Subsequently, the plate was washed with PBS and received 100 μl of an HRP-labeled Ala-Pro-Ala-His-Arg-Gly-Arg-Gly-Gly-Cys-NH$_2$(500-fold diluted with Buffer C) prepared in Example 11 described above, and then was allowed to react at room temperature for 1 day. Then the plate was washed with PBS and the enzyme activity on the solid phase was determined by adding 100 μl of a TMB microwell peroxidase substrate system (KIRKEGAARD&PERRY LAB, Inc, available from FUNAKOSHI) followed by a reaction at room temperature for 10 minutes. One hundred microliter of a 1M phosphoric acid was added to quench the reaction, and the absorbance at 450 nmm was determined by a plate reader (BICHROMATIC, DAINIPPON PHARMACEUTICAL). The results are shown in FIG. 7. All of the 8 mice immunized exhibited the increase in the antibody titre against the Ala-Pro-Ala-His-Arg-Gly-Arg-Gly-Gly-Cys(-NH$_2$)—KLH complex.

EXAMPLE 13

Preparation of Monoclonal Antibody of Rat Ligand Peptide (1-60) (SEQ ID NO: 33)

A mouse exhibiting a relatively higher antibody titre was inoculated intravenously with 200 to 300 μg of the immunogen dissolved in 0.25 to 0.3 ml of physiological saline to effect the final immunization. A spleen was taken out from a mouse 3 to 4 days after the immunization, compressed by a stainless steel mesh, filtered, and suspended in an Eagles Minimum Essential Medium (MEM) to obtain a spleen cell suspension. As a cell to be fused, a BALB/C mouse-derived myeloma cell P3-X63. Ag8. U1 (P3U1) was employed [Current Topics in Microbiology and Immunology, 81, 1 (1978)]. The cell fusion was conducted in accordance with an original method [Nature, 256, 495 (1975)]. Thus, each of the spleen cell and P3U1 was washed three times with a serum-free MEM, and the spleen cell and P3U1 were mixed in the cell count ratio of 10:1, and then centrifuged at 800 rpm for 15 minutes to precipitate the cell. After removing a sufficient supernatant, the precipitate was pulverized gently, and then combined with 0.3 ml of a 45% polyethylene glycol (PEG) 6000 (KOCHLITE) and allowed to stand in a water bath at 37° C. for 7 minutes, whereby accomplishing the cell fusion. After the fusion, MEM was added at the rate of 2 ml/minute until 15 ml of MEM in total was added, and then the mixture was centrifuged at 600 rpm for 15 minutes to remove the supernatant. The cell precipitate thus obtained was suspended in a 10% fetal calf serum-supplemented GIT medium (WAKO PURE CHEMICAL) (GIT-10% FCS) at the density of 2×10$^5$ P3U1 cells per 1 ml, and 1 ml/well was added to 192 wells of 24-well multi-dishes (RINBRO). After the inoculation, the cell was incubated at 37° C. in a 5% CO$_2$ gas incubator. After 24 hours, 1 ml/well of a GIT-10% FCS medium containing HAT (Hypoxanthine 1×10$^{-4}$ M, aminopterin 4×10$^{-7}$ M, thymidine 1.6×10$^{-3}$M) (HAT medium) was added to initiate the HAT selective incubation. The HAT selective incubation was continued by discarding 1 ml of the old medium followed by adding 1 ml of the HAT medium 3, 6 and 9 days after initiation of the incubation. The proliferation of a hybridoma was noted on the 9th to 14th day after the cell fusion, and the supernatant was collected when the culture medium turned into yellow (about 1×10$^6$ cell/ml) and examined for the antibody titre according to the method described in Example 5.

As a representative case of the screening for a hybridoma derived from a mouse immunized with the Ala-Pro-Ala-His- Arg-Gly-Arg-Gly-Gly-Cys(-NH$_2$)—KLH complex, the results obtained using Mouse No. 8 (see FIG. 7) were indicated in FIG. 8.

Subsequently, those hybridomas exhibiting high antibody titres were cloned by a limiting dilution method. When cloning, as feeder cells, thymocyte of a BALB/C mouse were added to be 5×10$^5$ cells/well. After the cloning, a hybridoma was given intraperitoneally at a dose of 1 to 3×10$^6$ cell/animal to a mouse (BALB/C) which had previously been treated intraperitoneally with 0.5 ml of a mineral oil, and an antibody-containing ascites was collected after 6 to 20 days.

From an ascites obtained, a monoclonal antibody was purified on a protein-A column. Thus, 6 to 20 ml of the ascites was diluted with an equal-volume of a binding buffer (3.5 M NaCl, 0.05% NaN$_3$-supplemented 1.5 M glycine, pH 9.0), and then loaded onto a recombinant protein-A-agarose (Repligen) column which had previously been equilibrated with the binding buffer, and the specific antibody was eluted with an eluting buffer (0.05% NaN$_3$-supplemented 0.1 M citrate buffer, pH 3.0). The effluent was dialyzed against PBS at 4° C. for 2 days, sterilized by a filtration through a 0.22 µm filter (Millipore) and stored at 4° C. or –80° C. For determining the class and the sub-class of the monoclonal antibody, an enzyme-linked immunosorbent assay (ELISA) using a purified monoclonal antibody-bound solid phase was conducted. Thus, a 0.1 M carbonate buffer, pH 9.6, containing 2 µg/ml of the antibody was dispensed to a 96-well microplate in 100 µl aliquots, which were allowed to stand at 4° C. for 24 hours. According to the method described in Example 12, the excessive binding sites in a well were masked with BLOCKACE and then the class and the sub-class of an solidified antibody was investigated by an ELISA employing an isotype typing kit (Mouse-Typer™ Sub-Isotyping Kit, BIORAD).

EXAMPLE 14

Competitive Enzyme Immunoassay
(Competitive-EIA)

The reaction specificity of the monoclonal antibody prepared using the Ala-Pro-Ala-His-Arg-Gly-Arg-Gly-Gly-Cys (-NH$_2$)—KLH complex as an immunogen was investigated by the method described below. Thus, the antibody titre of each monoclonal antibody solution was determined by the method described in Example 12, and the antibody concentration at which the labeled substance binding level was about 50% of the saturated binding level (about 30 to 50 ng/ml) was determined as an antibody concentration employed in the competitive EIA. Subsequently, the anti-mouse immunoglobulin antibody-binding microplate described in Example 12 received 50 µl of the antibody solution which had been diluted to a predetermined concentration with Buffer C, 50 µl of Buffer C containing a 0.05% CHAPS solution of Ala-Pro-Ala-His-Arg-Gly-Arg-Gly-Gly-Cys-NH$_2$(amide form of SEQ ID NO: 44), the porcine ligand peptide (1-60) (SEQ ID NO: 31) and the rat galanin (SEQ ID NO: 61) and 50 µl of the HRP-labeled Ala-Pro-Ala-His-Arg-Gly-Arg-Gly-Gly-Cys-NH$_2$(250-fold diluted with Buffer C), which were then reacted at 4° C. for 16 hours. After the reaction followed by a washing with PBS, the enzyme activity on the solid phase was determined by the method described in Example 12. The results are shown in Table 3.

TABLE 3

Reactivity of monoclonal antibody with the peptide
Ala-Pro-Ala-His-Arg-Gly-Arg-Gly-Gly-Cys-NH$_2$
(amide form of SEQ ID NO: 44)
Reactivity 1)

| Hybridoma strain No. | SEQ ID NO: 44 | Porcine Ligand (SEQ ID NO: 31) | Rat Galanin (SEQ ID NO: 61) | Class/Subclass | Notes |
|---|---|---|---|---|---|
| 1 | + | − | − | | |
| 2 | + | + | − | IgGM, κ | |
| 3 | + | ± | − | IgG1, κ | |
| 4 | + | + | − | IgG2b, κ | GR2-1N |
| 5 | + | ± | − | | |
| 6 | + | + | − | IgG2b, κ | |
| 7 | + | − | − | | |
| 8 | + | − | − | | |

1) at the time when 100 nM antigen [SEQ ID NO: 44, SEQ ID NO: 31, SEQ ID NO: 61] is existed
+: (B/B$_0$) < 0.50
±: 0.50 ≤ (B/B$_0$) < 0.80
−: 0.80 ≤ (B/B$_0$)
wherein:
B: The level of HRP-labeled SEQ ID NO: 44 bound to the antibody in the presence of the antigen.
B$_0$: The level of HRP-labeled SEQ ID NO: 44 bound to the antibody in the absence of the antigen.

Figure 9:
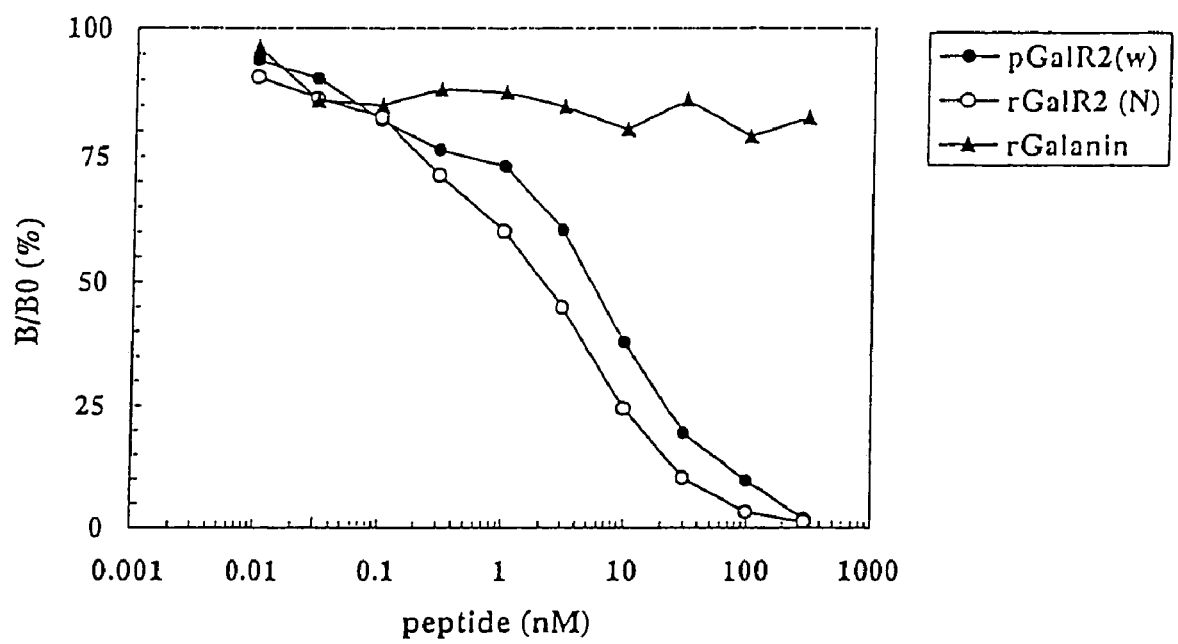
FIG. 9 shows the reactivities of a monoclonal antibody GR2-1N, produced by using as an immunogen an Ala-Pro-Ala-His-Arg-Gly-Arg-Gly-Gly-Cys(-NH$_2$)—KLH complex, with Ala-Pro-Ala-His-Arg-Gly-Arg-Gly-Gly-Cys-NH$_2$ (an amide form of SEQ ID NO: 44), a porcine ligand peptide (1-60) (SEQ ID NO: 31) and a rat galanin (SEQ ID NO: 61) when determined by a competitive EIA using HPR-labeled Ala-Pro-Ala-His-Arg-Gly-Arg-Gly-Gly-Cys-NH$_2$.

As a representative case, the results of the competitive EIA of the monoclonal antibody GR2-1N (IgG$_{2b}$, κ) which exhibited the highest reactivity with the porcine ligand peptide (1-60) (SEQ ID NO: 31) are shown in FIG. 9. As evident from this figure, while GR2-1N reacts with Cys-Ala-Pro-Ala-His-Arg-Gly-Arg-Gly-Gly (SEQ ID NO: 44) and with the porcine ligand peptide (1-60) (SEQ ID NO: 31) almost at the similar reactivity, it does not react with the rat galanin (SEQ ID NO: 61). Based on the calibration curve of GR2-1N vs the porcine ligand peptide (1-60) (SEQ ID NO: 31), the level of the porcine ligand peptide (1-60) (SEQ ID NO: 31) which gave (B/B$_0$)=0.5 was 6 nM, 4.95 ng/well, with the detection sensitivity being about 0.1 nM [(B/B$_0$) =0.8]. Accordingly, the competitive EIA employing GR2-1N enables a specific determination of the Ala-Pro-Ala-His-Arg-Gly-Arg-Gly-Gly-carrying rat ligand peptide (SEQ ID NO: 33) comprising, porcine ligand peptide (1-60) (SEQ ID NO: 31) or human ligand peptide (SEQ ID NO: 44) at the level as low as about 0.1 nM without undergoing any cross-reaction with SEQ ID NO: X (rat galanin).

EXAMPLE 15

Preparation of Porcine Ligand Peptide (1-34) (SEQ ID NO: 11)

Five nmol of the porcine ligand peptide (1-60) was kept in 250 µl of 1% ammonium bicarbonate containing 16% acetonitrile together with 50 pmol of lysyl endopeptidase (WAKO PURE CHEMICAL) at 37° C. for 3.5 hours.

A Spheri-5 RP-18 reverse phase high performance liquid chromatography column (BROWNLY, 2.1 mm×30 mm) had previously been eluted with Solvent A (0.1% trifluoroacetic acid) at the flow rate of 300 µl/min to be equilibrated at 25° C. The column was loaded with the enzyme reaction mixture, and then eluted at 300 µl/min over 30 minutes with increasing the concentration of Solvent B (0.1% trifluoroacetic acid/70% acetonitrile) to 70%. The effluent was monitored on the basis of the absorbance at 210 nm, and the peaks were fractionated manually.

The peak fraction eluted at 20.2 minutes exhibited MS data of M+H$^+$3466.5, validating the fragmented ligand peptide (1-34) of the porcine ligand peptide (1-60) also on the basis of the amino acid analysis.

EXAMPLE 16

Preparation of Porcine Ligand Peptide (1-30) (SEQ ID NO: 43)

Five nmol of the porcine ligand peptide (1-60) was kept in 250 µl of 1% ammonium bicarbonate containing 8% acetonitrile together with 50 pmol of endoproteinase Glu-C (Boehringer Mannheim) at 37° C. for 6 hours followed by at 25° C. for 13 hours.

The enzyme reaction mixture was separated in the condition similar to that for the porcine ligand peptide (1-34).

The peak fraction eluted at 19.8 minutes exhibited MS data of M+H$^+$3167.2, validating the fragmented ligand peptide (1-30) of the porcine ligand peptide (1-60) also on the basis of the amino acid analysis.

EXAMPLE 17

Galanin Receptor Binding Test Using [$^{125}$I] Rat Galanin

The membrane fraction prepared in Step (1-2) described above was suspended at 13 µg/ml (for GALR1 membrane fraction) or at 15 µg/ml (for GALR2 membrane fraction) in a 50 mM tris-buffer (pH 7.3) containing 0.1% bovine serum albumin (BSA), 5 mM Mgcl$_2$, 0.5 mM phenylmethylsulfonyl fluoride, 20 µg/ml leupeptin, 10 µg/ml pepstatin, 8 µg/ml E-64, and each 0.1 ml was dispensed into a small polypropylene tube (Falcon 2053). The membrane fraction thus dispensed was combined with 4 µl of 5 nM [$^{125}$I] rat galanin (New England Nuclear) and 1 µl of an inventive peptide synthesis product (porcine ligand peptide (1-60) (SEQ ID NO: 31), a limiting degradation product of an inventive peptide synthesis product (porcine ligand peptide (1-30) (SEQ ID NO: 43), porcine ligand peptide (1-34) (SEQ ID NO: 11) or rat galanin (PEPTIDE KENKYUSHO) (SEQ ID NO: 61) at a varying concentration (100 µM to 100 pM solution in dimethyl sulfoxide), and the mixture was reacted at 25° C. for 60 minutes. This reaction mixture was combined with 1.5 ml of a 50 mM tris buffer (pH 7.4) containing 0.05% 3-[(3-cholamidopropyl)dimethylammonio]propanesulfonic acid (CHAPS), 0.1% BSA, 5 mM MgCl$_2$, 1 mM EDTA and filtered through a GF/F glass fiber filter (Watmann). This filter was washed with 1.5 ml of the same buffer, and then examined for its radioactivity using a gamma counter.

The binding level observed in the presence of 1 µl of 100 µM rat galanin was regarded as a non-specific binding (NSB), while the binding level observed in the presence of 1 µl of dimethyl sulfoxide was regarded as the maximum binding (B$_0$), whereby calculating the peptide level IC$_{50}$ at which the maximum specific binding (B$_0$—NSB) was inhibited by 50% (Table 4).

TABLE 4

|  | IC$_{50}$ (nM) for rat GALR1 | IC$_{50}$ (nM) for rat GALR2 |
|---|---|---|
| SEQ ID NO:31 porcine (1-60) | 4.1 | 1.5 |
| SEQ ID NO:43 porcine (1-30) | 4.3 | 1.4 |

TABLE 4-continued

|  | IC$_{50}$ (nM) for rat GALR1 | IC$_{50}$ (nM) for rat GALR2 |
|---|---|---|
| SEQ ID NO:11 porcine (1-34) | NOT EXAMINED | 1.4 |
| SEQ ID NO:61 rat galanin | 0.25 | 0.71 |

EXAMPLE 18

Cloning of cDNA Encoding Rat Ligand Peptide (1-60)

By the method similar to that in Example 5, a total RNA was prepared from a rat hypothalamus using a TRIZOL reagent (Gibco BRL). From this total RNA, a poly(A)$^+$RNA was purified using an oligo dT cellulose column (mRNA Purification Kit, Pharmacia). From this poly(A)$^+$RNA, a rat hypothalamic cDNA phage library was prepared using a ZAP-cDNA Gigapack III Gold cloning kit (Stratagene). A resultant phage (2,200,000 plaque forming units) was infected with an E. coli XL1-Blue MRF' (Stratagene), and inoculated to 130 NZY medium agar plates, which were incubated at 37° C. for 8 hours. From an E. coli plaque thus obtained, a phage was transferred onto a Hybond-N$^+$ nylon membrane (Amersham). This nylon membrane was immersed sequentially in a 0.5 N sodium hydroxide solution containing 1.5 M sodium chloride, a 0.5 M tris-buffer (pH 7.0) containing 1.5 M sodium chloride and 2×SSC solution, and then air-dried.

The resultant nylon membrane was kept in a hybridization buffer (5×SSPE, 5× Denhardts solution, 0.1% SDS, 0.1 mg/ml salmon sperm DNA) at 60° C. for 24 hours, and then kept in a hybridization buffer similar to the former except for further containing a hybridization probe (2.8×10$^6$ cpm/ml) at 60° C. for 18 hours. This hybridization probe was the DNA fragment (356 base pairs) amplified by the primers pGAL1-1F and pGAL88-1R shown below together with the EcoRI/BglII digestion fragment of plasmid pGR2PL6 (SEQ ID NO: 45) as a template. The amplification reaction employed the reaction mixture prepared by mixing 0.5 µl of ExTaq (TAKARA), 10 µl of attached 10× PCR buffer (500 mM KCl-25 mM MgCl$_2$-100 mM Tris.HCl, pH 8.3), 8 µl of 2.5 mM dNTP mixture, 25 µl of [α-$^{32}$P]dCTP(6000 Ci/mmol), each 1 µl of primer pGAL9-3F and primer pGAL34-8R (both 10 µM), 1 µl of the template cDNA and 54 µl of distilled water, and involved an initial degeneration at 94° C. for 30 seconds, followed by 32 cycles of 94° C. 20 seconds –60° C. 30 seconds –72° C. 30 seconds, followed by a final elongation at 72° C. for 4 minutes.

```
                                              (SEQ ID NO: 46)
pGAL1-1F:  5'-ATGGCTCTGACTGTCCCTCTGATCGTTCT-3'

(SEQ ID NO: 47)
pGAL88-1R: 5'-TGAAACCTCGTAGTTCCTGGTCGGATTCG-3'
```

The nylon membrane after this hybridizaiton reaction was washed with a 2×SSC buffer solution containing 0.1% SDS at 50° C. and then subjected to an autoradiography using an X-ray film (Kodak, BioMax MS) in the presence of a sensitization screen (exposure at –70° C. for 3 days). A positive plaque identified as a result of the autoradiography was isolated and a phage was extracted into 5 ml of an SM buffer solution (100 mM NaCl, 8 mM MgSO$_4$, 0.01% gelatin, 50 mM Tris.HCl, pH 7.5) containing 0.1 ml of chloroform.

A resultant phage was infected again with *E. coli* XL1-Blue MRF' and then inoculated to NZY medium agar plates, which were incubated at 37° C. for 8 hours. From an *E. coli* plaque thus obtained, a phage was transferred onto a nylon membrane (Amersham, Hybond N⁺), and a hybridization was performed as described above. A single positive clone was selected by an autoradiography, and picked up using a capillary column. A series of the similar procedures described above were repeated again to obtain a completely single phage clone.

2.5 mM dNTP mixture, 3 μl of 25 mM MgCl$_2$, each 0.25 ml of primer F/R120 and R/R120 (both 100 μM), 1 μl of the template cDNA and 36 μl of distilled water, and subjected to an initial degeneration at 94° C. for 30 seconds, followed by 35 cycles of 94° C. 30 seconds –60° C. 30 seconds –72° C. 60 seconds, followed by a final elongation at 72° C. for 10 minutes. A resultant DNA fragment was cloned using a TOPO TA Cloning Kit (Invitrogen) in accordance with the method described in an attached instruction. The cloned DNA sequence was interpreted by the method described in Example 5 and the sequence represented by SEQ ID NO: 50 was obtained.

```
                                                                       (SEQ ID NO: 50)
           AGGCTGGACC CTCAATAGTG CTGGTTACCT TCTGGGTCCC GTCCTCCACC TTCCCCAAAT  60

GGGTGACCAA GACGGAAAGA GGGAGACAGC CCTTGAGATC CTAGACCTGT GGAAGGCCAT 120

AGATGG                                                            126
```

Subsequently, a plasmid was isolated from the cloned phage by the method described below.

A phage solution (1 μl) was mixed with an *E. coli* XPORT (50 μl), a helper phage (10 μl) and an *E. coli* XLOLR (5 ml) and inoculated onto an NZY agar plate, which was incubated at 37° C. for 8 hours. A small colony of the *E. coli* XLOLR formed in the *E. coli* XPORT plaque was picked up with a toothpick and incubated in an LB medium containing ampicillin and tetracyclin overnight at 37° C. From a single colony, the *E. coli* XLOLR was picked up and subjected to a liquid incubation in an LB medium. After completing the incubation, the *E. coli* XLOLR was collected and a plasmid was purified using a plasmid purification kit (QIAGENE QIAgen 8 Well Ultra).

A resultant plasmid was subjected to a sequencing reaction employing a Dye terminator Cycle Sequencing Kit (Applied Biosystems, Perkin Elmer) and the sequencing reaction product was interpreted using a DNA sequencer Prism 377 (Applied Biosystems, Perkin Elmer). As a result, a plasmid pGR2RL4 having a 974 bp DNA fragment (SEQ ID NO: 39) encoding the entire peptide of the rat ligand (1-60) was obtained. An *E. coli* TOP10 transformed with this plasmid was designated as TOP10/pGR2RL4.

EXAMPLE 19

Cloning of Human Ligand Peptide (1-60)

A human brain cDNA library was prepared from a human brain poly(A)⁺RNA (CLONTECH) using a ZAP-cDNA Synthesis kit (STRATAGENE). A resultant cDNA was employed as a template to perform a PCR using the following primers F/R120 and R/R120.

```
                                                   (SEQ ID NO: 48)
    F/R120: 5'-AGGCTGGACCCTCAATAGTGCTGGTTAC-3'

(SEQ ID NO: 49)
    R/R120: 5'-CCATCTATGGCCTTCCACAGGTCTAGGA-3'
```

The PCR reaction mixture was prepared by mixing 0.5 μl of Taq (TAKARA), 5 μl of attached 10× PCR buffer (500 mM KCl-25 mM MgCl$_2$-100 mM Tris.HCl, pH 8.3), 4 μl of From the resultant sequence, primers 1F/H120 (SEQ ID NO: 51) and 1R/H120 (SEQ ID NO: 52) were prepared and subjected to the 5'RACE and 3' RACE experiments described below.

```
                                                   (SEQ ID NO: 51)
    1F/H120: 5'-CAAATGGGTGACCAAGACGGAAAGAGGG-3'

(SEQ ID NO: 52)
    1R/H120: 5'-GGTCTAGGATCTCAAGGGCTGTCTCCCT-3'
```

The reaction mixture for the 5' RACE and 3' RACE experiments was prepared by mixing 0.5 μl of Taq (TAKARA), 5 μl of attached 10× PCR buffer (500 mM KCl-25 mM MgCl$_2$-100 mM Tris.HCl, pH 8.3), 4 μl of 2.5 mM dNTP mixture, 3 μl of 25 mM MgCl$_2$, 1 ml of 10 μM primer F/R120 (for 3'RACE) or 10 μM primer R/R120 (for 5'RACE), 1 μl of 10 μM primer AP1 (attached to Marathon-Ready cDNA Kit from CLONTECH), 5 μl of the template cDNA (CLONTECH, Marathon-Ready cDNA Kit, Human Hypothalamus) and 31 μl of distilled water. The reaction involved an initial degeneration at 94° C. for 60 seconds, followed by 5 cycles of 94° C. 30 seconds –72° C. 120 seconds, followed by 5 cycles of 94° C. 30 seconds –70° C. 120 seconds, followed by 25 cycles of 94° C. 30 seconds –68° C. 120 seconds, followed by a final elongation at 68° C. for 10 minutes.

Subsequently, a nested PCR was performed using the reaction solution of the PCR described above as a template.

The reaction mixture was prepared by mixing 0.5 μl of Taq (TAKARA), 5 μl of attached 10× PCR buffer (500 mM KCl-25 mM MgCl$_2$-100 mM Tris.HCl, pH 8.3), 4 μl of 2.5 mM dNTP mixture, 3 μl of 25 mM MgCl$_2$, 1 μl of 10 μM primer 1F/H120 (for 3'RACE) or 10 μM primer 1R/H120 (for 5'RACE), 1 μl of 10 μM primer AP2 (attached to Marathon-Ready cDNA Kit from CLONTECH), 5 μl of the template DNA (50-fold diluted PCR reaction solution) and 31 μl of distilled water. The reaction involved an initial degeneration at 94° C. for 60 seconds, followed by 5 cycles of 94° C. 30 seconds –72° C. 120 seconds, followed by 5 cycles of 94° C. 30 seconds –70° C. 120 seconds, followed by 25 cycles of 94° C. 30 seconds –68° C. 120 seconds, followed by a final elongation at 68° C. for 10 minutes.

A resultant DNA fragment was cloned using a TOPO TA Cloning Kit (Invitrogen) in accordance with the method described in an attached instruction. The cloned DNA sequence was interpreted by the method described in Example 5 (in the section of porcine cDNA cloning) to obtain sequence data at the 5'- and 3'-teminals. Based on these sequence data, the following primers 1F/H470 and 1R/H450 were prepared.

```
                                               (SEQ ID NO: 53)
1F/H470: 5'-GAGGAGCCAGAGAGAGCTGCGGAGAG-3'

(SEQ ID NO: 54)
1R/H470: 5'-GAGCTGGAGAAGAAGGATAGGAACAGGG-3'
```

This human brain cDNA library was employed as a template to perform a PCR using primers F/H450 and R/H450. The PCR reaction mixture was prepared by mixing 0.5 µl of Pfu turbo DNA polymerase (Stratagene), 5 µl of attached 10× PCR buffer (500 mM KCl-25 mM MgCl$_2$-100 mM Tris.HCl, pH 8.3), 4 µl of 2.5 mM dNTP mixture, each 2.5 ml of 10 µM primers F/H470 and R/H470, 0.5 µl of template human whole brain cDNA and 35 µl of distilled water. The reaction involved an initial degeneration at 94° C. for 30 seconds, followed by 35 cycles of 94° C. 30 seconds −70° C. 5 minutes, followed by a final elongation at 72° C. for 10 minutes. A resultant DNA fragment was cloned using a pPCR-Script Amp SK(+) vector (Stratagene) in accordance with the method described in an attached instruction. The cloned DNA sequence was interpreted by the method described in Example 5 (in the section of porcine cDNA cloning) to obtain pGR2HL14 comprising a 473 bp DNA fragment (SEQ ID NO: 40) encoding the human ligand entire peptide (1-60).

An *E. coli* TOP10 transformed with this plasmid was designated as TOP10/pGR2HL14.

EXAMPLE 20

Figure 10:
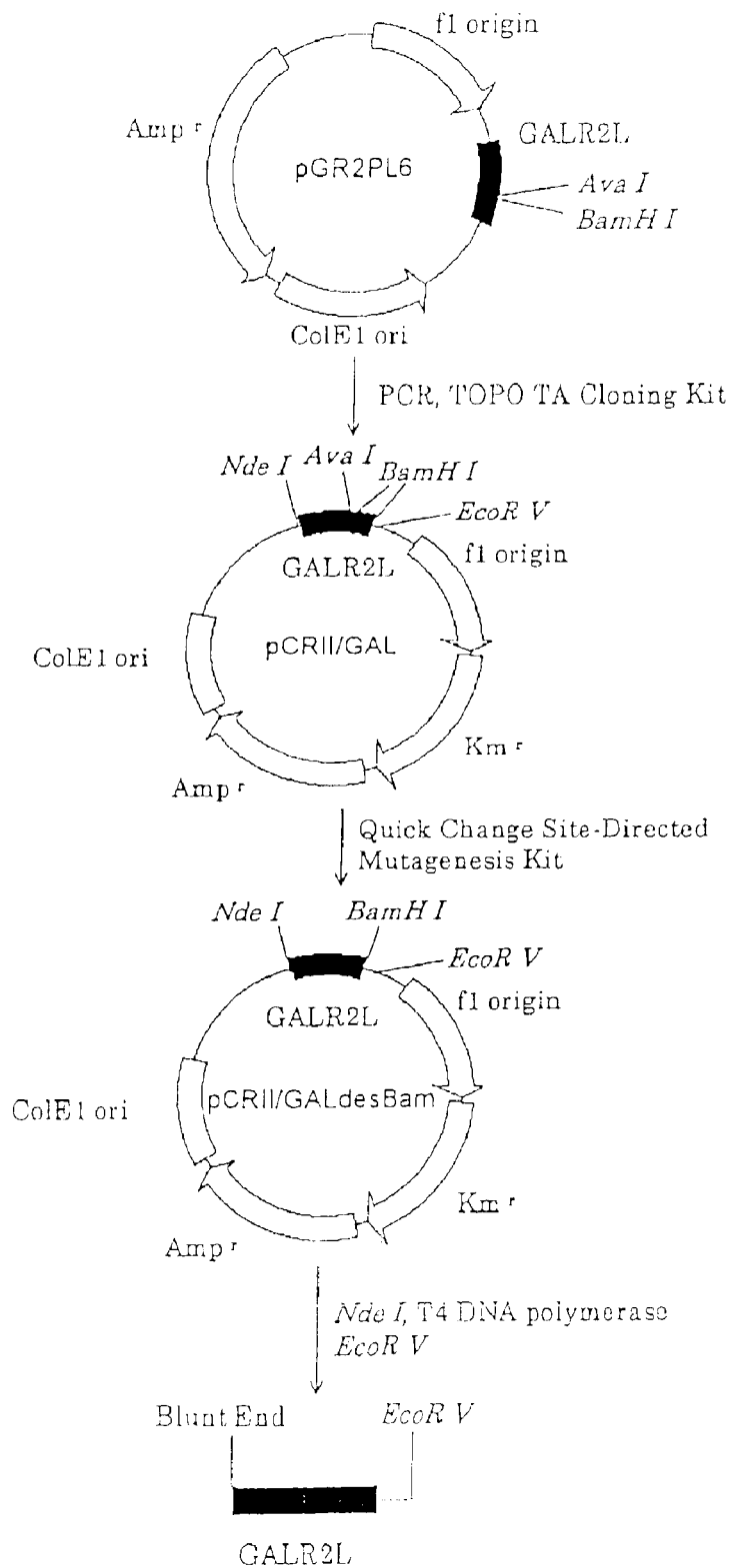
FIG. 10 is a scheme illustrating a procedure for preparing a structural gene of a porcine ligand peptide described in Example 20.

Preparation of Structural Gene of Porcine Ligand Peptide (1-60) (See FIG. 10)

A structural gene of an inventive (1-60) peptide was amplified by a PCR from plasmid pGR2PL6 obtained in Example 5 using Primer 1: 5'-AGCATATGGCTCCGGTC-CACAGG-3' (SEQ ID NO: 55, KIKKOTECH) having an Nde I cleavage site and methionin adjacent to the upstream of the structural gene and Primer 2: 5'-CTGGATCCTCAG-GAGGCCAACTGAGAC-3' (SEQ ID NO: 56, GLINER Japan) having a terminal codon and BamH I cleavage site adjacent to the downstream. This gene was ligated to a pCRII-TOPO vector using a TOPO TA Cloning Kit (Invitrogen) to produce pCRII/GAL. This plasmid was transformed to a TOP10 One Shot competent cell, which was inoculated onto an X-gal (5-Bromo-4-chloro-3-Indolyl-β-D-Galactose)-coated LB agar medium (1% pepton, 0.5% yeast extract, 0.5% sodium chloride, 2% agar) containing 50 µg/ml ampicillin and incubated at 37° C. for a day, and then a transformant was selected on the basis of the tetracyclin resistance and the β-galactosidase activity. This transformant was incubated overnight on an LB medium (1% pepton, 0.5% yeast extract, 0.5% sodium chloride) containing 50 µg/ml ampicillin, and then a plasmid was recovered using a QIAprep8 Miniprep Kit (QIAGENE). Also using Primer 3: 5'-CAGCCCTCGGCATCCTGGACC-3' (SEQ ID NO: 57, GLINER Japan) and Primer 4: 5'-GGTCCAGGAT-GCCGAGGGCTG-3' (SEQ ID NO: 58, GLINER Japan), a site specific variation induction (Quick Change, STRAT-AGENE) was performed to prepare pCRII/GALdesBam in which an Ava I recognition site present adjacent to BamH I in the structural gene of an inventive porcine ligand peptide (1-60) was deleted. The base sequence of the structural gene region of an inventive porcine ligand peptide (1-60) in the plasmid was verified using Applied Biosystems Model 377DNA Sequencer. 2 µg of pCRII/GALdesBam whose base sequence had been ensured was cleaved with Nde I and blunted using a T4 DNA polymerase (DNA Blunting Kit, TAKARA). After a cleavage with EcoR V followed by an electrophoresis on a 3% agarose gel, an about 200 bp DNA fragment was extracted using QIAquick Gel Extraction Kit (QIAGENE), and dissolved in 25 µl of a TE buffer (10 mM Tris-HCl (pH 8.0), 1 mM EDTA).

EXAMPLE 21

Figure 11:
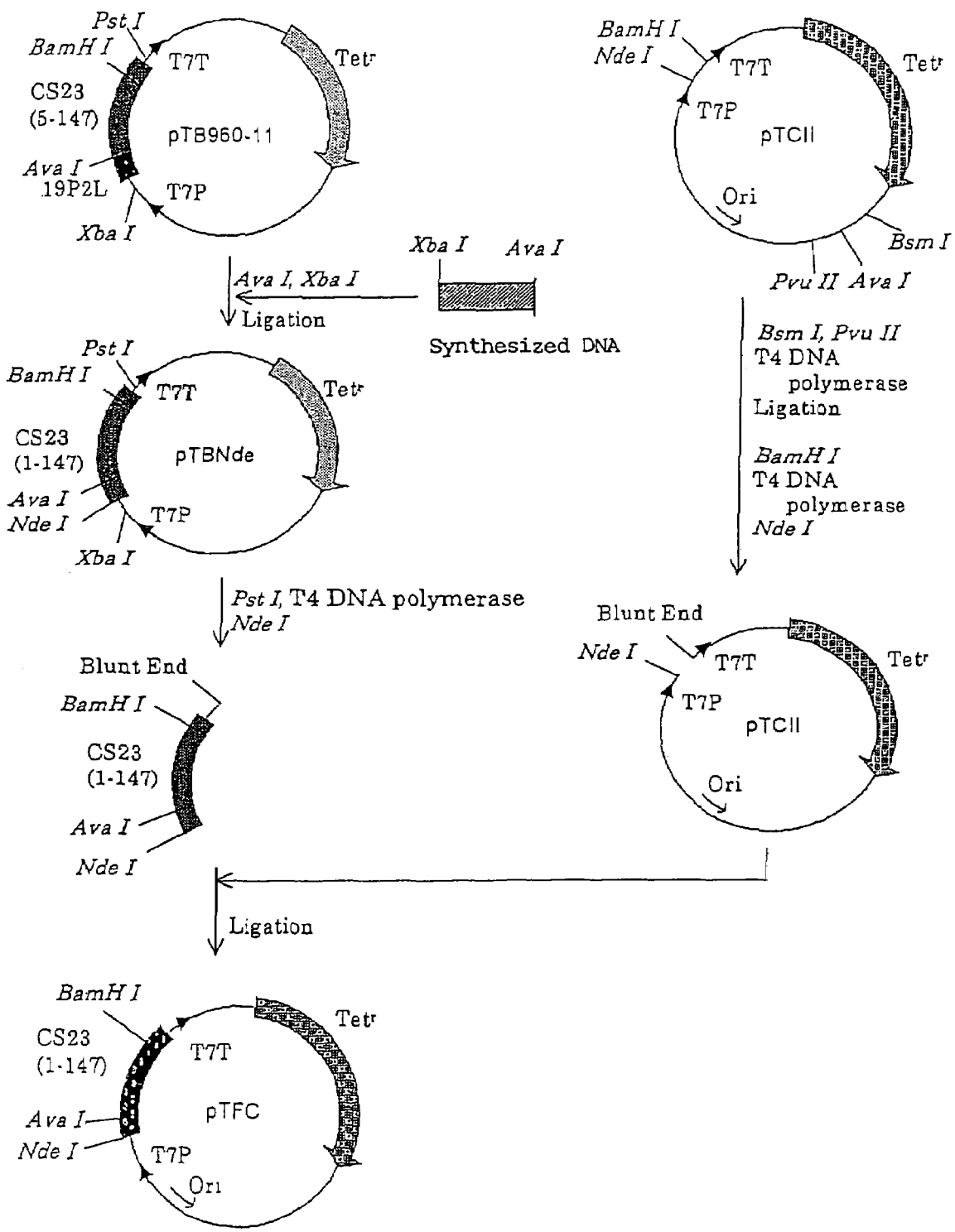
FIG. 11 shows a construction of a vector for expressing a fusion protein described in Example 21.

Preparation of Porcine Ligand Peptide (1-60)-Expressing Plasmid a) Preparation of Fusion Protein-Expressing Vector (See FIG. 11)

1 µg of plasmid pTB960-11 possessed by a transformant *Escherichia coli* MM294(DE3)/pTB960-11 which has been deposited to National Institute of Bioscience and Human Technology of Agency of Industrial Science and Technology of the Ministry of International Trade and Industry (NIBH) on Jun. 15, 1998 under the deposition number FERM BP-6388 and to Institute for Fermentation, Osaka (IFO) on Jun. 25, 1997 under the deposition No. IFO 16100 was cleaved with Xba I and Ava I and then subjected to a 1% agarose gel electrophoresis, and an about 4.4 kbp DNA fragment was extracted using QIAquick Gel Extraction Kit (QIAGENE), and dissolved in 50 µl of a TE buffer. Each 1 µl of the deletion part of an hFGF mutein CS23 structural gene and the synthetic DNAs (5'-CTAGACATATGCCAG-CATTGC-3' (SEQ ID NO: 59) and 5'-TCGGGCAATGCTG-GCATATGT-3' (SEQ ID NO: 60), both from GLINER Japan) which had been designed for effecting an upstream-adjacent insertion of an Nde I cleavage site and an initiation codon were reacted in 100 µL of a phosphorylation solution [50 mM Tris-HCl (pH 7.6), 10 mM MgCl$_2$, 5 mM dithiothreitol, 0.1 mM spermidine, 0.1 mM EDTA, 1 mM ATP, 10 unit T4 polynucleotide kinase (NIPPON GENE)] at 37° C. for 1 hour to effect a phosphorylation of a 5' terminal. After completing the reaction, a phenol-chloroform extraction and an ethanol precipitation were performed. The precipitation was dissolved in 50 µl of a TE buffer, which was then kept at 80° C. for 10 minutes and then allowed to cool, whereby effecting an annealing. The Xba I-Ava I DNA fragment and the annealing solution were ligated using Takara DNA Ligation Kit Ver 2 (TAKARA). Thus, 1 µL of Xba I-Ava I DNA fragment and 1 µL of annealing solution were combined with 3 µL of distilled water and 5 µL of Ligation Solution I and reacted at 16° C. for 30 minutes. 10 µL of this ligation solution was used to transform an *E. coli* JM109 competent cell (TOYOBO), which was inoculated onto an LB agar medium containing 10 µg/ml of tetracyclin, and then a tetracyclin-resistant colony formed was selected. This transformant was incubated on an LB medium overnight, and then a plasmid was prepared using a QIAprep8 Miniprep Kit (QIAGENE). This plasmid was cleaved with NdeI, and subjected to a 1% agarose gel electrophoresis to verify the formation of a new Nde I cleavage site, thus obtaining plasmid pTBNde.

Subsequently, 1 µg of plasmid pTBNde was cleaved with PstI, blunted using a T4 DNA polymerase (DNA Blunting Kit, TAKARA), and then subjected to a phenol-chloroform extraction and an ethanol precipitation. A precipitate thus obtained was dissolved in 10 μl of a TE buffer solution, cleaved with Nde I, subjected to a 3% agarose gel electrophoresis to obtain an about 470 bp DNA fragment, which was extracted using QIAquick Gel Extraction Kit (QIAGENE), and dissolved in 25 μL of a TE buffer.

Figure 12:
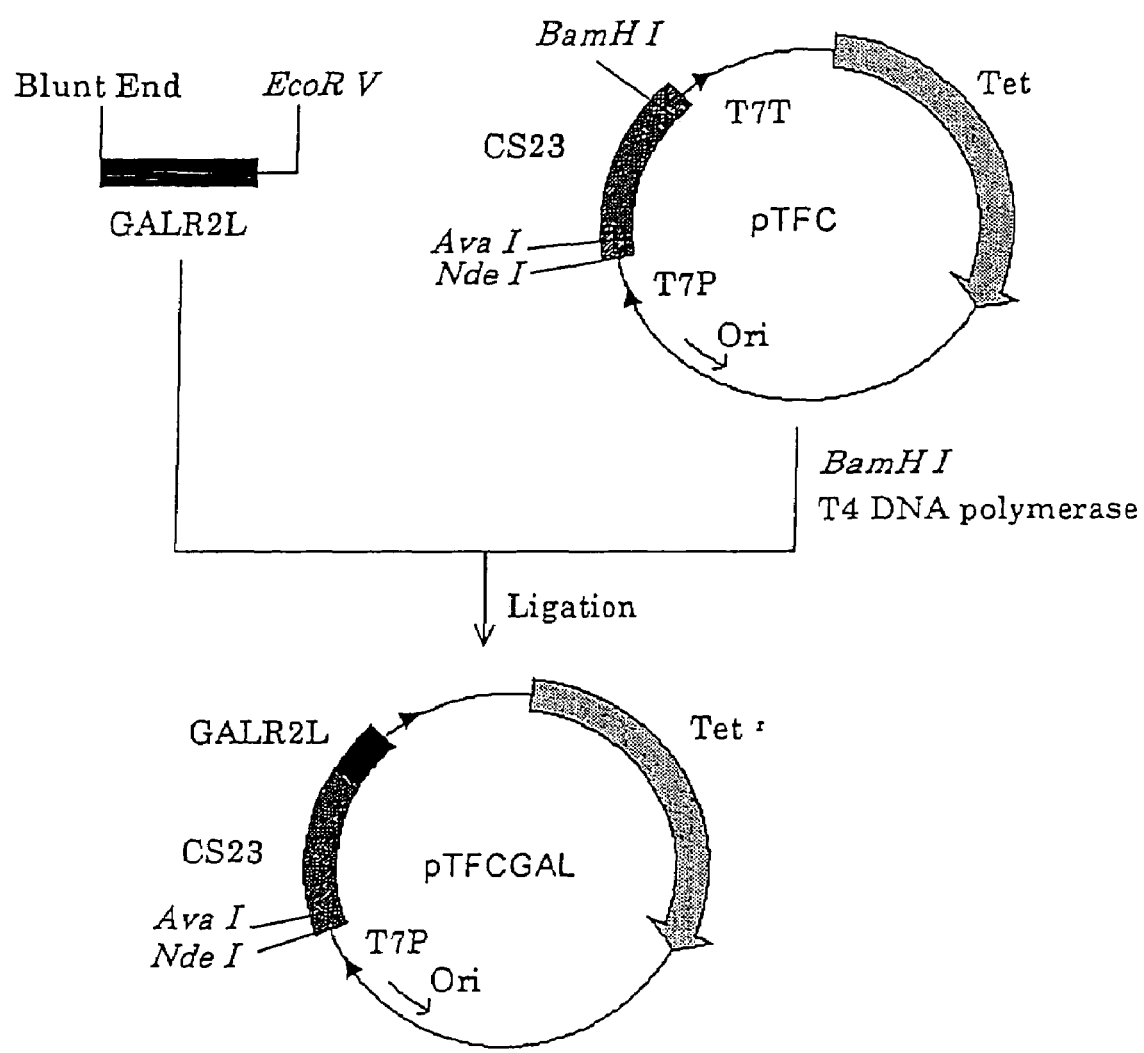
FIG. 12 shows a construction of a porcine ligand peptide expressing strain described in Example 21.

1 μl of plasmid pTCII possessed by a transformant *Escherichia coli* MM294(DE3)/pTCIId23-MPIF1 which has been deposited to National Institute of Bioscience and Human Technology of Agency of Industrial Science and Technology of the Ministry of International Trade and Industry (NIBH) on Nov. 24, 1998 under the deposition number FERM BP-6582 and to Institute for Fermentation, Osaka (IFO) on Oct. 27, 1998 under the deposition No. IFO 16212 was cleaved with Bsm I and Pvu II, and subjected to a 1% agarose gel electrophoresis to obtain an about 3.7 kbp DNA fragment, which was extracted using QIAquick Gel Extraction Kit, and dissolved in 25 μL of a TE buffer. This DNA fragment was blunted with a T4 DNA polymerase using a DNA Blunting Kit and then ligated. After the ligation followed by a phenol-chloroform extraction followed by an ethanol precipitation, the mixture was dissolved in 10 μL of a TE buffer. This solution was cleaved with BamH I and blunted with a T4 DNA polymerase, and then cleaved with Nde I, subjected to a 1% agarose gel electrophoresis to obtain an about 3.7 kbp DNA fragment, which was extracted using QIAquick Gel Extraction Kit, and dissolved in 50 μl of a TE buffer. 4 μL of an about 470 bp Nde I-Blunt DNA fragment and 1 μL of an about 3.7 kbp Nde I-Blunt DNA fragment described above were combined with 5 μL of Ligation Solution I and reacted at 16° C. for 30 minutes. 10 μL of this ligation solution was used to transform an *E. coli* JM109 competent cell (TOYOBO), which was inoculated onto an LB agar medium containing 10 μg/ml of tetracyclin, and then a tetracyclin-resistant colony formed was selected. This transformant was incubated on an LB medium overnight, and then a plasmid was prepared using a QIAprep8 Miniprep Kit, and designated as vector pTFC for expressing a fusion protein.

b) Construction of Porcine Ligand Peptide (1-60)-Expressing Strain (See FIG. 12)

1 μg of vector pTFC for expressing a fusion protein was cleaved with BamH I and blunted with a T4 DNA polymerase (DNA Blunting Kit, TAKARA), and then subjected to a 1% agarose gel electrophoresis to obtain an about 4.2 kbp DNA fragment, which was extracted using QIAquick Gel Extraction Kit (QIAGENE), and dissolved in 50 μl of a TE buffer. This fragment and an inventive peptide structural gene prepared in Example 20 were ligated using Takara DNA Ligation Kit Ver 2 (TAKARA). Thus, 1 μl of a BamH I-cleaved, blunted pTFC solution and 4 μL of the inventive peptide structural gene solution were mixed and then combined with 5 μL of Ligation Solution I and reacted at 16° C. for 30 minutes. 10 μg/mL of this ligation solution was used to transform an *E. coli* JM109 competent cell (TOYOBO), which was inoculated onto an LB agar medium containing 10 μg/ml of tetracyclin, which was incubated at 37° C. for a day, and then a tetracyclin-resistant colony formed was selected.

This transformant was incubated on an LB medium overnight, and then a plasmid was collected using a QIAprep8 Miniprep Kit (QIAGENE), and designated as inventive peptide-expressing plasmid pTFCGAL. The base sequence of the structural gene part of a fusion protein of this plasmid was verified using Applied Biosystems Model 377 DNA Sequencer. This expression plasmid pTFCGAL was transformed to an *E. coli* MM294(DE3), which was inoculated onto an LB agar medium containing 10 μg/ml of tetracyclin, which was incubated at 37° C. for a day, and then a tetracyclin-resistant transformant strain was selected, whereby obtaining an inventive peptide-expressing strain MM294(DE3)/pTFCGAL. This transformant *E. coli* strain MM294(DE3)/pTFCGAL has been deposited to National Institute of Bioscience and Human Technology of Agency of Industrial Science and Technology of the Ministry of International Trade and Industry on Mar. 10, 1999 under the deposition number FERM BP-6678. It has been deposited also to Institute for Fermentation, Osaka (IFO) on Feb. 26, 1999 under the deposition No. IFO 16260.

EXAMPLE 22

Incubation of Porcine Ligand Peptide (1-60)-Expressing Strain

The inventive peptide-expressing strain MM294(DE3)/pTFCGAL obtained in Example 21 was incubated with shaking in 1 L of an LB medium containing 5 mg/L tetracyclin at 37° C. for 16 hours. The culture fluid was transferred to a 50 L fementer charged with 20 L of a main fermentation medium (1.68% sodium monohydrogen phosphate, 0.3% potassium dihydrogen phosphate, 0.1% ammonium chloride, 0.05% sodium chloride, 0.05% magnesium sulfate, 0.0005% thiamine chloride, 1.5% glucose, 1.0% casamino acid, 1.0% yeast extract) and then incubated at 37° C. with stirring at 200 rpm and aerating at 20 L/min. When the turbidity of the culture fluid was about 1200 CRET units, isopropyl-β-D-thiogalactopyranoside (IPTG) was added at the final concentration of 23.8 mg/L. 30 and 150 minutes after the addition of IPTG, 0.75% glucose was added and the incubation was continued until 10 hours after the initiation of the incubation. The culture fluid was centrifuged at 5000 rpm for 30 minutes to obtain about 830 g of a bacterial cell.

EXAMPLE 23

Purification of Porcine Ligand Peptide (1-60)

200 g of the bacterial cell obtained in Example 22 was suspended in 600 ml of a 50 mM phosphate buffer (pH 7.0) containing 150 mM sodium chloride, 0.1 mM-amidinophenylmethanesulfonyl fluoride hydrochloride (APMSF) and 0.1 mM EDTA, treated ultrasonically (BRANSON SONIFIER MODEL450), centrifuged (10000 rpm for 10 minutes) to separate the supernatant off, whereby obtaining an inclusion body. This inclusion body was suspended in 60 mL of distilled water, combined with 140 ml of formic acid to effect dissolution, and then the cleavage at the peptide bond on the C-terminal side of methionine ligating fusion protein CS23 to the inventive porcine ligand peptide (1-60) was performed by an addition of 2 g of cyanogen bromide followed by a treatment at room temperature for 24 hours. After completion of the reaction, the solution was dialyzed against distilled water overnight, and centrifuged (10000 rpm for 10 minutes). The supernatant was dialyzed overnight against 50 mM Tris-HCl (pH 7.5), adjusted at pH 6.0 with hydrochloric acid, centrifuged (10000 rpm for 10 minutes) to obtain about 400 mL of the supernatant. This supernatant was applied at 10 mL/min to a CM-TOYOPEARL 650 M (3.0 cm ID×10 cm L, TOSOH) equilibrated with a 50 mM sodium acetate buffer (pH 6.0), and eluted, after a thorough washing with the equilibrating solution, with a stepwise gradient from 0 to 100% Solvent B (50 mM sodium acetate buffer+1M sodium chloride, pH 6.0), whereby obtaining a fraction containing an inventive porcine ligand peptide (1-60). A ⅓ volume of this fraction was applied at 5 mL/min to a C4P-50 (2.15 cm ID×30 cm L, SHOWADENKO) equilibrated with 0.1% trifluoroacetic acid, and eluted with a stepwise gradient from 33 to 43% Solvent B (80% acetonitrile/0.1% trifluoroacetic acid). The remaining ⅔ volume was subjected to the similar procedure to collect a fraction containing the inventive porcine ligand peptide (1-60), which was then lyophilized to yield 67 mg of a purified inventive porcine ligand peptide (1-60).

a) Analysis by SDS-Polyacrylamide Gel Electrophoresis

Figure 13:
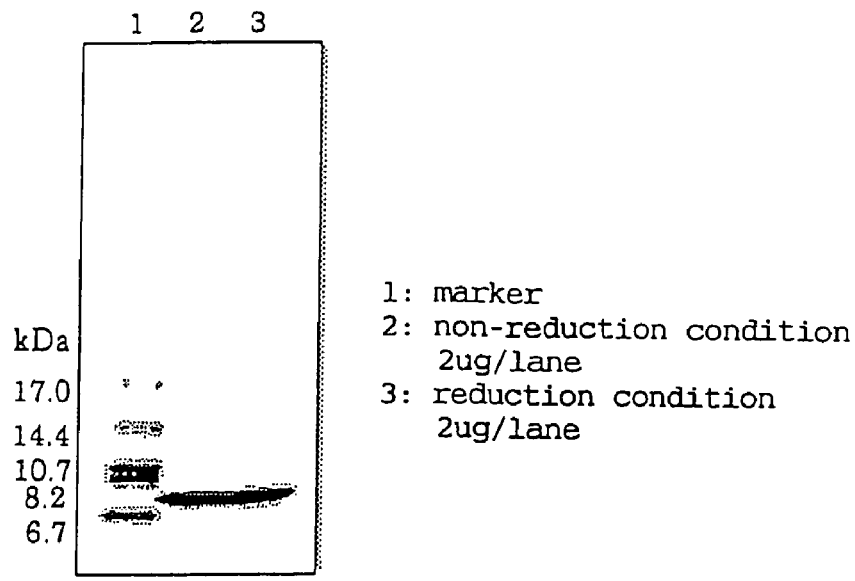
FIG. 13 shows the results of an SDS-polyacrylamide gel electrophoresis described in Example 23.

The purified inventive porcine ligand peptide (1-60) was dissolved in 0.0625 Tris-HCl (pH 6.8) containing 2% SDS, 10% glycerol, 5% 2-mercaptoethanol and 0.001% bromphenolblue [Laemmli, U K: Nature, 227, 680 (1979)], boiled for 3 minutes, and then subjected to an electrophoresis on MULTIGEL 15/25 (DAIICHI KAGAKU YAKUHIN). The gel after the electrophoresis was stained with RAPID CBB KANTO (KANTO KAGAKU), which revealed a single band (see FIG. 13).

b) Amino Acid Composition Analysis

The purified inventive porcine ligand peptide (1-60) was subjected to a gas phase hydrolyzation with 6 N hydrochloric acid containing 1% phenol at 110° C. for 24 and 48 hours, and then examined for the amino acid composition using an amino acid analyzer (HITACHI model L-8500A Amino Acid Analyzer). As a result, an agreement with the amino acid composition assumed from the cDNA base sequence was observed as evident from Table 5.

TABLE 5

Amino acid composition analysis

| Amino acid | Number of residue per 1 mole | Value assumed from the base sequence |
|---|---|---|
| Asp | 3.0 | 3 |
| Thr | 2.0 | 2 |
| Ser | 3.7 | 4 |
| Glu | 3.0 | 3 |
| Pro | 5.8 | 6 |
| Gly | 10.6 | 11 |
| Ala | 5.8 | 6 |
| Val | 1.9 | 2 |
| Ile | 1.9 | 2 |
| Leu | 9.0 | 9 |
| Tyr | 1.9 | 2 |
| Lys | 2.9 | 3 |
| His | 1.9 | 2 |
| Trp | 1.3 | 2 |
| Arg | 2.7 | 3 |

Ohr was substituted with Thr and Ser.
Val and Ile were of the values at 48 hr.

c) N-Terminal Amino Acid Sequencing Analysis

N-terminal amino acid sequence was determined using a gas phase protein sequencer (APPLIED BIOSYSTEMS, Model 477A). As a result, an agreement with the amino acid composition assumed from the cDNA base sequence was observed as evident from Table 6.

TABLE 6

N-terminal Amino acid sequencing

| Base No. | Detected PTH[1]- amino acid(pmol) | Amino acid assumed from base sequence |
|---|---|---|
| 1 | Ala(823) | Ala |
| 2 | Pro(676) | Pro |
| 3 | Val(719) | Val |
| 4 | His(355) | His |
| 5 | Arg(418) | Arg |
| 6 | Gly(548) | Gly |
| 7 | Arg(339) | Arg |
| 8 | Gly(470) | Gly |
| 9 | Gly(575) | Gly |
| 10 | Trp(189) | Trp |

Analyzed with 1 nmol.
[1] Phenylthiohydantoin d) C-Terminal Amino Acid Analysis

The purified inventive porcine ligand peptide (1-60) was subjected to a gas phase hydrolyzation with anhydrous hydrazine at 100° C. for 3.5 hours, and then examined for the C-terminal using an amino acid analyzer (HITACHI model L-8500A Amino Acid Analyzer). As a result, an agreement with the amino acid assumed from the cDNA base sequence was observed as evident from Table 7.

TABLE 7

C-terminal amino acid

| Amino acid at C-terminal | Recovery (%) |
|---|---|
| Ser | 61.5 |

Gas phase hydrazine degradation (100° C., 3.5 hours)

EXAMPLE 24

Ingestion Test

Figure 14:
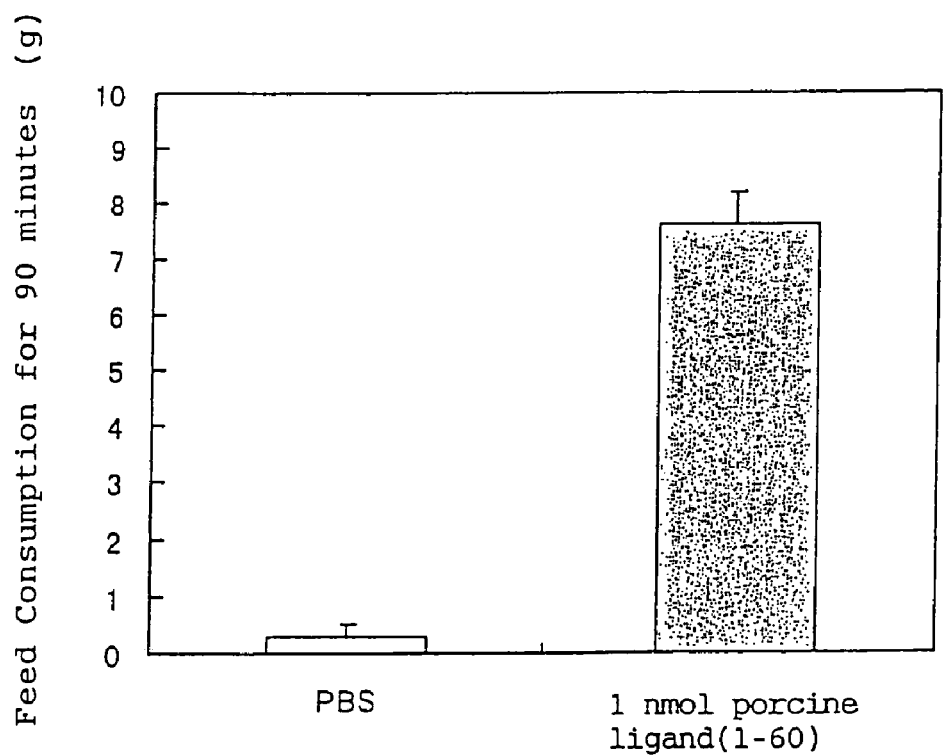
FIG. 14 shows the results of the feeding test conducted in Example 24.

The third ventricle (AP:−7.1, L:0.0, H:2.0 mm) of a male Wistar rat (8 W) under anesthesia with pentobarbital was cannulated with a guide cannula. After this surgery, the animal was allowed to recover for 1 week before an ingestion test. The animal was kept under the light/dark cycle of 12 hours (light: 8:00 to 20:00) and the ingestion test was initiated at 16:00. The rat under no anesthesia without any constraint was fitted with a microinjection cannula, through which it was treated with a porcine peptide (1-60) (SEQ ID NO: 31) dissolved in PBS or only PBS at 2.5 μl/min for 4 minutes. One minutes after completion of the treatment, the microinjection cannula was removed and the animal was allowed to access to a feed ad libitum. The feed ingested within 90 minutes after completion of the treatment was determined and represented as a feed consumption (FIG. 14).

INDUSTRIAL APPLICABILITY

A peptide of the invention or a precursor thereof, its amide or ester, or a salt thereof has an ability of activating a galanin receptor. Accordingly, it can be utilized in the development of a pharmaceutical having a low side effect, such as a function regulating agent in hypothalamus, pituitary gland, uterus, kidney, prostate or skeletal muscle where the galanin receptor is present in a large amount.

A use of a peptide of the invention or a precursor thereof, its amide or ester, or a salt thereof enables a screening for a compound which changes the binding activity with the galanin receptor.

---

The invention claimed is:

1. An isolated DNA comprising a nucleic acid base sequence encoding for a peptide having the amino acid sequence of SEQ ID NO: 34.

2. A DNA according to claim 1 comprising a nucleic acid base sequence of SEQ ID NO: 40 or 42.

3. A DNA according to claim 2 having the nucleic acid base sequence of SEQ ID NO: 40.

4. An isolated DNA having the nucleic acid base sequence of SEQ ID NO: 40.

5. An isolated DNA having the nucleic acid base sequence of SEQ ID NO: 42.

6. An isolated recombinant vector comprising a DNA according to claim 1.

7. An isolated transformant comprising a cell transformed with a recombinant vector according to claim 6.

8. A method for producing a peptide having an amino acid sequence of SEQ ID NO: 34, its amide or ester, or a salt thereof, which comprises cultivating the transformant according to claim 7 for sufficient time and under appropriate conditions to produce peptide, and producing a peptide.

* * * * *